US 6,606,992 B1

(12) United States Patent
Schuler et al.

(10) Patent No.: US 6,606,992 B1
(45) Date of Patent: Aug. 19, 2003

(54) SYSTEMS AND METHODS FOR AEROSOLIZING PHARMACEUTICAL FORMULATIONS

(75) Inventors: Carlos Schuler, Cupertino, CA (US); Steve Paboojian, Menlo Park, CA (US); Derrick J. Tuttle, San Mateo, CA (US); Adrian E. Smith, Belmont, CA (US); Dennis R. Rasmussen, Santa Clara, CA (US); Aneesh Bakshi, Belmont, CA (US); Andrew Clark, Half Moon Bay, CA (US); Brian R. S. Ward, Los Altos, CA (US); William W. Alston, Jr., San Jose, CA (US); Kevin S. Nason, Mountain View, CA (US)

(73) Assignee: Nektar Therapeutics, San Carlos, CA (US)

( * ) Notice: Subject to any disclaimer, the term of this patent is extended or adjusted under 35 U.S.C. 154(b) by 0 days.

(21) Appl. No.: 09/583,312

(22) Filed: May 30, 2000

Related U.S. Application Data
(60) Provisional application No. 60/141,793, filed on Jun. 30, 1999, and provisional application No. 60/198,060, filed on Apr. 18, 2000.

(51) Int. Cl.[7] .................. A61M 15/00; A61M 16/00; B05D 7/14; B65D 83/06
(52) U.S. Cl. ..................... 128/203.15; 128/203.12; 128/203.18; 128/203.21; 128/205.21; 128/203.23
(58) Field of Search .................. 128/203.15, 205.13, 128/203.12, 203.18, 203.21, 205.21, 203.23; 604/58

(56) References Cited

U.S. PATENT DOCUMENTS 2,587,215 A   2/1952   Priestly
3,788,310 A   1/1974   Fleischmann
3,837,341 A   9/1974   Bell
4,086,918 A   5/1978   Russo
4,106,503 A   8/1978   Rosenthal et al.
4,114,608 A   9/1978   Russo
4,170,228 A   10/1979  Elson et al.
4,176,617 A * 12/1979  Pilipski .................. 116/70
4,259,951 A   4/1981   Chernack et al.
4,274,404 A   6/1981   Molzan et al.
4,284,083 A   8/1981   Lester (List continued on next page.)

FOREIGN PATENT DOCUMENTS

EP   0808635 A2   11/1997
EP   0714314 B1   10/1998

(List continued on next page.)

OTHER PUBLICATIONS

Elliott et al., "Parental absorption of insulin from the lung in diabetic children" Aust. Paediatric Journal, 23, pp. 293–297 (1987).

(List continued on next page.)

Primary Examiner—Weilun Lo
Assistant Examiner—Darwin Erezo
(74) Attorney, Agent, or Firm—Guy V. Tucker; Felissa H. Cagan

(57) ABSTRACT

Systems and methods are provided for aerosolizing a pharmaceutical formulation. According to one method, respiratory gases are prevented from flowing to the lungs when attempting to inhale. Then, respiratory gases are abruptly permitted to flow to the lungs. The flow of respiratory gases may then be used to extract a pharmaceutical formulation from a receptacle and to place the pharmaceutical formulation within the flow of respiratory gases to form an aerosol.

55 Claims, 46 Drawing Sheets

U.S. PATENT DOCUMENTS

| | | | |
|---|---|---|---|
| 4,338,931 A | 7/1982 | Cavazza | |
| 4,391,283 A | 7/1983 | Sharpless et al. | |
| 4,442,856 A | 4/1984 | Betz | |
| 4,444,202 A | 4/1984 | Rubin et al. | |
| 4,484,577 A | 11/1984 | Sackner et al. | |
| 4,495,944 A | 1/1985 | Brisson et al. | |
| 4,533,137 A | 8/1985 | Sonne | |
| 4,558,710 A | 12/1985 | Eichler | |
| 4,592,348 A | 6/1986 | Waters, IV et al. | |
| 4,627,432 A | 12/1986 | Newell et al. | |
| 4,677,975 A | 7/1987 | Edgar et al. | |
| 4,778,054 A | 10/1988 | Newell et al. | |
| 4,811,731 A | 3/1989 | Newell et al. | |
| 4,907,583 A | 3/1990 | Wetterlin et al. | |
| 4,926,852 A | 5/1990 | Zoltan et al. | |
| 4,955,371 A | 9/1990 | Zamba et al. | |
| 4,991,745 A | 2/1991 | Brown | 222/212 |
| 5,027,806 A | 7/1991 | Zoltan et al. | |
| 5,033,655 A | 7/1991 | Brown | 222/212 |
| 5,040,527 A | 8/1991 | Larson et al. | |
| 5,042,467 A * | 8/1991 | Foley | 128/200.23 |
| 5,042,472 A | 8/1991 | Bunin | |
| 5,069,204 A | 12/1991 | Smith et al. | |
| 5,161,524 A | 11/1992 | Evans | |
| 5,167,506 A | 12/1992 | Kilis et al. | |
| 5,184,641 A | 2/1993 | Kuhn | |
| 5,201,308 A | 4/1993 | Newhouse | |
| 5,213,236 A | 5/1993 | Brown et al. | 222/185 |
| 5,284,133 A | 2/1994 | Burns et al. | |
| 5,301,666 A | 4/1994 | Lerk et al. | |
| 5,320,094 A | 6/1994 | Laube et al. | |
| 5,333,106 A | 7/1994 | Lanpher et al. | |
| 5,339,995 A | 8/1994 | Brown et al. | 222/185 |
| 5,364,838 A | 11/1994 | Rubsamen et al. | |
| 5,377,877 A | 1/1995 | Brown et al. | 222/105 |
| 5,385,140 A | 1/1995 | Smith | |
| 5,408,994 A | 4/1995 | Wass et al. | |
| 5,409,144 A | 4/1995 | Brown | 222/185 |
| 5,419,315 A | 5/1995 | Rubsamen | |
| 5,435,301 A | 7/1995 | Herold et al. | |
| 5,437,271 A | 8/1995 | Hodson et al. | |
| 5,439,143 A | 8/1995 | Brown et al. | 222/185 |
| 5,447,150 A | 9/1995 | Bacon | |
| 5,447,151 A | 9/1995 | Bruna et al. | |
| 5,458,135 A | 10/1995 | Patton et al. | 128/200.14 |
| 5,483,954 A | 1/1996 | Mecikalski | |
| 5,497,944 A * | 3/1996 | Weston et al. | 128/200.14 |
| 5,509,404 A | 4/1996 | Lloyd et al. | |
| 5,513,630 A | 5/1996 | Century | |
| 5,522,380 A * | 6/1996 | Dwork | 128/200.23 |
| 5,529,059 A | 6/1996 | Armstrong et al. | |
| 5,533,505 A | 7/1996 | Kallstrand et al. | |
| 5,542,412 A | 8/1996 | Century | |
| 5,558,085 A | 9/1996 | Rubsamen et al. | |
| 5,568,807 A | 10/1996 | Mecikalski | |
| 5,586,550 A | 12/1996 | Ivri et al. | |
| 5,617,845 A | 4/1997 | Poss et al. | |
| 5,622,166 A * | 4/1997 | Eisele et al. | 128/203.12 |
| 5,653,223 A * | 8/1997 | Pruitt | 128/200.21 |
| 5,654,007 A | 8/1997 | Johnson et al. | 424/489 |
| 5,655,520 A * | 8/1997 | Howe et al. | 128/203.12 |
| 5,672,581 A | 9/1997 | Rubsamen et al. | |
| 5,692,492 A | 12/1997 | Bruna et al. | |
| 5,692,496 A | 12/1997 | Casper et al. | |
| 5,692,498 A * | 12/1997 | Lurie et al. | 128/205.24 |
| 5,699,789 A | 12/1997 | Hendricks | |
| 5,724,959 A | 3/1998 | McAughey et al. | |
| 5,727,546 A | 3/1998 | Clarke et al. | |
| 5,740,794 A | 4/1998 | Smith et al. | |
| 5,752,505 A * | 5/1998 | Ohki et al. | 128/203.15 |
| 5,775,320 A | 7/1998 | Patton et al. | 128/200.14 |
| 5,785,049 A | 7/1998 | Smith et al. | |
| 5,813,401 A | 9/1998 | Radcliff et al. | |
| 5,823,183 A | 10/1998 | Casper et al. | |
| 5,826,571 A | 10/1998 | Casper et al. | |
| 5,826,633 A | 10/1998 | Parks et al. | 141/18 |
| 5,855,202 A | 1/1999 | Andrade | |
| 5,873,358 A | 2/1999 | Gonda et al. | |
| 5,875,776 A | 3/1999 | Vaghefi | |
| 5,881,719 A * | 3/1999 | Gottenauer et al. | 128/203.15 |
| 5,884,620 A | 3/1999 | Gonda et al. | |
| 5,896,853 A | 4/1999 | Howlett | |
| 5,901,703 A * | 5/1999 | Ohki et al. | 128/200.14 |
| 5,921,237 A | 7/1999 | Eisele | |
| 5,922,354 A | 7/1999 | Johnson et al. | 424/489 |
| 5,941,240 A | 8/1999 | Gonda et al. | |
| 5,975,076 A | 11/1999 | Yianneskis | |
| 5,983,893 A | 11/1999 | Wetterlin | |
| 5,988,163 A | 11/1999 | Casper | |
| 5,993,421 A | 11/1999 | Kriesel | |
| 6,006,747 A | 12/1999 | Eisele | |
| 6,012,454 A | 1/2000 | Hodson et al. | |
| 6,029,661 A | 2/2000 | Whaley et al. | |
| 6,029,663 A * | 2/2000 | Eisele et al. | 128/203.21 |
| 6,055,979 A | 5/2000 | Fuchs | |
| 6,055,980 A | 5/2000 | Mecikalski | |
| 6,062,219 A * | 5/2000 | Lurie et al. | 128/205.24 |
| 6,065,472 A * | 5/2000 | Anderson et al. | 128/203.21 |
| 6,070,573 A | 6/2000 | Howe et al. | |
| 6,076,523 A | 6/2000 | Jones et al. | |
| 6,085,753 A | 7/2000 | Gonda et al. | |
| 6,089,228 A | 7/2000 | Smith et al. | 128/203.15 |
| 6,095,134 A | 8/2000 | Sievers et al. | |
| 6,102,036 A | 8/2000 | Slutsky et al. | |
| 6,105,574 A | 8/2000 | Jahnsson | |
| 6,109,261 A | 8/2000 | Clarke et al. | |
| 6,116,237 A | 9/2000 | Schultz et al. | |
| 6,116,238 A * | 9/2000 | Jackson et al. | 128/203.15 |
| 6,116,239 A | 9/2000 | Volgyesi | |
| 6,138,673 A * | 10/2000 | Shepherd | 128/203.15 |
| 6,142,146 A | 11/2000 | Abrams et al. | |
| 6,176,237 B1 * | 1/2001 | Wunderlich et al. | 128/203.12 |

FOREIGN PATENT DOCUMENTS

| | | |
|---|---|---|
| EP | 0805696 B1 | 3/2000 |
| GB | 1598053 | 9/1981 |
| HU | 212398 | 6/1996 |
| HU | 214757 | 5/1998 |
| HU | 219215 | 3/2001 |
| WO | WO 91/14422 | 10/1991 |
| WO | WO95/24183 | 2/1995 |
| WO | WO 95/34337 | 12/1995 |
| WO | WO 96/09085 | 3/1996 |
| WO | WO 96/30068 | 10/1996 |
| WO | WO96/32149 | 10/1996 |
| WO | WO 96/32149 | 10/1996 |
| WO | WO99/16419 | 9/1997 |
| WO | WO 97/40819 | 11/1997 |
| WO | WO 98/32479 | 7/1998 |
| WO | WO99/47196 | 3/1999 |
| WO | WO 99/27987 | 6/1999 |
| WO | WO 99/46055 | 6/1999 |
| WO | WO 99/47196 | 9/1999 |
| WO | WO 00/01435 | 1/2000 |
| WO | WO 00/21594 | 4/2000 |

OTHER PUBLICATIONS

Lawford et al., "Pressurized Aerosol Inhaler Technique: How Important Are Inhalation from Residual Volume, Inspiratory Flow Rate and the Time Interval Between Puffs?" Br. J. Dis. Chest, 77, pp. 276–281, 1983.

Ross et al., "Effect of Inhalation Flow Rate on the Dosing Characteristics of Dry Powder Inhaler (DPI) and Metered Dose Inhaler (MDI) Products" Journal of Aerosol Medicine, vol. 9, No. 2, pp. 215–226, 1996.

Hill, "Characteristics of an Active, Multiple Dose Dry Powder Inhaler" Respiratory Drug Delivery IV, pp. 109–116, 1994.

Conway et al., "Comparison of peak Pressure Drops Through Powder Inhalers During Inspiration at Maximum Flow Rate" Abstract from American Journal of Respiratory and Critical Care Medicine, vol. 153, No. 4, A59, Apr. 1996.

Clark, "Effect of powder inhaler resistance upon inspiratory profiles in health & disease," Respirator Drug Delivery IV, 1994.

Clark, "The relationship between powder inhaler resistance and peak inspriatry conditions in healthy volunteers—implications for in vitro testing," Journal of Aerosol Science, 1993.

"Characteristics of an active multiple dose dry powder inhaler" Dura RDD, 1994.

Dolovich, "Physical principles underlying aerosol therapy," Journal Aerosol Medicine, 1989.

NP Nantel et al., "Flowing Targeting System for DPI Clinical Trials" *Barrett Medical Aerosol Research Laboratory*, p136.

D. Prime et al., "The Flixotide Diskus a new multiple powder inhaler–in–vitro evaluation using an inhalation simulator," *Glaxo Research and Development*, p137.

D. Prime et al., "The Flixotide Diskus a new multi powder inhaler–consistency of dose and fine particle mass, protection from moisture," *Glaxo Research and Development*, p138.

D.L.N. Robertson et al., "The influence of (pseudo) polymorphic forms of lactose on dry powder inhaler performance," School of Pharmacy and Pharmacology, p. 139.

Barrowcliffe et al. "The In–Vitro Evaluation of Novel Multi–Dose Dry Powder Inhaler," CCL Pharmaceuticals Ltd., p. 82–85.

Malton et al. "A Comparison of in vitro drug delivery from two multidose powder inhalation devices," European Journal of Clinical Research 1995:7:p177–193.

Agenda for *Asthma Therapy I—Thematic Poster Session May 12, 1996*, American Journal of Respiratory Critical Care Medicine:153(4): Apr. 1996.

Malton et al. "A Comparison of *in vitro* drug delivery from slabutamol Diskus and terbutaline Turbohaler inhalers," J. Pharm. Med. (1996) 6, p. 35–48.

Chrystyn, Henry, "The Diskus Inhaler–A Review of its Pharmacetical and Clinical Performance," *Clin Drug Invest* 18(4):287–296, (1999).

Newhouse et al. "Clickhaler (a Novel Dry Powder Inhaler) Provides similar Bronchodilatation to Pressurized Metered–Dose Inhaler, Even at Low Flow Rates," CHEST 115(4):952–956: Apr. 1999.

* cited by examiner

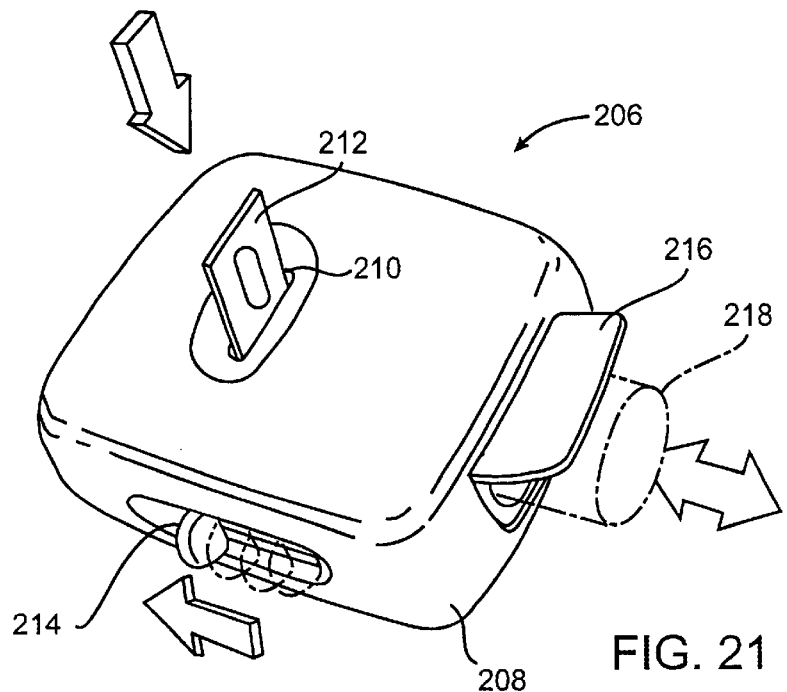
FIG. 21
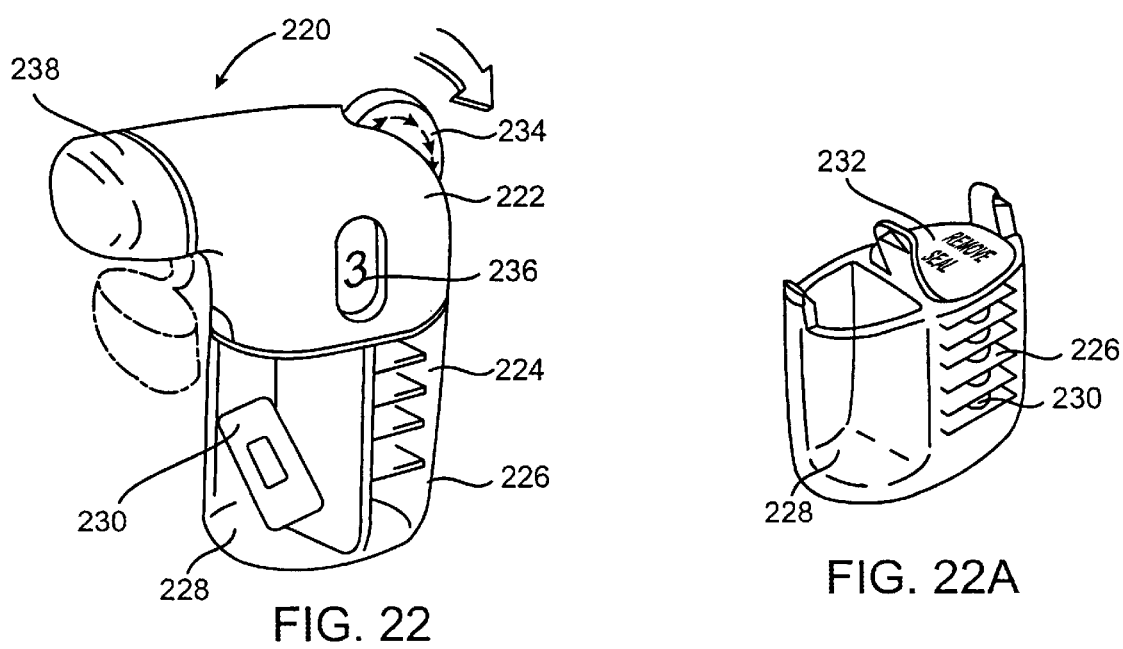
FIG. 22
FIG. 22A

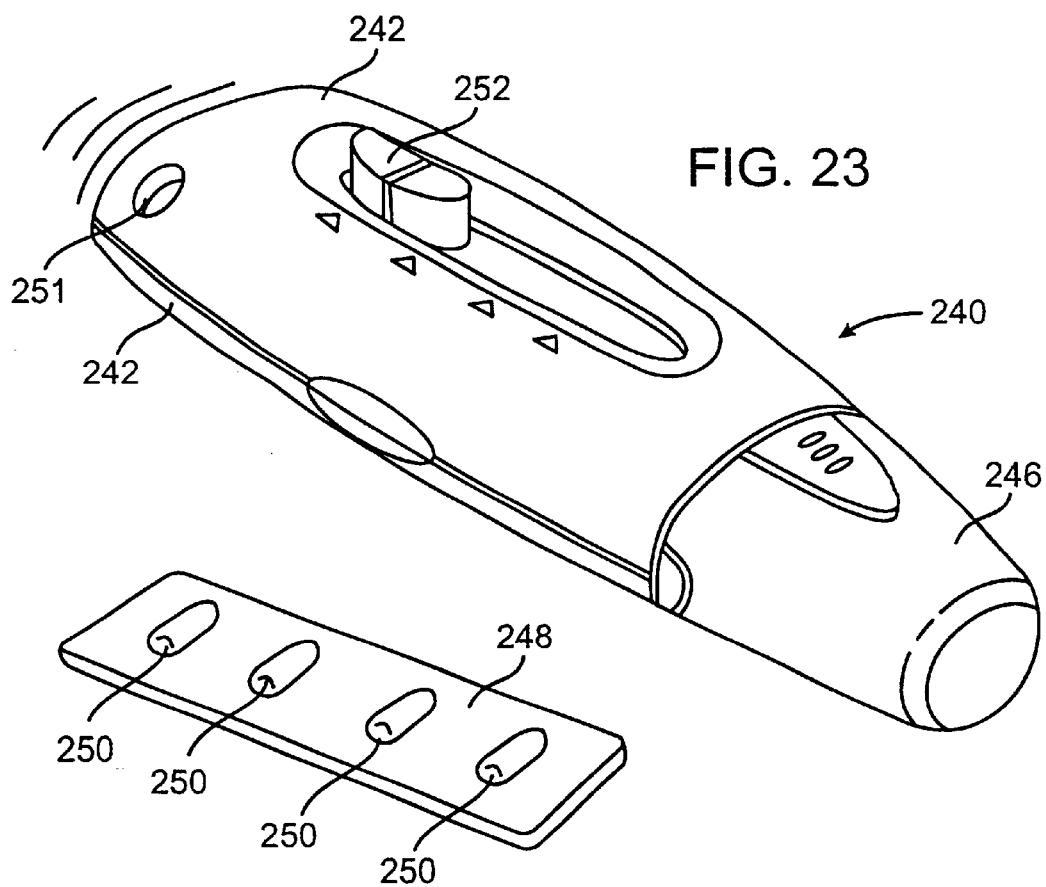
FIG. 23
FIG. 24
FIG. 23A

_US 6,606,992 B1_

SYSTEMS AND METHODS FOR AEROSOLIZING PHARMACEUTICAL FORMULATIONS

CROSS REFERENCE TO RELATED APPLICATIONS

This application is a continuation in part application and claims the benefit of U.S. Provisional Patent Application Nos. 60/141,793, filed Jun. 30, 1999 and 60/198,060, filed Apr. 18, 2000, the complete disclosures of which are herein incorporated by reference.

BACKGROUND OF THE INVENTION

This invention relates generally to the field of drug delivery, and in particular to the delivery of pharmaceutical formulations to the lungs. More specifically, the invention relates to the aerosolization of pharmaceutical formulations using energy created by patient inhalation.

Effective drug delivery to a patient is a critical aspect of any successful drug therapy, and a variety of drug delivery techniques have been proposed. For example, one convenient method is the oral delivery of pills, capsules, elixirs and the like. However, oral delivery can in some cases be undesirable in that many drugs are degraded in the digestive tract before they can be absorbed. Another technique is subcutaneous injection. One disadvantage to this approach is low patient acceptance. Other alternative routes of administration that have been proposed include transdermal, intranasal, intrarectal, intravaginal and pulmonary delivery.

Of particular interest to the invention are pulmonary delivery techniques which rely on the inhalation of a pharmaceutical formulation by the patient so that the active drug within the dispersion can reach the distal (alveolar) regions of the lung. A variety of aerosolization systems have been proposed to disperse pharmaceutical formulations. For example, U.S. Pat. Nos. 5,785,049 and 5,740,794, the disclosures of which are herein incorporated by reference, describe exemplary powder dispersion devices which utilize a compressed gas to aerosolize a powder. Other types of aerosolization systems include MDI's (which typically have a drug that is stored in a propellant), nebulizers (which aerosolize liquids using compressed gas, usually air), and the like.

Another technique which is of interest to the invention is the use of inspired gases to disperse the pharmaceutical formulation. In this way, the patient is able to provide the energy needed to aerosolize the formulation by the patient's own inhalation. This insures that aerosol generation and inhalation are properly synchronized. Utilization of the patient's inspired gases can be challenging in several respects. For example, for some pharmaceutical formulations, such as insulin, it may be desirable to limit the inhalation flow rate within certain limits. For example, PCT/US99/04654, filed Mar. 11, 1999, provides for the pulmonary delivery of insulin at rates less than 17 liters per minute. As another example, copending U.S. patent application Ser. No. 09/414,384 describes pulmonary delivery techniques where a high flow resistance is provided for an initial period followed by a period of lower flow resistance. The complete disclosures of all the above references are herein incorporated by reference.

Another challenge in utilizing the patient's inspired gases is that the inspiration flow rate can drastically vary between individuals. For instance, as shown in FIG. 1, a random sample of 17 individuals which were measured twice a week for four weeks produced flow rates ranging from about 5 liters per minute to about 35 liters per minute. Such variability may affect the ability of the formulation to be dispersed within a gas stream, the ability to deagglomerate a powdered formulation, and/or the ability of the aerosolized formulation to adequately reach the deep lung.

Hence, this invention is related to techniques for regulating the flow of inspired gases that may be utilized when dispersing a pharmaceutical formulation. In one aspect, the invention is related to techniques to enhance the ability of a formulation to be dispersed within a gas stream produced by patient inhalation, to enhance the ability to deagglomerate a powdered formulation, and to enhance the ability of the aerosolized formulation to adequately reach the deep lung.

SUMMARY OF THE INVENTION

The invention provides exemplary systems and methods to provide breath actuated, flow regulated aerosol delivery of pharmaceuticals. In one aspect, the invention utilizes the flow of respiratory gases produced by a patient to aerosolize a pharmaceutical formulation. In another particular aspect of the invention, the invention is able to extract a powdered pharmaceutical formulation from a receptacle, deagglomerate the formulation and deliver the formulation to the lungs using a wide range of patient inhalation flow rates. According to another aspect of the invention, devices and methods are provided which provide efficient delivery of a pharmaceutical aerosol to the deep lung.

According to the invention, the flow of respiratory gases may initially be prevented from flowing to the lungs until a predetermined vacuum is produced by the user, at which point the flow of respiratory gases is abruptly initiated. In one particular embodiment, the abrupt initiation of respiratory gas flow is utilized to aerosolize a pharmaceutical formulation. According to this embodiment, respiratory gases are initially prevented from flowing to the lungs when attempting to inhale through an open mouthpiece at one end of the device. The respiratory gases are then abruptly permitted to flow to the lungs after a predetermined vacuum is produced by the user. The flow of respiratory gases is utilized to extract a pharmaceutical formulation from a receptacle and to place the pharmaceutical formulation within the flow of respiratory gases to form an aerosol.

By initially preventing respiratory gases from flowing to the lungs when attempting to inhale, the devices and methods of the present invention provide a way to ensure that the resulting gas stream has sufficient energy to extract the pharmaceutical formulation from the receptacle. In one aspect, the flow of respiratory gases may initially be prevented from flowing to the lungs by placing a valve within an airway leading to the lungs and opening the valve to permit the flow of respiratory gases. According to the invention, the valve is opened when a threshold actuating vacuum caused by the attempted inhalation is exceeded. In this way, when the valve is opened, the resulting gas stream has sufficient energy to extract and aerosolize the pharmaceutical formulation.

In another embodiment, the invention provides an aerosolization device that comprises a housing defining an airway, and a coupling mechanism to couple a receptacle containing a pharmaceutical formulation to the airway. The device further includes a valve to prevent respiratory gases from flowing through the airway until a threshold actuating vacuum is exceeded. At such a time, the valve opens to permit respiratory gases to flow through the airway and to extract the pharmaceutical formulation from the receptacle to form an aerosol.

A variety of threshold valves may be employed to prevent gases from flowing through the airway as will be discussed in detail below. For example, the valve may comprise an occlusion member having an opening, and a pull through member that is pulled through the opening when the threshold actuating vacuum is produced. As one specific example, the occlusion member may comprise an elastically compliant membrane, and the pull through member may comprise a ball that is pulled through the membrane when the threshold vacuum has been achieved. In another aspect, the threshold actuating vacuum of the valve is in the range from about 20 cm $H_2O$ to about 60 cm $H_2O$. In one particular aspect, the valve is configured to be disposed within the receptacle. In this way, the valve may conveniently be manufactured along with the receptacle.

According to another aspect, the invention provides devices and methods for regulating the flow of respiratory gases to provide consistent airflow, independent of the breathing rate of the user. In another aspect, the system includes a regulation system to regulate the flow of respiratory gases through the airway after the valve has been opened. The combination of flow regulation with the threshold valve according to the present invention results in devices and methods for aerosol delivery that are effective in delivering the aerosolized formulation to the deep lung.

In still another aspect, the devices and methods of the invention may limit the flow of respiratory gases to a rate that is less than a certain rate for a certain time. For example, the flow rate may be limited to a rate that is less than about 15 liters per minute for a time in the range from about 0.5 second to about 5 seconds, corresponding to a volume in the range from about 125 mL to about 1.25 L. Regulation of the flow rate is advantageous in that it may increase systemic bioavailability of the active agent of certain pharmaceutical formulations via absorption in the deep lung as described generally in PCT Application No. PCT/U.S. 99/04654, filed Mar. 3, 1999 and in copending U.S. application Ser. No. 09/414,384, previously incorporated by reference.

A variety of techniques may be employed to limit or regulate the flow of respiratory gases. For example, feedback may be provided to the user when an excessive flow rate is produced to permit a user to adjust their inhalation rate. Examples of feedback which may be provided include audio feedback, including a whistle, visual feedback, such as indicator lights or a level meter, tactile feedback, such as vibration, and the like. As another alternative, the flow of respiratory gases may be controlled by regulating the size of an airway leading to the lungs. For example, an elastically compliant valve may be used to provide flow resistance based upon the flow rate through the device and limit the flow to a certain rate.

In one aspect, the device further includes a regulation system to regulate the flow of respiratory gases through the airway to a certain rate. For example, the regulation system may be configured to limit the flow to a rate that is less than about 15 liters per minute for a certain time or a certain inspired volume. A variety of flow regulators may be employed to regulate the flow of gases to a certain rate as will be discussed in detail below. For example, the flow regulator may comprise a valve that is constructed of an elastic element, such as a soft elastomer, that limits the flow to a certain rate while also preventing flow in the opposite direction. Such a valve may have an orifice that permits the flow of air through the valve in response to an applied vacuum, and one or more collapsible walls surrounding the orifice. In this way, an increased vacuum pressure level draws the walls toward each other, thereby reducing or closing the orifice area and providing a higher resistance or complete resistance to flow. For example such a valve may be placed in a parallel flow path. Once the flow rate becomes too great, the valve closes so that all air passing through the device must pass through the other flow path. By providing this flow path with a certain size, the flow of gases through the device may be kept below the threshold rate.

In another particular aspect, the regulation system may comprise a feedback mechanism to provide information on the rate of flow of the respiratory gases. For example, the feedback mechanism may comprise a whistle that is in communication with the airway and produces a whistling sound when the maximum flow rate is exceeded. In another alternative, the regulation system may comprise a restriction mechanism to limit the size of the airway. Conveniently, the restriction mechanism may be adjustable to vary the rate of flow of respiratory gases through the airway. The restriction mechanism may be adjusted manually or automatically, such as by the use of an elastically compliant material.

Optionally, an electronically governed, closed-loop control system may be provided to adjust the restriction mechanism. In one aspect, the control system is configured to limit the flow to a certain rate for a certain time or a certain inspired volume and then to sense and adjust the restriction mechanism to permit an increased flow of respiratory gases through the airway. In this manner, the flow rate of respiratory gases may be regulated to limit the flow to a certain rate for a certain time to facilitate proper delivery of the pharmaceutical formulation to the lungs. The control system may then be employed to adjust the restriction mechanism so that the user can comfortably fill their lungs with respiratory gases to deliver the pharmaceutical formulation to the deep lung. Use of the regulation system and control system according to the present invention is advantageous in that the device may be used with numerous users that have different inhalation flow rates, with the device regulating the flow of respiratory gases so that the pharmaceutical formulation is properly delivered to the lungs.

According to another aspect of the invention, after the flow rate has been limited for the desired amount of time or inhaled volume, the size of the airway may be increased to provide for an increased flow rate. This may be accomplished, for example, by opening another airway traveling through the device. In this way, the user may comfortably inhale without substantial resistance in order to fill the user's lungs with respiratory gases and carry the pharmaceutical formulation into the deep lung.

In an alternative aspect, the invention may optionally utilize a variety of flow integrators to permit an increased flow rate through the inhalation device after a certain amount of time to permit the user to comfortably fill their lungs at the end of the process. Such flow integrators may have one or more moving members that move based on the volume of flow through the device. In this way, when the initial (regulated) volume has been inhaled, the member has moved sufficient to open another gas channel to permit increased gas flow. Examples of flow integrators that may be used are discussed in detail below and include movable pistons, clutch mechanisms, gas filled bellows with a bleed hole, and the like.

The pharmaceutical formulation for use with the systems and methods of the present invention may be a liquid or powder formulation. In one aspect of the method, the pharmaceutical formulation comprises a powdered medicament. The flow of respiratory gases is used to deagglomerate the powder once extracted from the receptacle. Optionally, various structures may be placed into the airway to assist in the deagglomeration process.

In still yet another embodiment, the invention provides a receptacle that comprises a receptacle body defining a cavity that is enclosed by a penetrable access lid. The receptacle further includes a threshold valve that is coupled to the receptacle body. In one aspect, the threshold valve is configured to open when experiencing a vacuum of at least about 40 cm $H_2O$.

According to another aspect, the invention may also utilize a variety of techniques to ensure that the user properly positions their mouth over the mouthpiece during use of an aerosolization device. For example, a lip guard may be included on the mouthpiece to permit the user to place their lips adjacent the lip guard. As another example, the mouthpiece may include bite or other landmarks. Alternatively, one or more holes may be provided in the side of the mouthpiece. These holes must be covered by the lips in order to create a sufficient vacuum to operate the device. As a further example, the mouthpiece may have a circular-to-elliptical profile. The elliptical portion must be covered by the patient's mouth in order for a vacuum sufficient to actuate the device to be created.

These and other aspects of the present invention will be readily apparent to one of ordinary skill in the art in view of the drawings and detailed description that follows.

BRIEF DESCRIPTION OF THE DRAWINGS

FIG. 21 is a perspective view of yet another embodiment of an aerosolization device according to the invention.

FIG. 22 illustrates one particular embodiment of an aerosolization device according the invention capable of holding multiple drug packets.

FIG. 22A illustrates a clip for use with the aerosolization device of FIG. 22.

FIG. 23 illustrates yet another alternative embodiment of an aerosolization device according the invention.

FIG. 23A illustrates a mouthpiece cover of the aerosolization device of FIG. 23.

FIG. 24 illustrates a strip of receptacles that may be utilized within the aerosolization device of FIG. 23.

Figure 1:
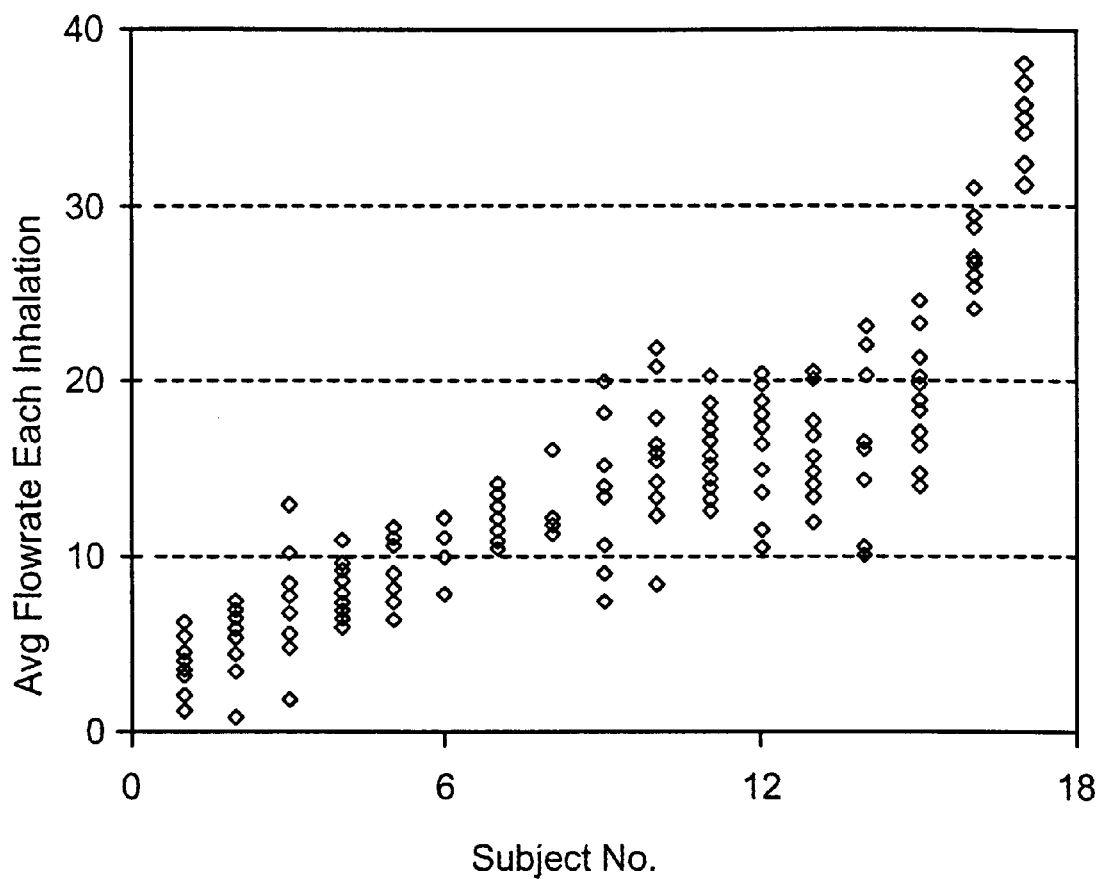
FIG. 1 is a graph illustrating the average inspiration flow rate for 17 individuals that were measured twice a week for four weeks.

Examples of active agents useful in this invention include but are not limited to insulin, calcitonin, erythropoietin (EPO), Factor VIII, Factor IX, ceredase, cerezyme, cyclosporine, granulocyte colony stimulating factor (GCSF), alpha-1 proteinase inhibitor, elcatonin, granulocyte macrophage colony stimulating factor (GMCSF), growth hormone, human growth hormone (HGH), growth hormone releasing hormone (GHRH), heparin, low molecular weight heparin (LMWH), interferon alpha, interferon beta, interferon gamma, interleukin-2, luteinizing hormone releasing hormone (LHRH), somatostatin, somatostatin analogs including octreotide, vasopressin analog, follicle stimulating hormone (FSH), insulin-like growth factor, insulintropin, interleukin-1 receptor antagonist, interleukin-3, interleukin-4, interleukin-6, macrophage colony stimulating factor (M-CSF), nerve growth factor, parathyroid hormone (PTH), thymosin alpha 1, IIb/IIIa inhibitor, alpha-1 antitrypsin, respiratory syncytial virus antibody, cystic fibrosis trans-membrane regulator (CFTR) gene, deoxyribonuclease (Dnase), bactericidal/perneability increasing protein (BPI), anti-CMV antibody, interleukin-1 receptor, 13-cis retinoic acid, pentamidine isethionate, albuterol sulfate, metaproterenol sulfate, beclomethasone dipropionate, triamcinolone acetamide, budesonide acetonide, ipratropium bromide, flunisolide, fluticasone, cromolyn sodium, ergotamine tartrate and the analogues, agonists and antagonists of the above. Active agents may further comprise nucleic acids, present as bare nucleic acid molecules, viral vectors, associated viral particles, nucleic acids associated or incorporated within lipids or a lipid-containing material, plasmid DNA or RNA or other nucleic acid construction of a type suitable for transfection or transformation of cells, particularly cells of the alveolar regions of the lungs. The active agents may be in various forms, such as soluble and insoluble charged or uncharged molecules, components of molecular complexes or pharmacologically acceptable salts. The active agents may be naturally occurring molecules or they may be recombinantly produced, or they may be analogs of the naturally occurring or recombinantly produced active agents with one or more amino acids added or deleted. Further, the active agent may comprise live attenuated or killed viruses suitable for use as vaccines.

"Mass median diameter" or "MMD" is a measure of mean particle size, since the powders of the invention are generally polydisperse (i.e., consist of a range of particle sizes). MMD values as reported herein are determined by centrifugal sedimentation, although any number of commonly employed techniques can be used for measuring mean particle size.

"Mass median aerodynamic diameter" or "MMAD" is a measure of the aerodynamic size of a dispersed particle. The aerodynamic diameter is used to describe an aerosolized powder in terms of its settling behavior, and is the diameter of a unit density sphere having the same settling velocity, generally in air, as the particle. The aerodynamic diameter encompasses particle shape, density and physical size of a particle. As used herein, MMAD refers to the midpoint or median of the aerodynamic particle size distribution of an aerosolized powder determined by cascade impaction.

DESCRIPTION OF THE SPECIFIC EMBODIMENTS

The invention provides systems and methods for the administration of aerosolized pharmaceutical formulations using the flow of respiratory gases produced by a patient. The pharmaceutical formulations that may be aerosolized include powdered medicaments, liquid solutions or suspensions, and the like, and may include an active agent. The devices of the present invention may be used for single or multiple administrations.

In some embodiments, the flow of respiratory gases produced by the patient is employed to extract the pharmaceutical formulation from a receptacle, to deagglomerate the pharmaceutical formulation and deliver the pharmaceutical formulation to the patient's lungs. One particular advantage of the invention is the ability to perform such functions independent of the patient's natural inhalation flow rate. Hence, in one aspect of the invention, the inhaled respiratory gases are controlled so that they remain within an acceptable range of flow rates to adequately deliver the pharmaceutical formulation to the lungs.

In another aspect, the invention is configured to regulate the flow of inspired gases so that the gases have sufficient energy to extract the pharmaceutical formulation from a receptacle, deagglomerate the formulation, and deliver it to the patient's lungs. In some cases, the invention is further configured to maintain the inhalation flow rate below a maximum level for at least a certain time or inhaled volume when initially delivering the drug. In this way, the aerosolized formulation will flow at an acceptable flow rate to enhance its ability to traverse the patient's airway and enter into the lungs. After initial delivery of the pharmaceutical formulation to the lungs, some embodiments of the invention may be configured to permit the patient to breath at a normal inspiration flow rate to fill the patient's lungs with respiratory gases and to further deliver the pharmaceutical formulation to the deep lung.

To aerosolize the pharmaceutical formulation, the flow of respiratory gases preferably contains sufficient energy to extract the pharmaceutical formulation from the receptacle. To ensure that the respiratory gases contain sufficient energy, the invention may be configured to prevent respiratory gases from flowing to the patient's lungs when the patient attempts to inhale. Abruptly, the respiratory gases may then be permitted to flow to the patient's lungs after a threshold vacuum has been reached. By abruptly permitting the flow of respiratory gases only when sufficient vacuum has been applied by the user, a relatively high rate of flow is achieved to provide the gas stream with sufficient energy. One way to accomplish such a process is by placing a restriction, valve, or other blocking mechanism in the patient's airway to prevent respiratory gases from entering the patient's lungs when the patient attempts to inhale. The restriction or valve may then be rapidly removed or opened to permit respiratory gases to flow to the lungs. Hence, a patient may be instructed to inhale until a threshold actuating vacuum is overcome. The threshold actuating vacuum may be configured such that it will produce sufficient energy in the resulting gas stream when the gases are allowed to flow to the patient's lungs. Preferably, the threshold vacuum is in the range from about 20 cm $H_2O$ to about 60 cm $H_2O$ so that the resulting gas stream will have sufficient energy to extract and deagglomerate the pharmaceutical formulation. Most preferably, the threshold vacuum is at least 40 cm $H_2O$.

A variety of threshold valves may also be employed to prevent respiratory gases from reaching the patient's lungs until a threshold inhalation vacuum is obtained. For example, the threshold valve may comprise an elastically compliant valve such as a flexible membrane that is disposed across the airway and is configured to flex when the threshold vacuum is met or exceeded. Alternatively, the threshold valve may comprise a scored membrane that is configured to tear or burst once the threshold vacuum is met or exceeded. As another example, the threshold valve may comprise an elastomer membrane having an opening. A ball is pulled through the opening once the threshold pressure has been met or exceeded. Other types of threshold valves include bi-stable mechanisms, diaphragms, and the like.

In one particular aspect of the invention, the threshold valve may be incorporated into a receptacle that also holds the pharmaceutical formulation. In this way, each time a new receptacle is inserted into an aerosolization device, the device is provided with a new threshold valve. This is particularly advantageous when the threshold valve comprises a membrane that is configured to tear or burst after the threshold vacuum is met or exceeded.

Once the respiratory gases are allowed to flow to the lungs, the flow rate of the respiratory gases (in some cases) may need to be controlled or regulated so that the gases do not exceed a maximum flow rate during delivery of the pharmaceutical formulation to the lungs. Typically, the flow rate of respiratory gases may be regulated to be less than about 15 liters per minute for a time in the range from about 0.5 seconds to about 5 seconds, corresponding to an inhaled volume in the range from about 125 mL to about 1.25 L, to permit the aerosolized formulation to pass through the patient's airway and enter into the lungs. For example, as previously illustrated in connection with FIG. 1, some patients have a natural inhalation rate that exceeds a desired maximum flow rate.

Figure 2:
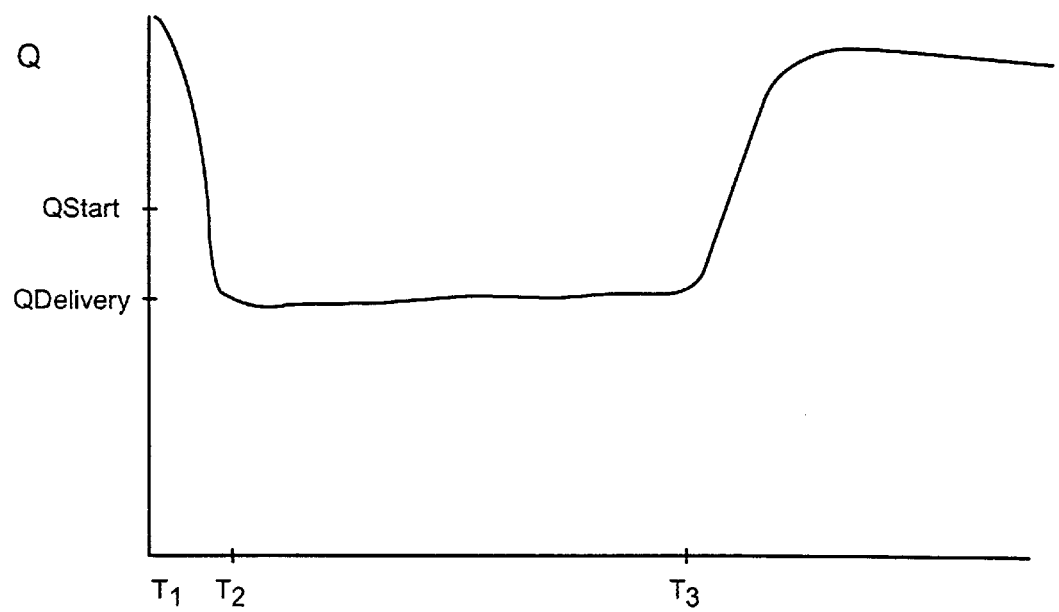
FIG. 2 is a graph illustrating the regulation of a patient's inspiration flow rate over time according to the invention.

For breathers that naturally breath above the maximum desired flow rate, the invention provides for the slowing of the flow rate during the time when the aerosolized formulation is being delivered to the lungs. This is illustrated graphically in FIG. 2. At time $T_1$, the patient is inhaling causing respiratory gases to flow to the patient's lungs. At time $T_1$, the flow rate is well above a starting flow rate, $Q_{START}$, which is desirable for initially extracting the pharmaceutical formulation from the receptacle as previously described. Hence, a threshold valve or other flow prevention mechanism may not be needed for such breathers. Shortly after time $T_1$ is time $T_2$, where the flow rate has been regulated to be below a $Q_{DELIVERY}$ flow rate. The flow rate is maintained below the $Q_{DELIVERY}$ rate from time $T_2$ to time $T_3$, where the aerosolized formulation is being delivered to the patient's lungs. After time $T_3$, the regulation of the gas flow is ceased and the patient is permitted to inhale at their regular flow rate to fill their lungs with respiratory gases that serve to further deliver the pharmaceutical formulation to the deep lung.

Figure 3:
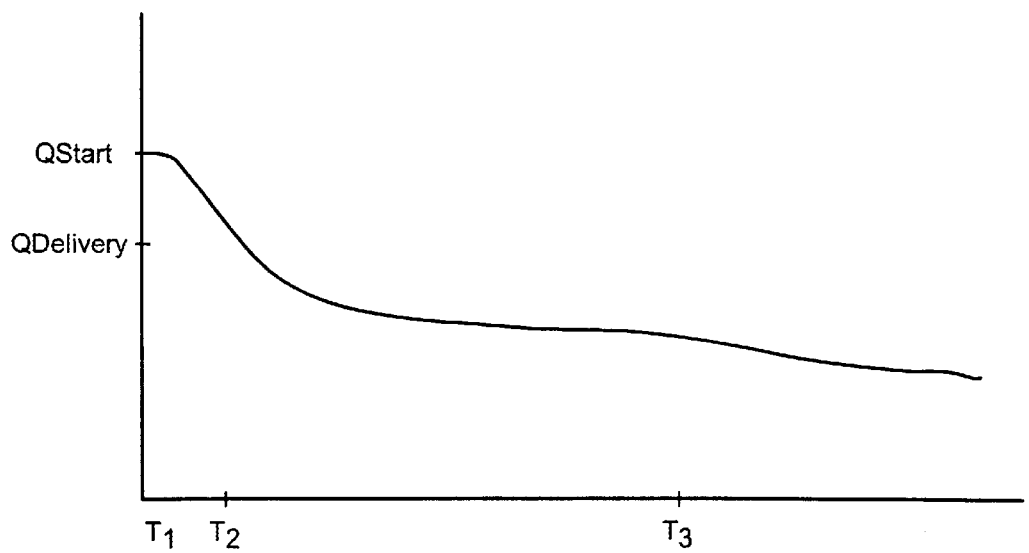
FIG. 3 is a graph illustrating the regulation of another patient's inspiration flow rate over time according to the invention.

FIG. 3 graphically illustrates an example of where the patient has a natural inhalation flow rate that is below $Q_{DELIVERY}$. As shown in FIG. 3, by preventing the flow of respiratory gases during patient inhalation, and then abruptly permitting the flow of respiratory gases, the starting flow rate at time $T_1$, is at $Q_{START}$. In this way, sufficient energy is provided to extract the formulation from the receptacle.

After the patient continues to inhale, the flow rate rapidly falls below the $Q_{DELIVERY}$ flow rate because the patient's natural inhalation flow rate is less than the $Q_{DELIVERY}$ flow rate. Hence, after time $T_1$, the patient's inhalation flow rate does not need to be regulated, thereby permitting the patient to inhale at a comfortable level.

A variety of schemes and techniques may be provided to regulate the inhalation flow rate to be below the $Q_{DELIVERY}$ flow rate from time $T_2$ to time $T_3$. As one example, the patient may be provided with various types of feedback to permit the patient to self-regulate their inhalation flow rate. For instance, an aerosolization device may be provided with a whistle that creates a whistling sound when the patient's flow rate exceeds the $Q_{DELIVERY}$ flow rate. Other types of feedback that may be utilized include visual feedback, tactile feedback, auditory feedback, and the like. Optionally, a controller may be provided with a timing mechanism to indicate to the user when time $T_3$ has elapsed so that the user may finish their inhalation at a comfortable level.

As another example, the patient's inhalation flow rate may be regulated by restricting or impeding the respiratory gases being inhaled. For example, the size of the airway may be varied to control the rate of flow of inspired gases. The manner of regulation may be either manual, semi-automated, or automated. For example, the user may manually adjust the size of the airway or place a restriction in the airway to control the rate of flow. Alternatively, the size of the airway may be adjusted based on the patient's own inhalation as described in greater detail hereinafter. In still another example, an automated system with one or more flow sensors may be provided to regulate the size of the airway to regulate the flow of respiratory gases.

One particular advantage of restricting the flow of respiratory gases to control the inhalation flow rate is that a relatively high pressure drop may be created. Because power is generally proportional to both the pressure drop and flow rate, the flow rate may be kept low while still providing sufficient energy to aerosolize the formulation and to deliver the formulation to the patient's lungs.

As another alternative, the flow of respiratory gases may be regulated by placing an orifice or other restriction member into the patient's airway that is made for use with a specific patient. In this way, an aerosolization device may be tailored to a specific patient simply by utilizing an orifice sized according to the patient's natural inhalation flow rate.

Figure 4:
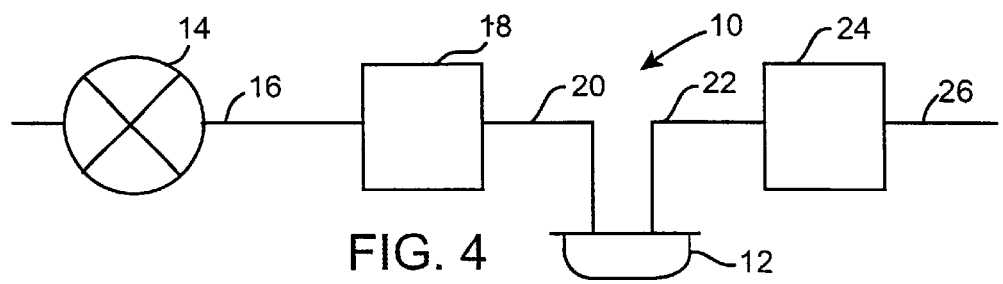
FIG. 4 is a schematic view of one system that may be utilized to extract a pharmaceutical formulation from a receptacle, deagglomerate the formulation and to place the formulation within the flow of respiratory gases to form an aerosol according to the invention.
Figure 70:
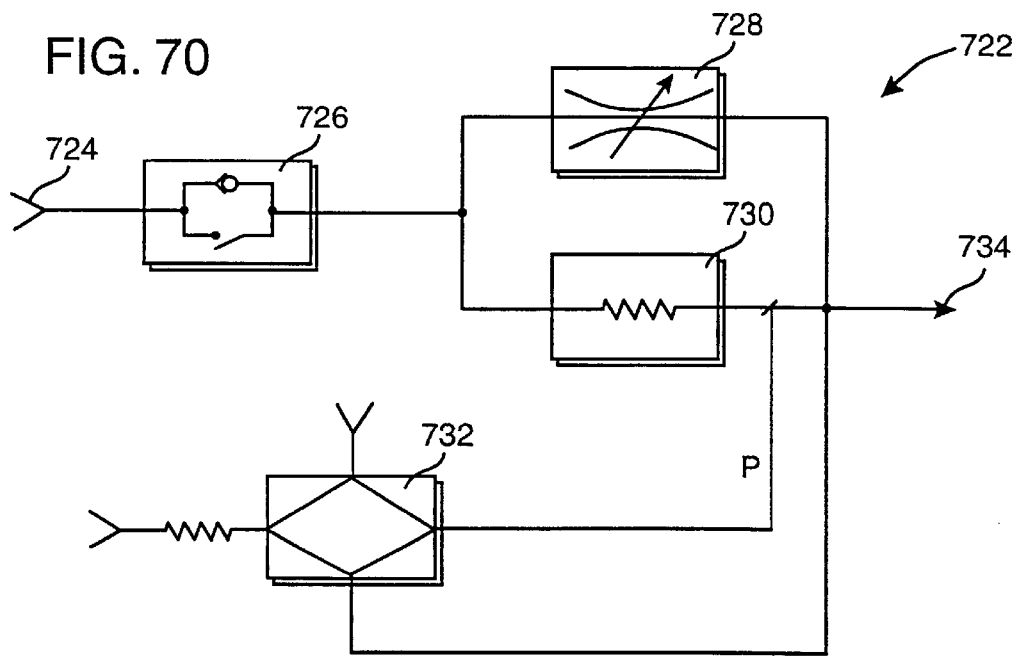
FIG. 70 schematically illustrates an aerosolization system having a parallel flow-by type the central nervous system. Suitable agents may be selected from, for example, polysaccharides, steroids, hypnotics and sedatives, psychic energizers, tranquilizers, anticonvulsants, muscle relaxants, antiparkinson agents, analgesics, anti-inflammatories, muscle contractants, antimicrobials, antimalarials, hormonal agents including contraceptives, sympathomimetics, polypeptides, and proteins capable of eliciting physiological effects, diuretics, lipid regulating agents, antiandrogenic agents, antiparasitics, neoplastics, antineoplastics, hypoglycemics, nutritional agents and supplements, growth supplements, fats, antienteritis agents, electrolytes, vaccines and diagnostic agents.
Figure 71:
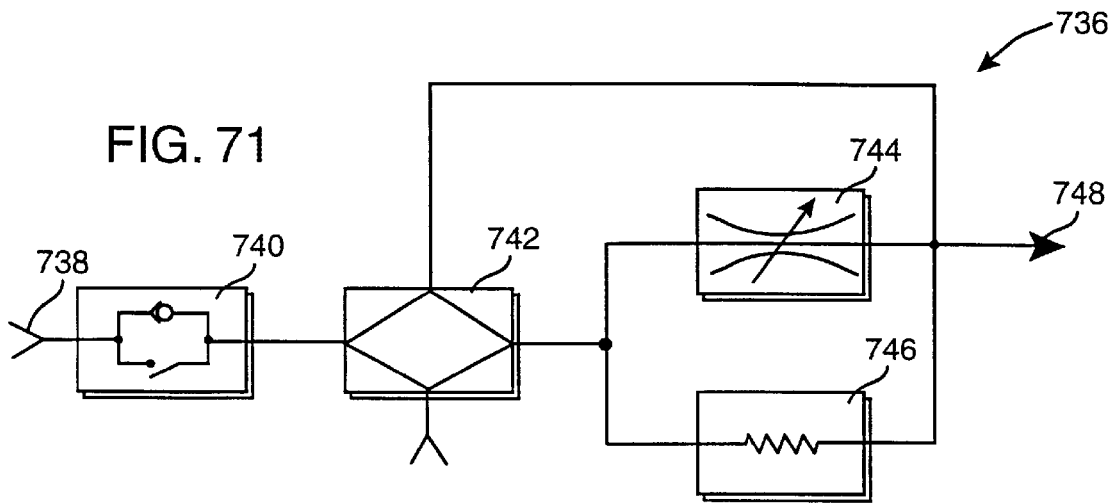
Figure 72:
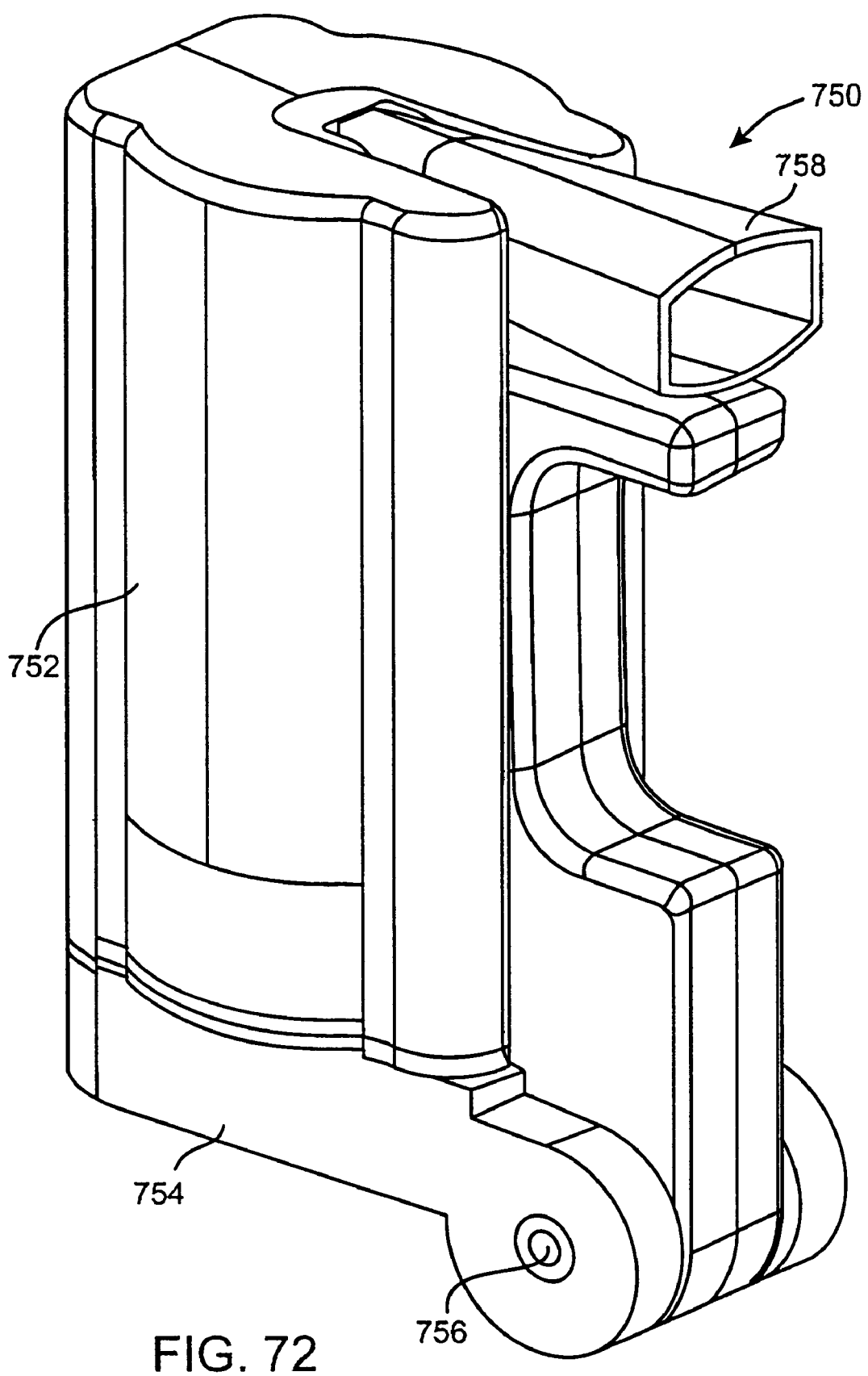
Figure 73:
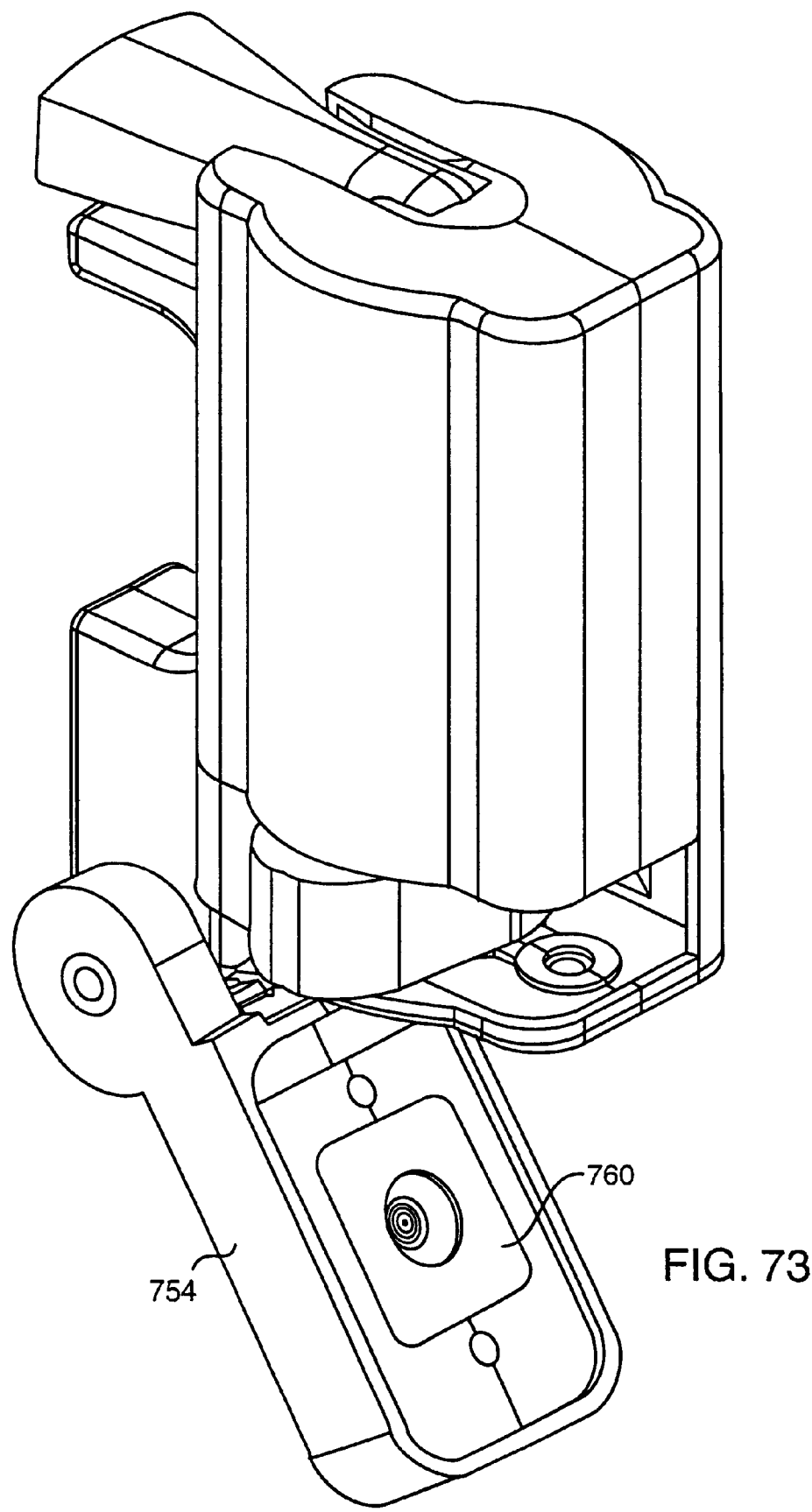
Figure 74:
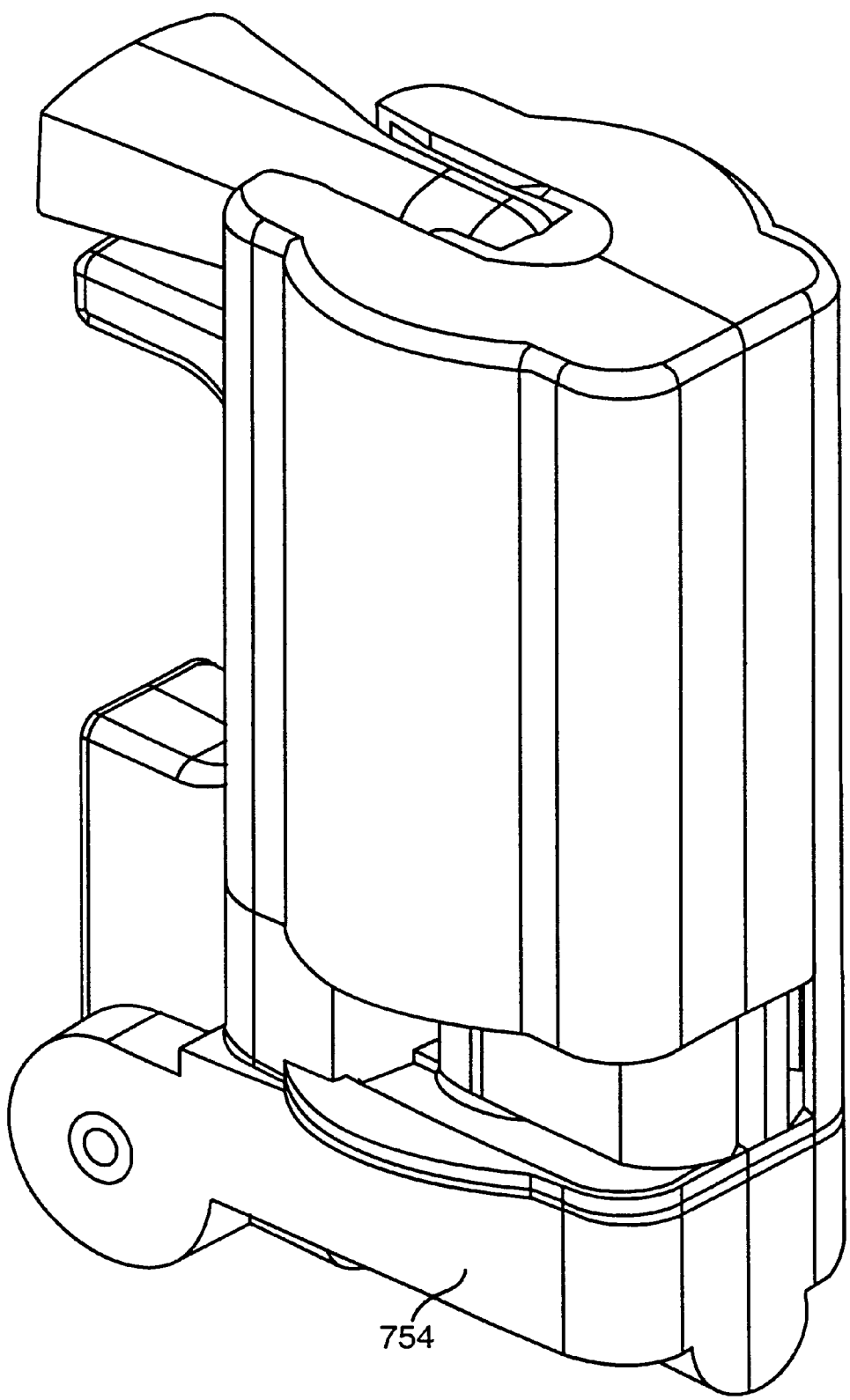
Figure 75:
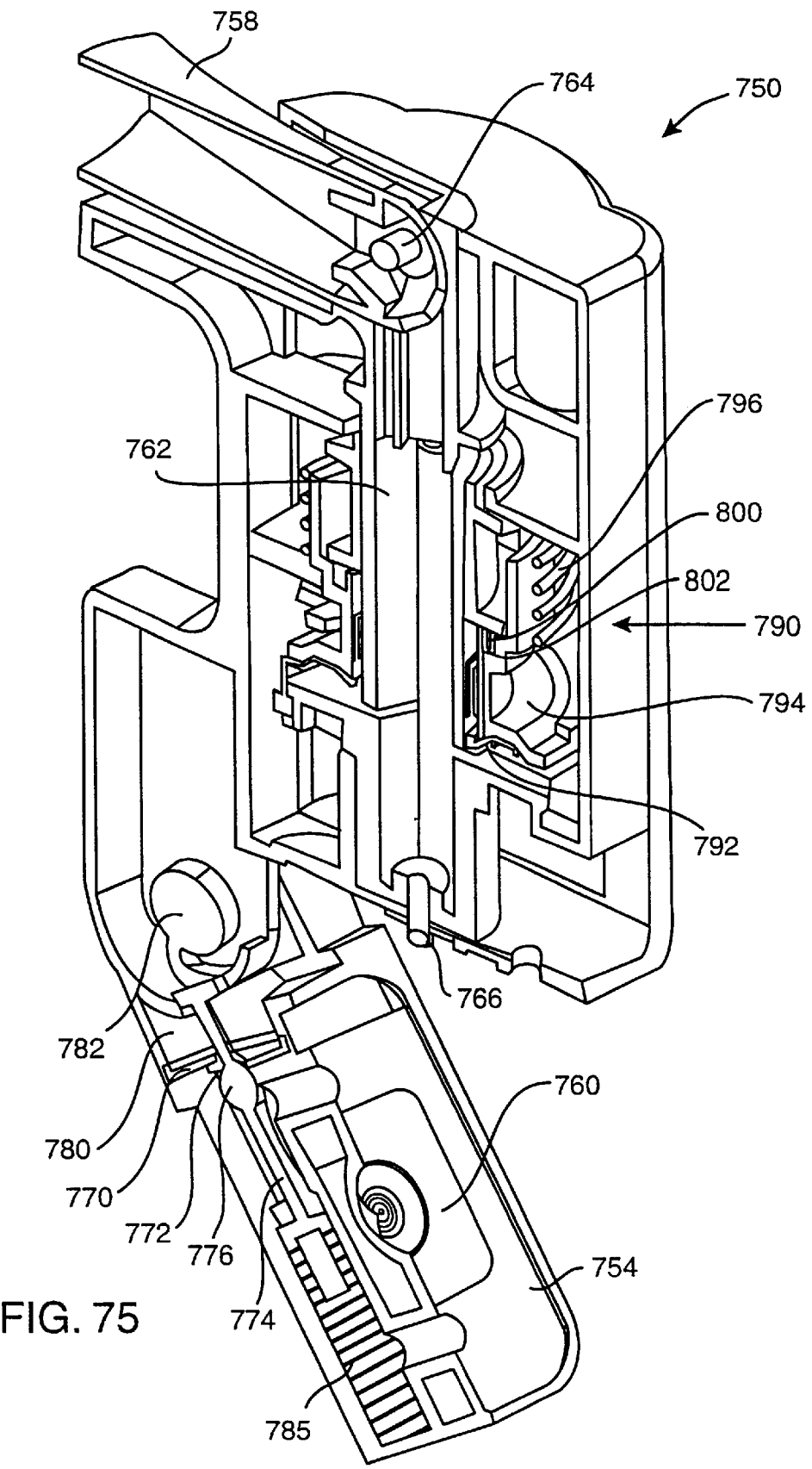
Figure 76:
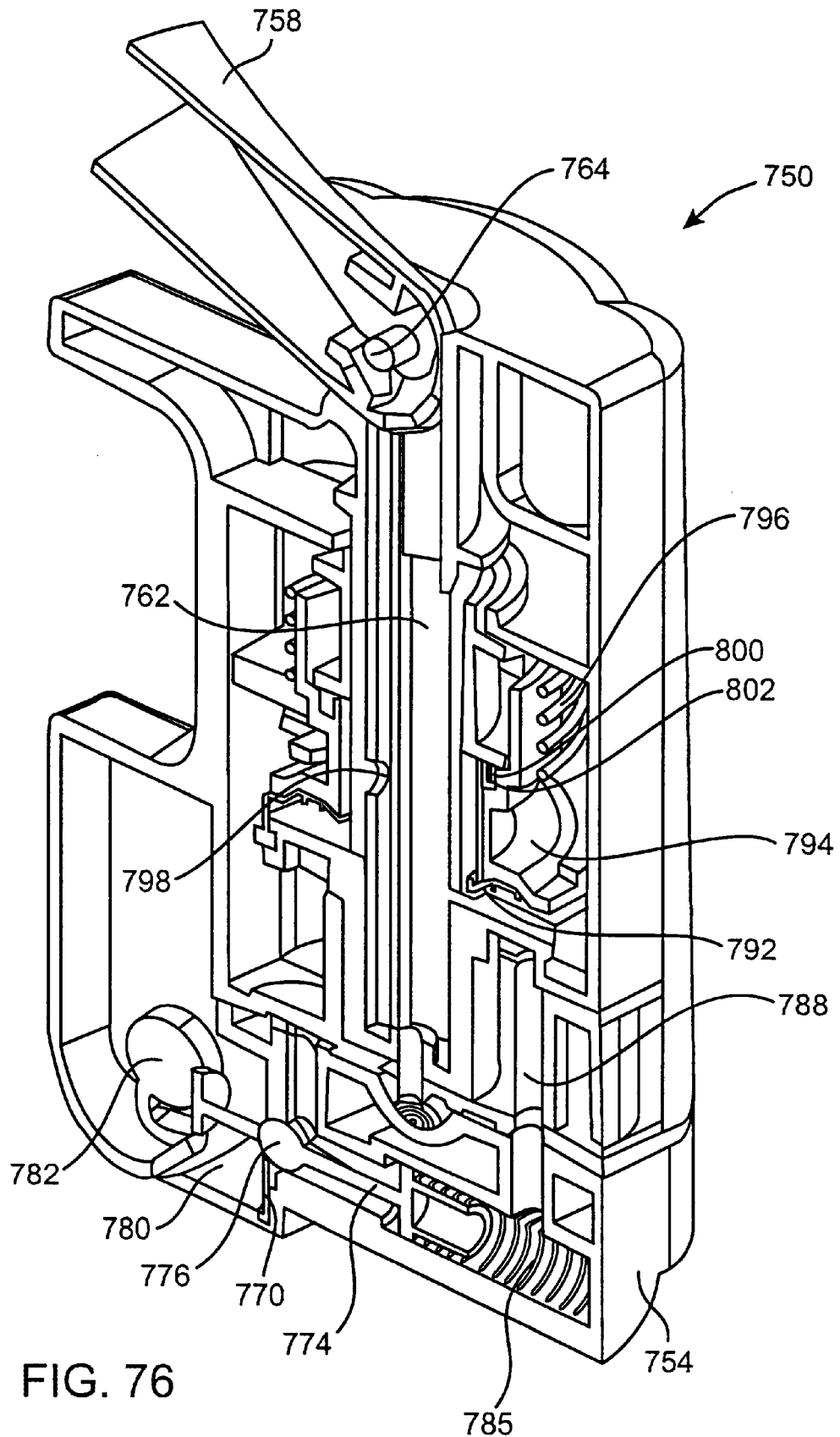
Figure 77:
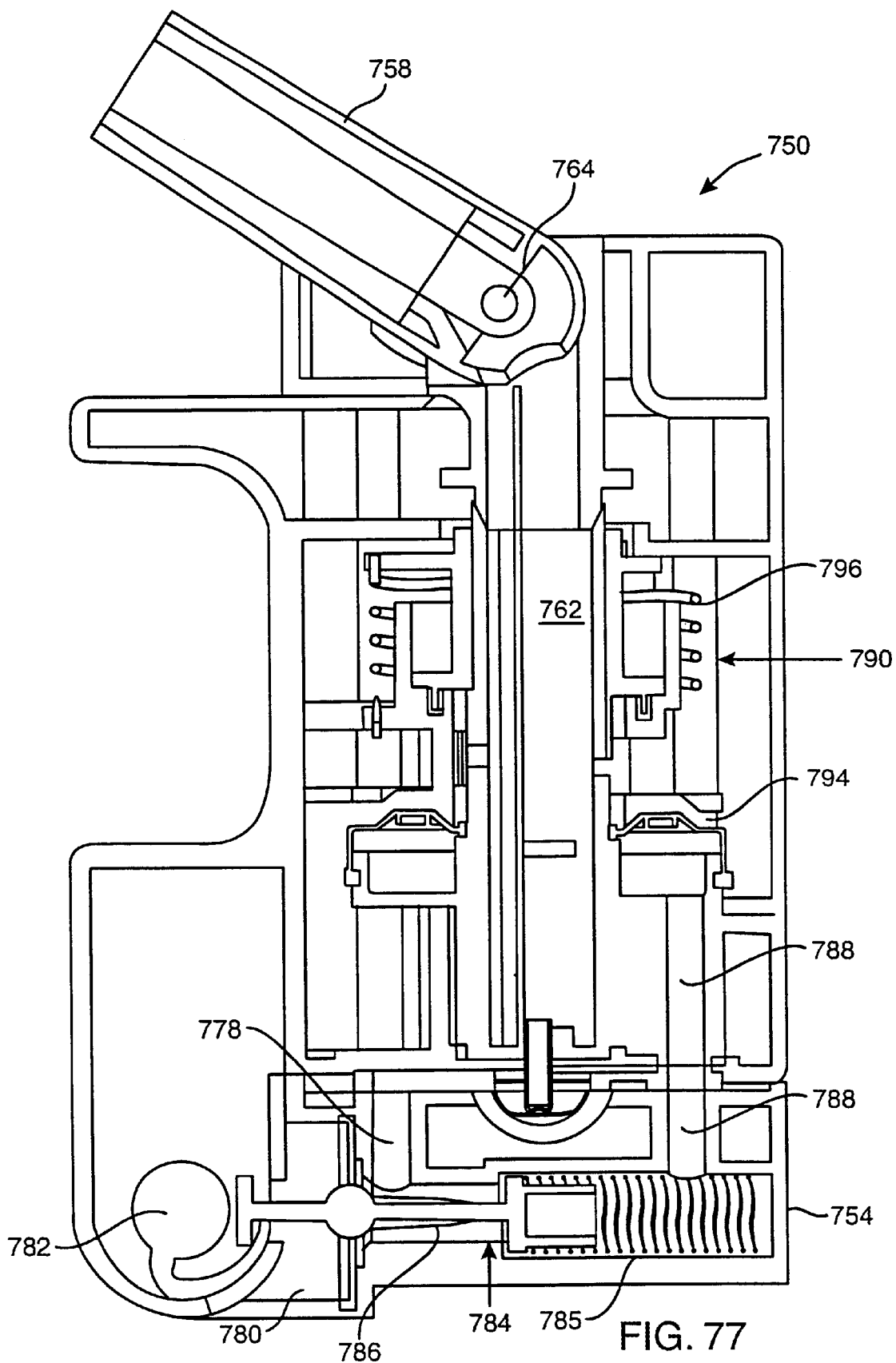
Figure 78:
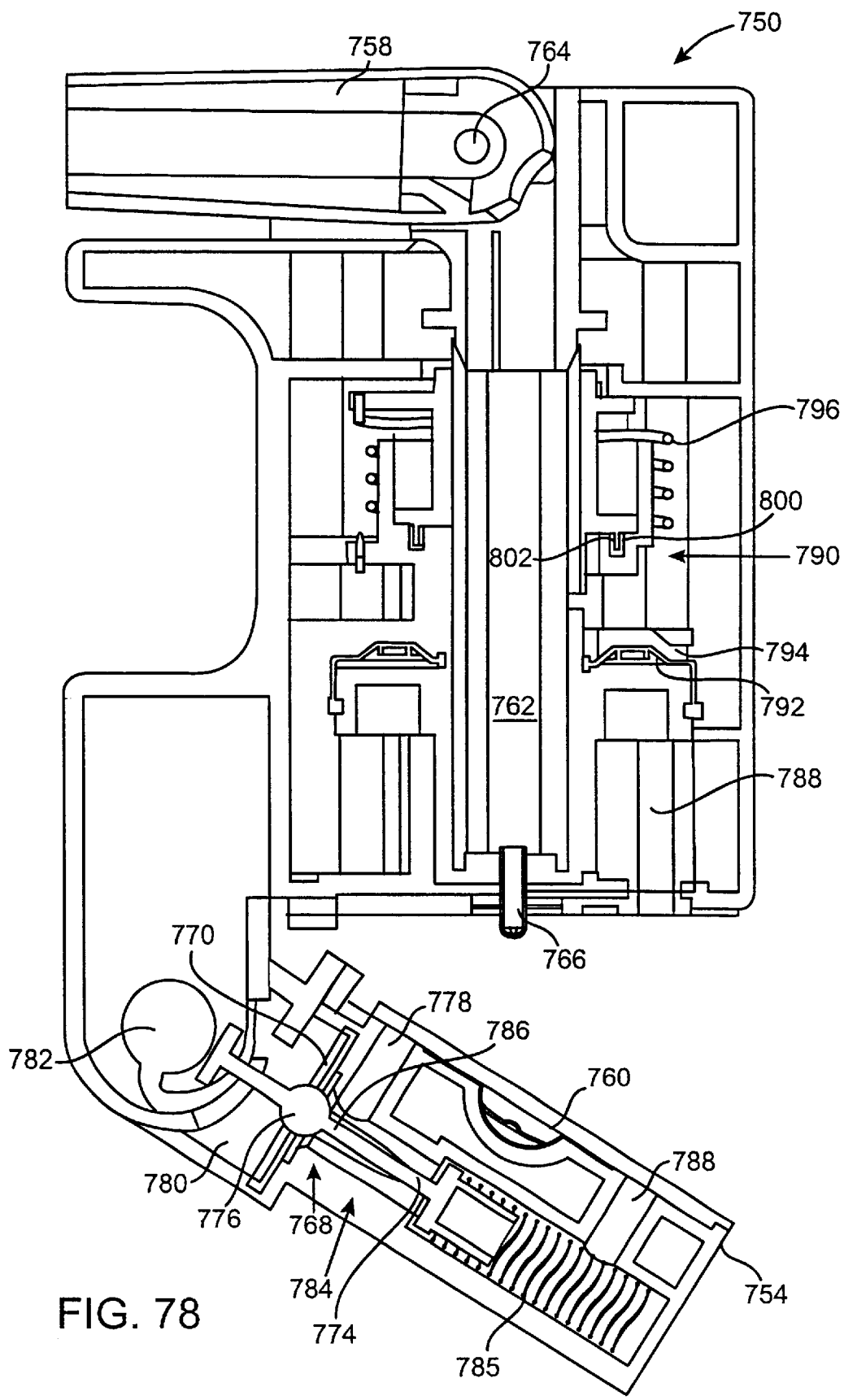
Figure 79:
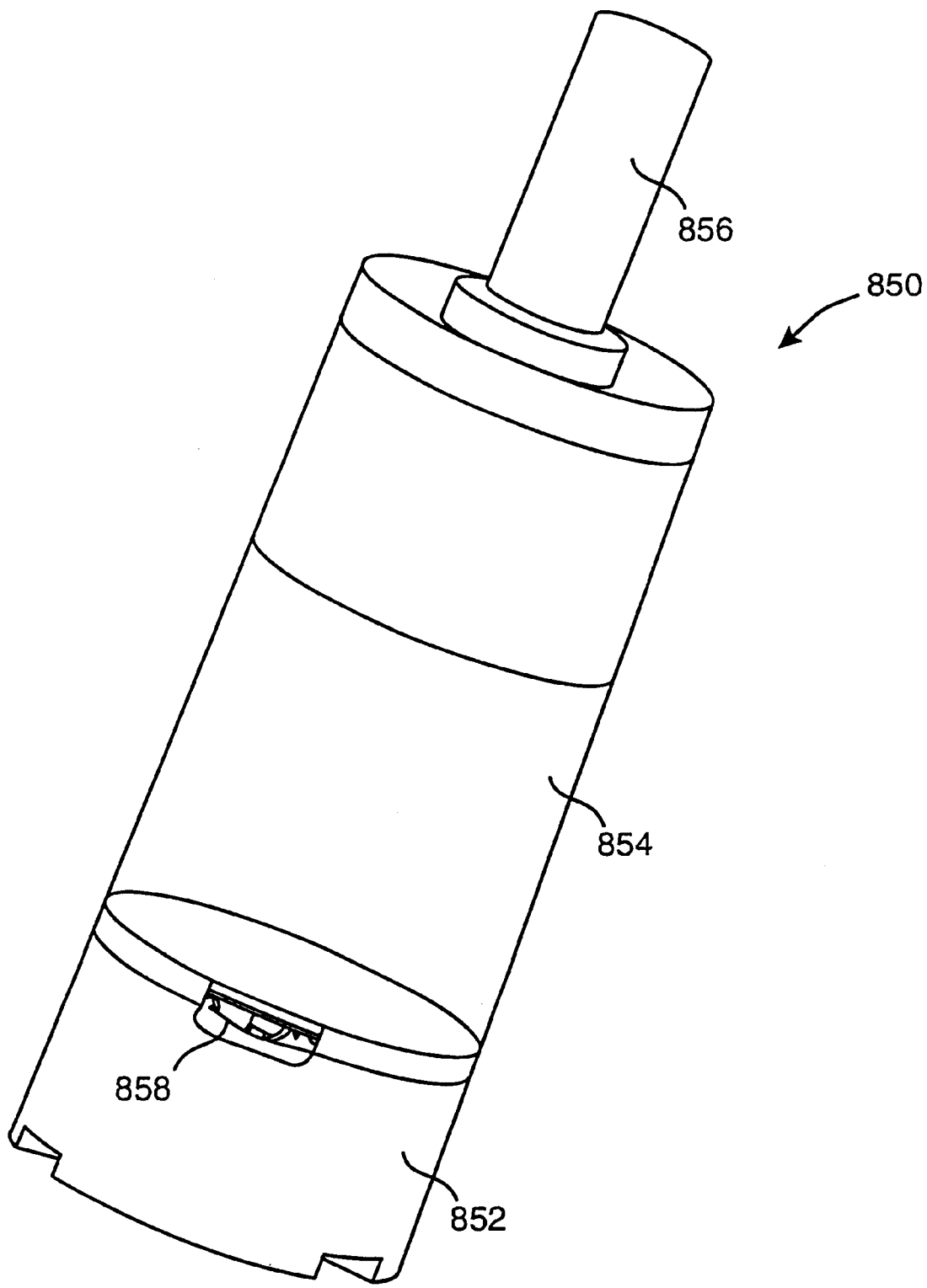

Devices according to the present invention may comprise series or parallel flowpaths. In either case, it may be desirable to maintain a constant, predetermined flow rate across a large patient population. For series constructs, as depicted in FIG. 4, it is preferred that the flow resistance/vacuum relationship is substantially linear. For parallel constructs, as shown in FIG. 70 for example, it is preferable to provide that the flow resistance/vacuum relationship is highly nonliner.

Referring now to FIG. 4, a system 10 utilizing a series construct for extracting a powdered medicament from a receptacle 12 using a patient's inspired respiratory gases will be described. System 10 comprises a threshold valve 14 that may be configured to open when the vacuum within a line 16 downstream of threshold valve 14 experiences a vacuum of within 20–60 cm $H_2O$, preferably greater than about 40 cm $H_2O$. Also coupled to line 16 is a regulation system 18 that regulates the flow of respiratory gases through system 10. As one example, regulation system 18 may include a restriction mechanism that may be employed to control the internal size of line 16 and thereby regulate the flow of respiratory gases through line 16. Conveniently, regulation system 18 may include a control system that adjusts the restriction mechanism. The control system may be either manually operated or operated in an automated manner using a controller. For example, gas flow sensors may be disposed in system 10 and coupled to the controller to determine the rate of flow of respiratory gases through the system. Using this information, the controller may be employed to control the degree of restriction of line 16. Although regulation system 18 is shown upstream of receptacle 12, it will be appreciated that regulation system 18 may be provided in other locations, including downstream of receptacle 12 and upstream of threshold valve 14.

Regulation system 18 is coupled to receptacle 12 by a line 20. Exiting receptacle 12 is a line 22 that is in communication with a deagglomeration mechanism 24. In this way, powder extracted from receptacle 12 may be deagglomerated before leaving system 10 and passing into the patient's lungs. Exiting deagglomeration mechanism 24 is a line 26 that may be coupled to a mouthpiece (not shown) from which the patient inhales. Hence, with system 10, a patient may receive a dose of an aerosolized medicament by inhaling from the mouthpiece until the patient produces a vacuum sufficient to open threshold valve 14. When threshold 14 opens, the powdered medicament is extracted from receptacle 12 and passes through deagglomeration mechanism 24. At the same time, regulation system 18 controls the flow of respiratory gases within an acceptable rate so that the aerosolized medicament may properly pass into the patient's lungs. After a certain amount of time, the regulation system 18 may be configured to cease operating so that the patient may inhale at a comfortable rate to fill the lungs with respiratory gases and to move the delivered medicament to the deep lung.

Figure 5:
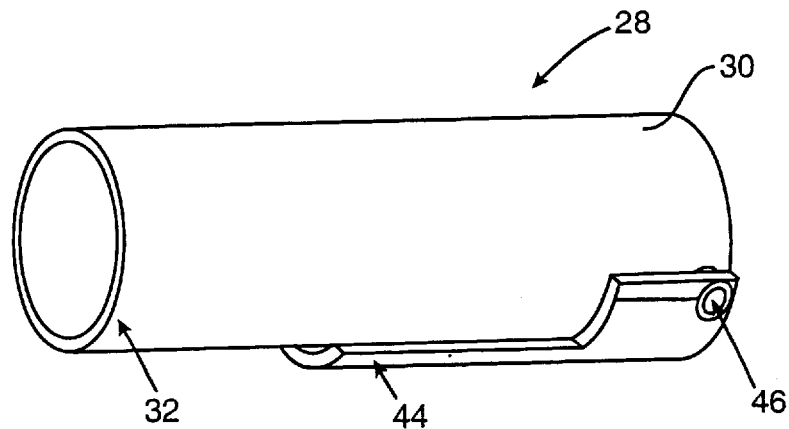
FIG. 5 is a perspective view of an aerosolization device according to the invention.

Referring now to FIG. 5, an exemplary embodiment of an aerosolization device 28 will be described. Device 28 comprises a generally cylindrical housing 30 having a mouthpiece 32 at one end. Housing 30 further includes openings 34, 36 and 38 which define a flow path for respiratory gases as described in greater detail hereinafter. Conveniently, a divider 40 is provided between openings 36 and 38 to permit the flow of respiratory gases to pass temporarily outside of housing 30. Similarly, a divider 42 is provided to facilitate the introduction of respiratory gases into housing 30 through opening 34 (see FIG. 6).

Figure 6:
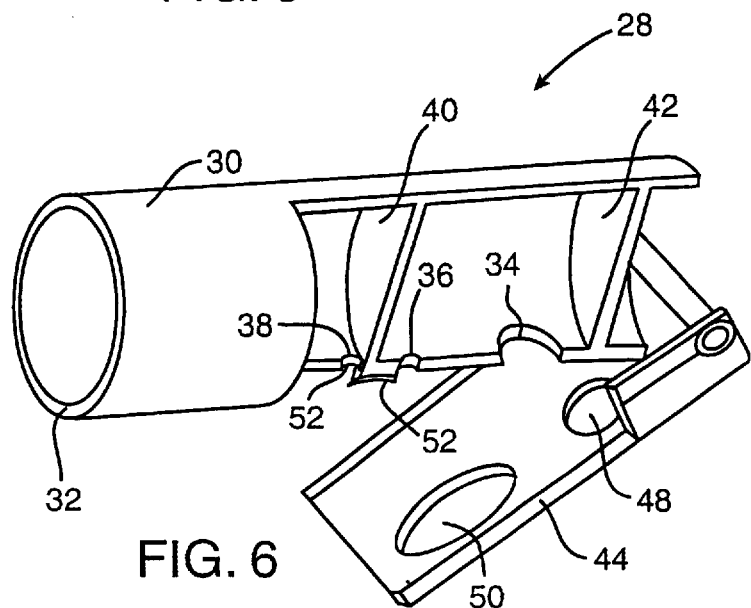
FIG. 6 is a partial cutaway view of the aerosolization device of FIG. 5 shown in an open or loading position.
Figure 7:
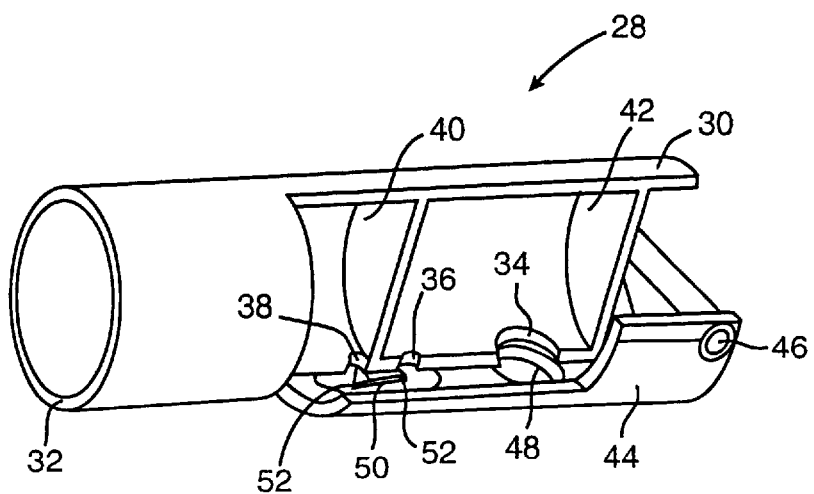
FIG. 7 illustrates the aerosolization device of FIG. 6 in a closed or operating position according to the invention.

Pivotally coupled to housing 30 is a receptacle carrier 44. Conveniently, a pin 46 is employed to pivotally couple carrier 44 to housing 30. In this way, carrier 44 may be moved to an open position as shown in FIG. 6 to permit a receptacle to be loaded into device 28. Carrier 44 may then be moved to a closed or operating position as shown in FIG. 7. As best shown in FIGS. 6 and 7, carrier 44 includes an opening 48 that is aligned with opening 34 when carrier 44 is moved to the closed position. Carrier 44 further includes another opening 50 that is positioned below two penetrating tabs 52 on housing 30.

Figure 8:
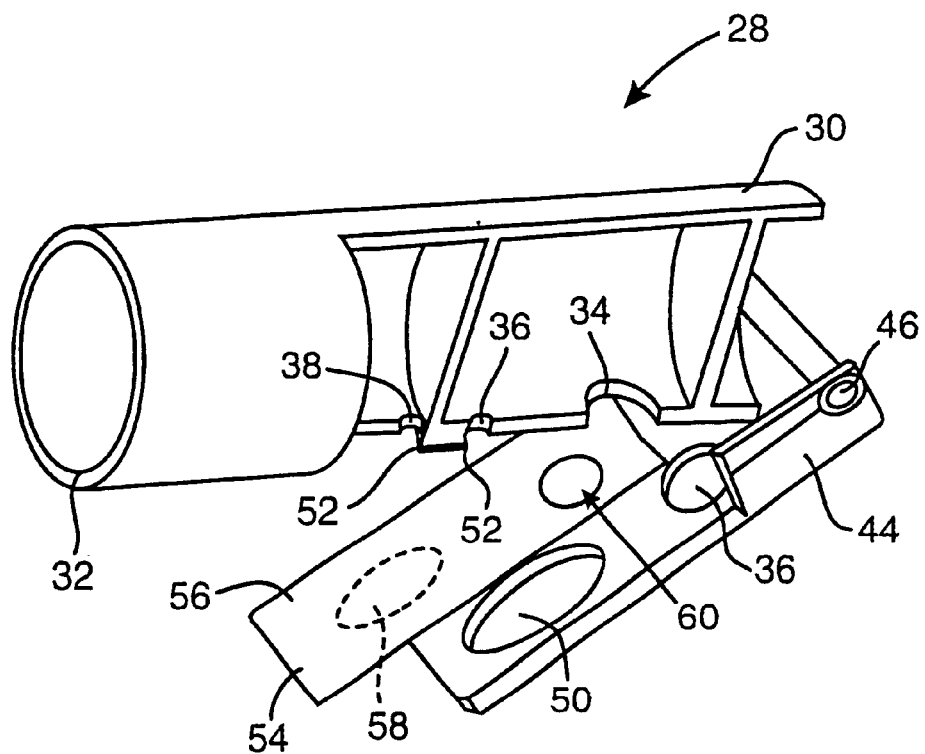
FIG. 8 illustrates the aerosolization device of FIG. 6 when inserting a receptacle according to the invention.

As best shown in FIG. 8, once carrier 44 is moved to the open position, a receptacle 54 may be inserted into device 28. Receptacle 54 comprises a receptacle body 56 having a chamber 58 (shown in phantom line) which holds the powdered medicament. Receptacle body 56 is configured so that the portion above chamber 58 is penetrable by tabs 52 as described in greater detail hereinafter. Disposed in receptacle body 56 is a threshold valve 60 that comprises a membrane that is configured to rupture or tear at a specified threshold vacuum.

Figure 9:
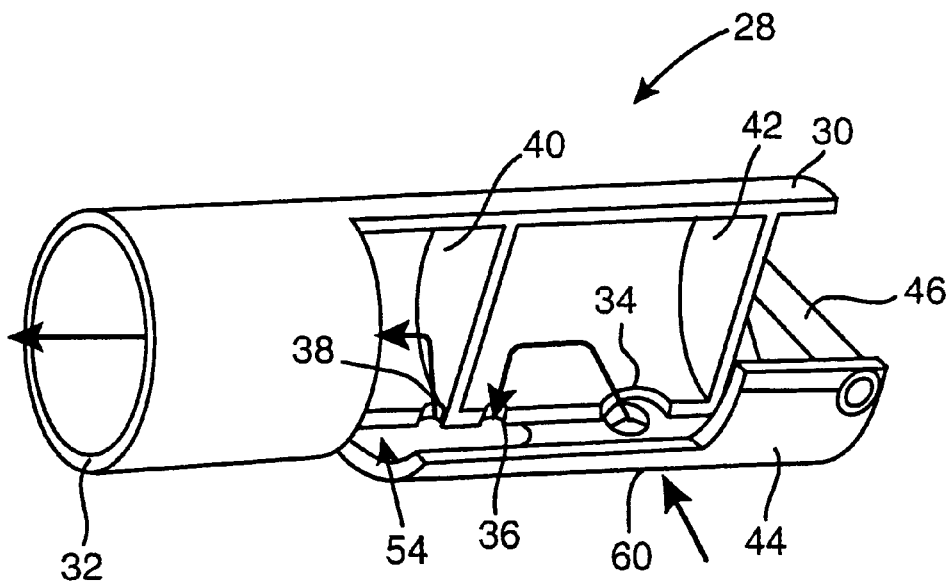
FIG. 9 illustrates the aerosolization device of FIG. 8 when the receptacle has been inserted, when the device has been moved to the closed or operating position, and when respiratory gases are flowed through the device.

Receptacle 54 is inserted into device 28 so that threshold valve 60 is aligned with opening 36. Also, chamber 58 rests within opening 50. Once receptacle 54 is inserted onto carrier 44, carrier 44 is moved to the closed or operating position as illustrated in FIG. 9. When in the closed position, threshold valve 60 is aligned with opening 34. Further, tabs 52 penetrate body 56 over chamber 58 and peel back the lid to provide a pair of openings that provide access to the powder contained within chamber 58. Once carrier 44 is moved to the closed position, a user may place his mouth over mouthpiece 32 and attempt to inhale. The flow of respiratory gases through device 28 is prevented until the user creates sufficient vacuum to open threshold valve 60. At this point, respiratory gases are abruptly permitted to flow through opening 34, through opening 36, through chamber 58, through opening 38 and out mouthpiece 32 as illustrated by the arrows.

Figure 10:
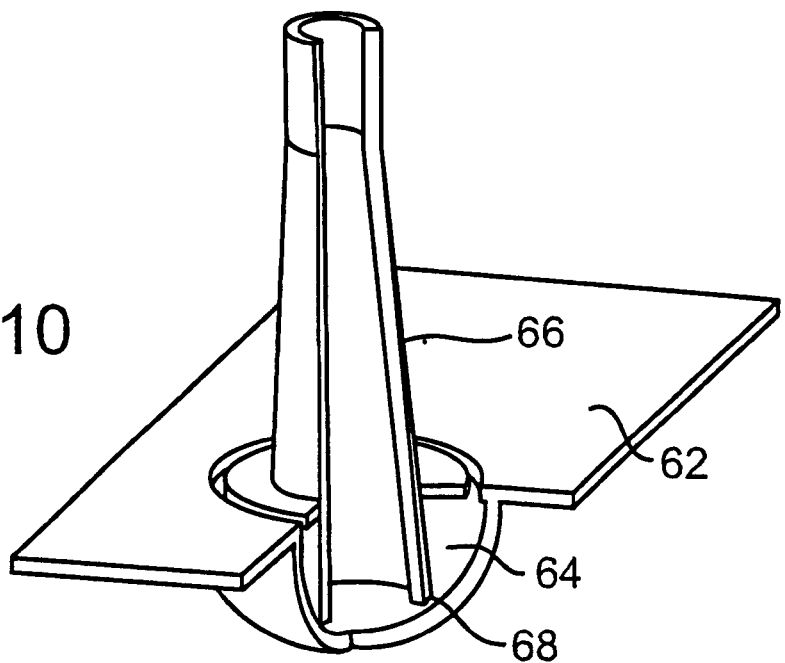
FIG. 10 is a partial cutaway perspective view of a receptacle and a convergent nozzle through which a pharmaceutical formulation may be extracted according to the invention.
Figure 11:
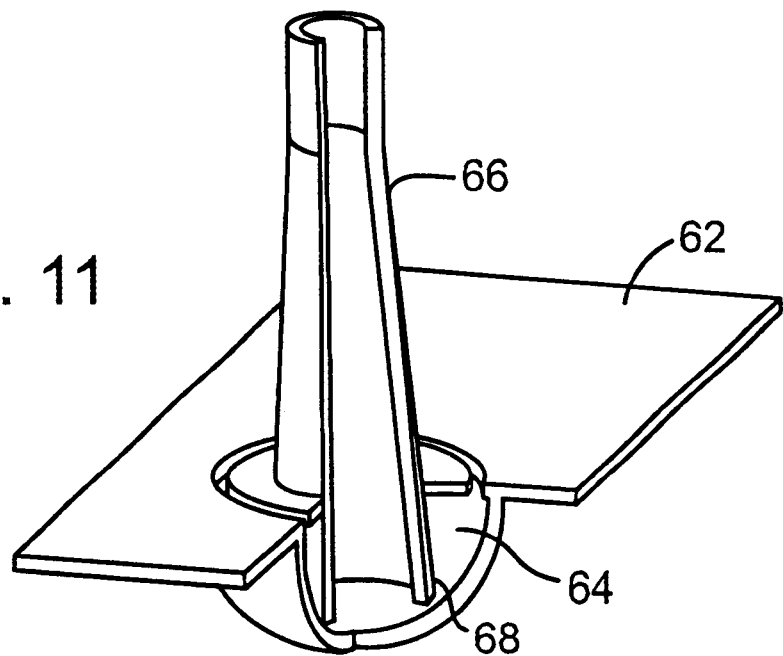
FIG. 11 illustrates the receptacle and nozzle of FIG. 10, with the nozzle being moved further away from a bottom end of the receptacle to increase the rate of flow of respiratory gases through the nozzle according to the invention.

Turning now to FIGS. 10 and 11, an example of one technique that may be employed to regulate the flow of respiratory gases through an aerosolization device, such as device 28, will be described. Shown in FIG. 10 is a receptacle 62 having a chamber 64 that is typically filled with a pharmaceutical formulation (not shown). In FIG. 10, a penetrating tube 66 has already penetrated the lid over chamber 64, and a distal end 68 of tube 66 is disposed within chamber 64. In FIG. 10, distal end 68 of tube 66 is positioned near the bottom of chamber 64. In this way, the airway between distal end 68 and the bottom of chamber 64 is reduced in size to restrict the respiratory gases flowing into chamber 64 and out penetrating tube 66. As shown in Fig. 11, distal end 68 is moved vertically upward so that it is further distanced from the bottom end of chamber 64. In this way, the flow rate of respiratory gases may be increased.

A variety of techniques may be employed to adjust the distance between distal end 68 and the bottom of chamber 64. For example, one technique is to employ the use of a suction force created by patient inhalation. More specifically, as the patient begins to inhale, the vacuum source created within tube 68 by the inhalation will tend to move the bottom end of chamber 64 toward distal end 68. Various mechanisms may then be employed to control the distance between distal end 68 and the bottom end of chamber 64. For example, a variety of biasing mechanisms may be included to control the relative movement between receptacle 62 and penetrating tube 66. Automated mechanisms, such as solenoids, pistons, and the like may also be employed. Further, various manual techniques may also be used, including utilization of the user's hands or fingers.

One feature of penetrating tube 66 is that it forms a convergent nozzle that serves as a deagglomerator for the power contained within chamber 64. More specifically, as the patient inhales to extract the powder from chamber 64, the convergent low path created by penetrating tube 66 tends to deagglomerate the powder to facilitate its aerosolization and deposition within the lung.

Figure 12:
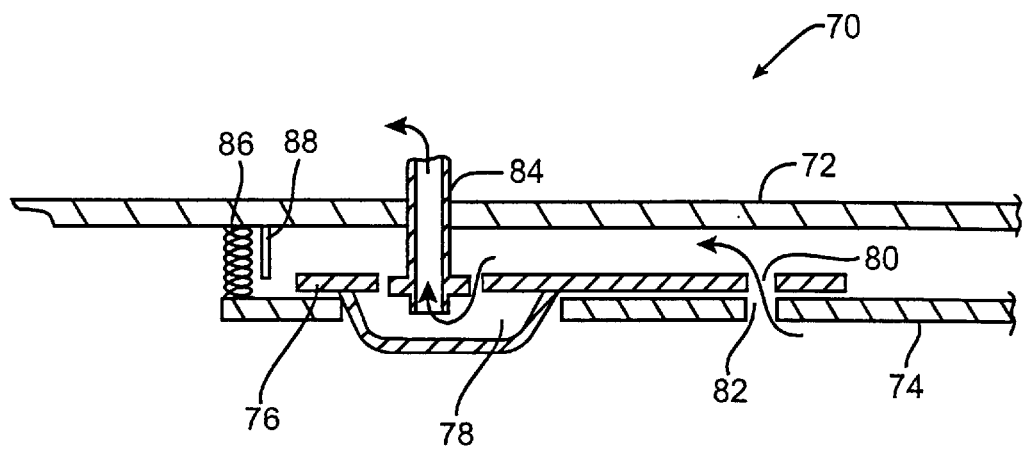
FIG. 12 is a schematic, cross-sectional side view of an aerosolization system having a spring to regulate the flow of respiratory gases through the system according to the invention.

Referring now to FIG. 12, an embodiment of an aerosolization device 70 will be described to illustrate one technique for regulating the flow of respiratory gases through the device. For convenience of illustration, only a portion of device 70 is illustrated, it being appreciated that other components may be utilized to complete the device. Aerosolization device 70 comprises a housing 72 and a receptacle carrier 74. Receptacle carrier 74 may be configured to be movable relative to housing 72 for convenient loading and unloading of a receptacle 76. Receptacle 76 includes a chamber 78 and a threshold valve 80 that may be constructed to be similar to other embodiments described herein. Receptacle carrier 74 includes an opening 82 that is aligned with valve 80 to permit respiratory gases to flow through valve 80 once opened. Coupled to housing 72 is a penetrating tube 84 that penetrates receptacle 76 to provide access to chamber 78 in a manner similar to that described with the previous embodiments. In this manner, when a patient inhales from device 70, threshold valve 80 opens when the threshold vacuum is overcome. Respiratory gases then flow through chamber 78 and out penetrating tube 84 as illustrated by the arrows.

Device 70 further includes a spring 86 disposed between housing 72 and receptacle carrier 74. Once valve 80 is opened, the vacuum within penetrating tube 84 causes the bottom end of chamber 78 to be drawn toward penetrating tube 84. The spring constant of spring 86 may be selected to control the distance between the bottom end of chamber 78 and penetrating tube 84 to regulate the gas flow through the device. In some cases, it may be desirable to select the spring constant of spring 86 based on the average inhalation flow rate produced by the patient. In this way, device 70 may be tailored to a particular patient. Device 70 further includes a pin 88 that maintains the spacing between the bottom of chamber 78 and penetrating tube 84 to a certain distance. In this way, chamber 78 will not completely be drawn against penetrating tube 84.

Figure 13:
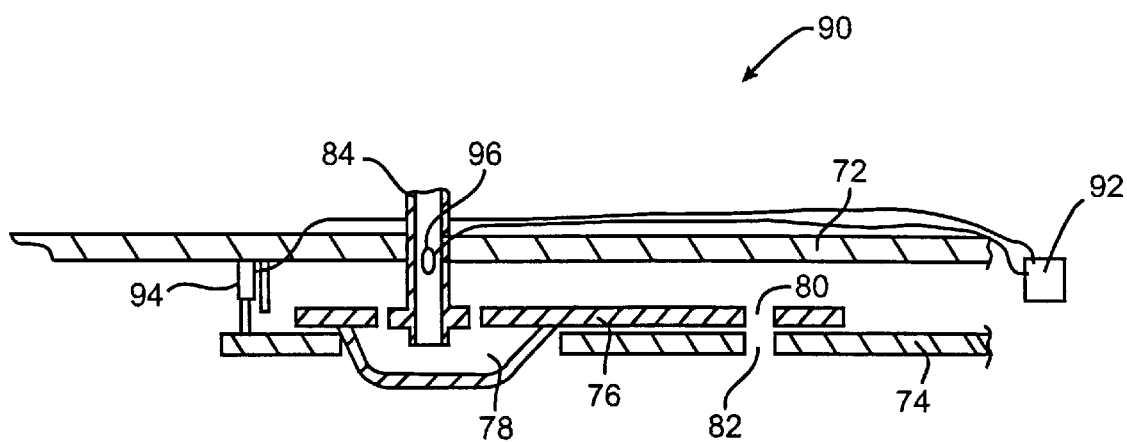
FIG. 13 is a schematic, cross-sectional view of an aerosolization system having a flow regulation system to regulate the flow of respiratory gases through the aerosolization system according to the invention.

Referring now to FIG. 13, an aerosolization device 90 will be described. Device 90 may be constructed from elements similar to that previously described in connection with aerosolization device 70. Hence, for convenience of discussion, similar elements used for aerosolization device 90 will be referred to with the same reference numerals used to describe device 70 and will not be described further. Aerosolization device 90 differs from aerosolization device 70 in that it employs an electronic controller 92 to control the distance between penetrating tube 84 and the bottom end of chamber 78. Controller 92 is electronically coupled to a solenoid 94 that may be extended or retracted to control the spacing between penetrating tube 84 and chamber 78. Optionally, a flow control sensor 96 may be disposed anywhere within the airway of device 90 to sense the rate of flow through the device. When controller 92 receives a signal from sensor 96, it may send a signal to solenoid 94 to adjust the spacing to thereby regulate the flow rate. One advantage of using controller 92 is that it may also include a timing circuit so that solenoid 94 may be fully extended after a certain amount of time. In this way, once the aerosolized formulation has reached the patient's lungs, solenoid 94 may be fully extended to permit the user to comfortably inhale without substantial resistance to fill their lungs with respiratory gases.

Figure 14:
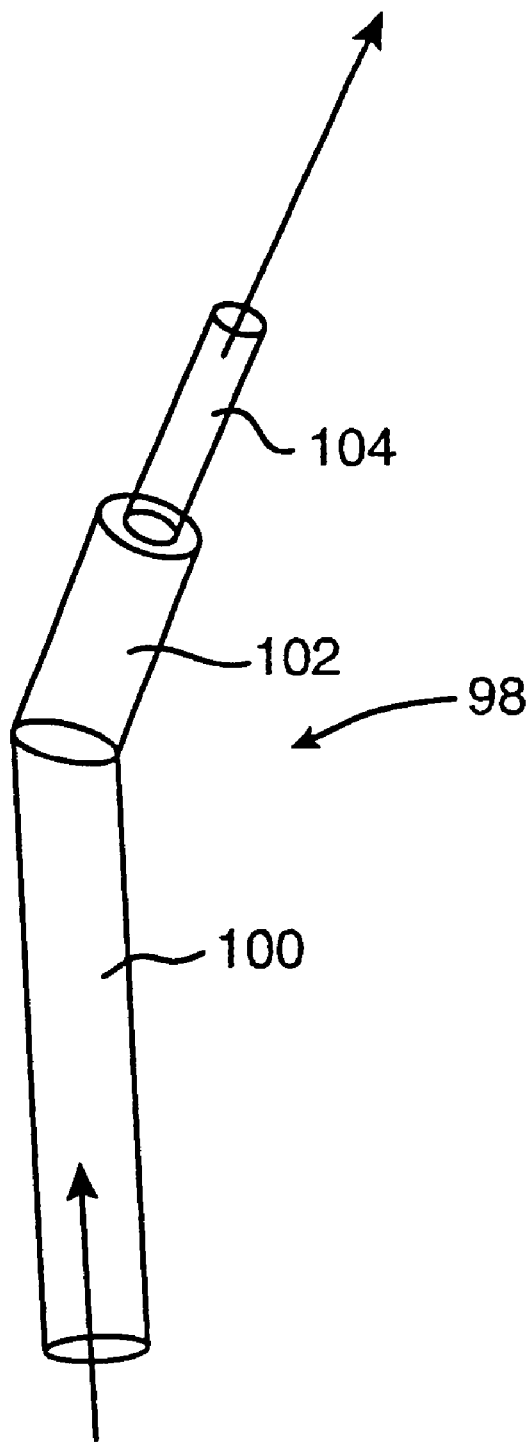
FIG. 14 illustrates one embodiment of a nozzle that may be employed to deagglomerate a pharmaceutical formulation according to the invention.

Referring now to FIG. 14, another embodiment of a nozzle 98 that may be placed downstream of a receptacle will be described. Nozzle 98 comprises a tubular structure 100 having a bent section 102 and a contracted section 104. As the pharmaceutical formulation is extracted from the receptacle, it passes through tubular structure 100 as indicated by the arrows. The change in the direction caused by bent section 102 causes the agglomerated powder to engage the walls of structure 100 to assist in its deagglomeration. When reaching contracted section 104, the powder is further agitated and the flow is increased to further deagglomerate the powder. Although shown with one bent section followed by a contracted section, it will be appreciated that various other tubular structures may be provided with various arrangements of direction changes and/or constrictions to facilitate deagglomeration of the powder.

Referring now to FIGS. 15–26, various embodiments of aerosolization devices will be described. Although not shown, the aerosolization devices of FIGS. 15–26 will typically include a penetrating tube with one or more penetrating structures to pierce the lid of a receptacle similar to the embodiments previously described. These devices may also include threshold valves and regulation systems for regulating the flow of respiratory gases to the patient's lungs in a manner similar to that described with previous embodiments. Further, it will be appreciated that the components of the various devices of FIGS. 15–26 may be shared, substituted and/or interchanged with each other.

Figure 15:
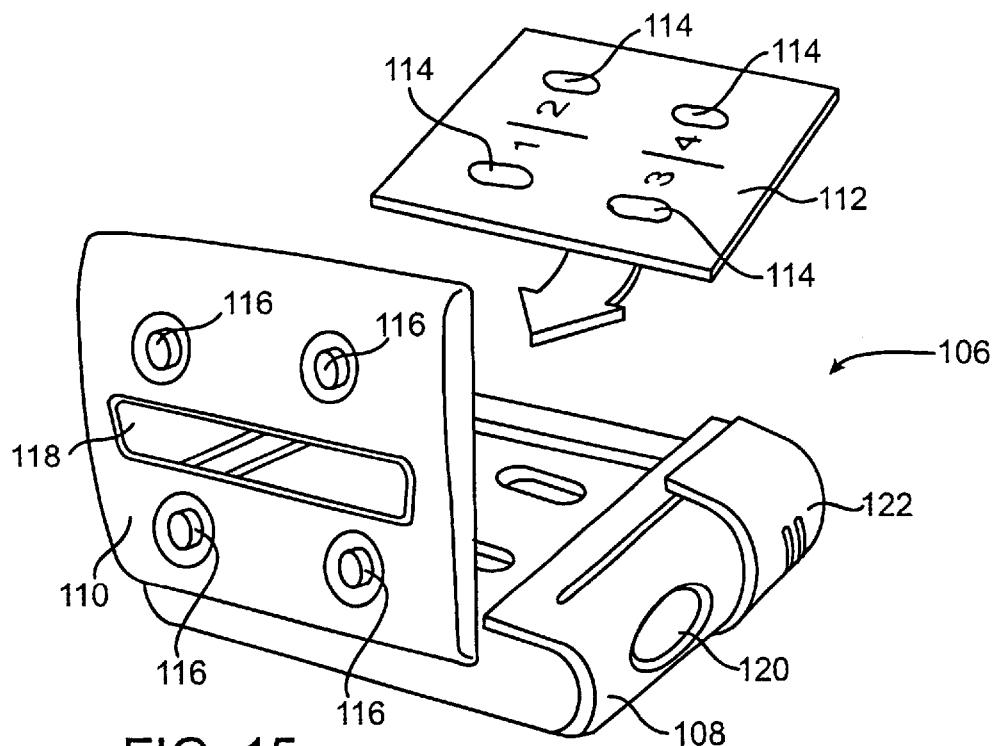
FIG. 15 is a perspective view of one embodiment of an aerosolization device according to the invention.

First referring to FIG. 15, one embodiment of an aerosolization device 106 will be described. Device 106 comprises a housing 108 having a lid 110. Lid 110 is movable to an open position to receive a sheet 112 of receptacles 114. Lid 110 includes various buttons 116 that may be pressed to puncture an associated receptacle 114 prior to inhalation. Conveniently, lid 110 includes a window 118 to indicate that sheet 112 is loaded and may also show a date and type of medication printed on sheet 112. Housing 108 further includes a mouthpiece 120 and a slidable cover 122 that may be slid over mouthpiece 120 when not in use.

When a patient is ready to receive a treatment, the patient slides cover 122 to expose mouthpiece 120. One of buttons 116 is then pressed and the user inhales while their mouth is over mouthpiece 120. Once all of buttons 116 have been pressed, sheet 112 may be replaced with a new sheet of receptacles.

Figure 16A:
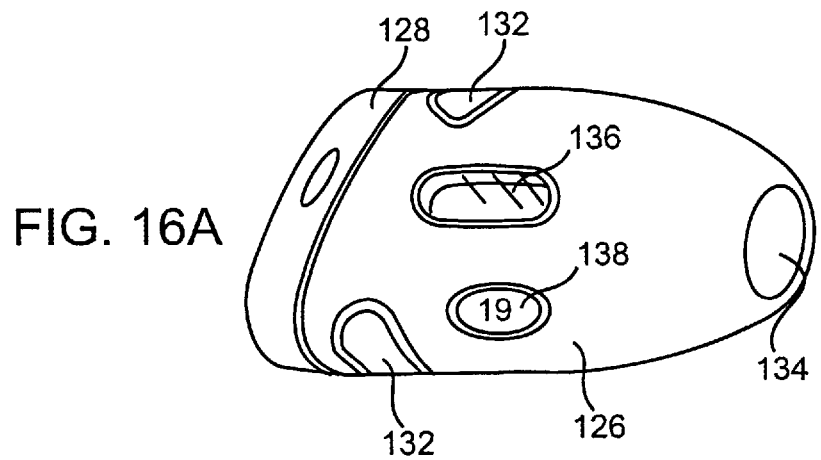
FIG. 16A illustrates a cover of the aerosolization device of FIG. 16.
Figure 16:
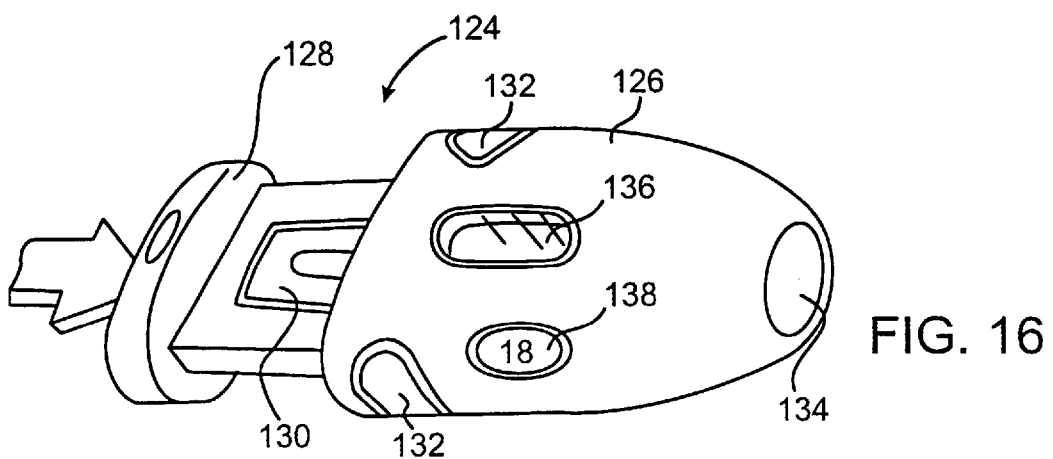
FIG. 16 is a perspective view of another embodiment of an aerosolization device according to the invention.

FIG. 16 illustrates an aerosolization device 124 that comprises a cover 126 (see also FIG. 16A) and a drawer 128 that is slidable within cover 126 as indicated by the arrow. Drawer 128 is configured to hold a receptacle 130. As shown in FIG. 16A, when drawer 128 is closed, receptacle 130 is held within cover 126. Conveniently, the chamber of receptacle 130 may be configured to be pierced when drawer 128 is closed. Various press buttons 132 may be provided to allow drawer 128 to be retracted following use. Cover 126 further includes a mouthpiece 134 and a window 136 to indicate that receptacle 130 is loaded, along with showing a date and type of medication. Optionally, a counter 138 may be provided to show the cumulative number of uses for the device.

Figure 17:
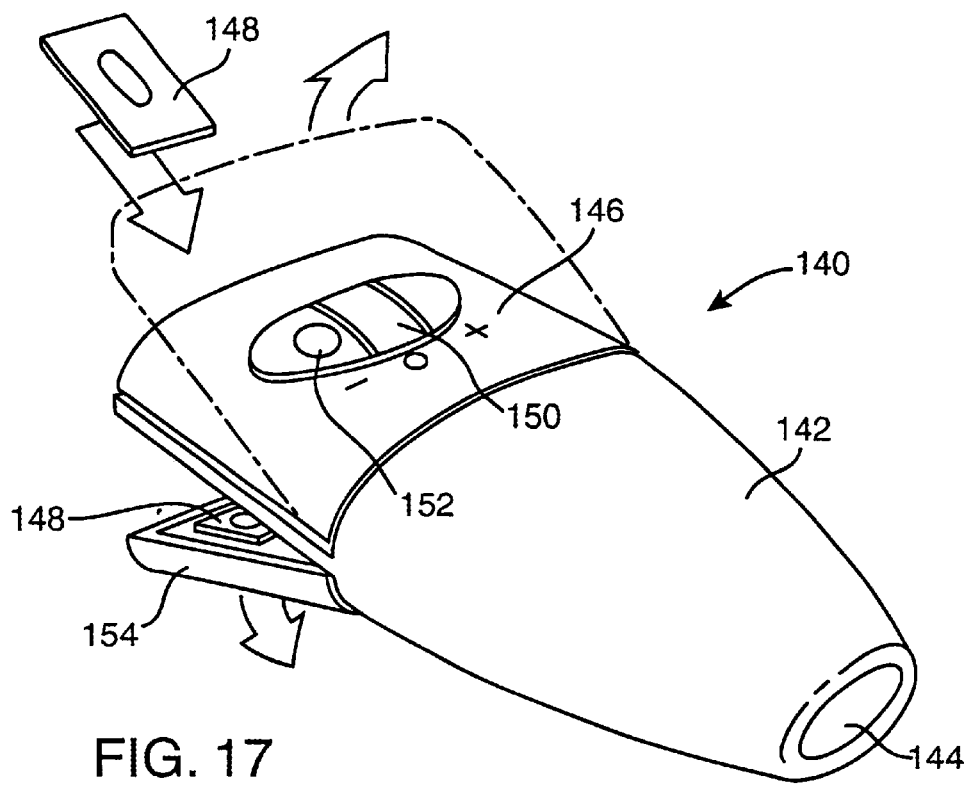
FIG. 17 is a perspective view of still another embodiment of an aerosolization device according to the invention illustrating the use of a flow rate feedback device.

FIG. 17 illustrates an aerosolizton device 140 comprising a housing 142 having a mouthpiece 144 and a lid 146. Lid 146 is movable between an open position and a closed position as illustrated in phantom line. When lid 146 is opened, a receptacle 148 may be placed within housing 142. When lid 146 is closed, receptacle 148 is pierced and device 140 is ready for operation. Conveniently, lid 146 may include a raised window 150 containing a ball 152. The region behind window 150 may be placed in communication with the airflow path, thereby causing ball 152 to move within the region depending on the rate of flow of respiratory gases through device 140. Conveniently, plus and minus signs may be used to provide the patient with visual feedback on the rate of flow through the device. In this way, the patient may adjust their inhalation rate based on the visual feedback. Optionally, device 140 may include a storage compartment 154 for holding extra receptacles 148.

Figure 18:
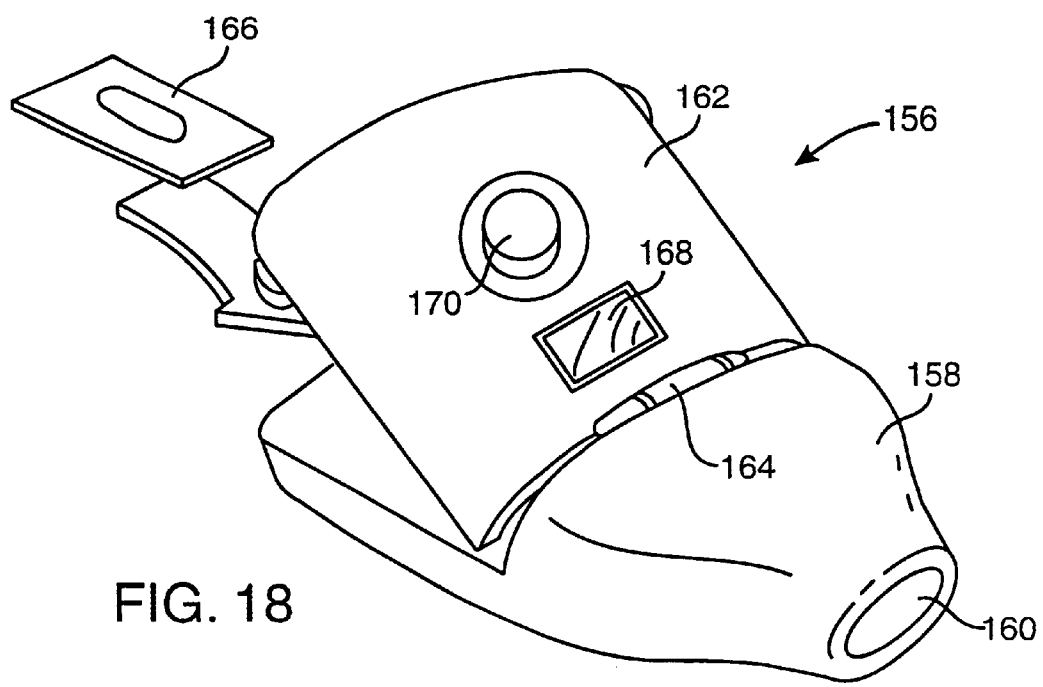
FIG. 18 illustrates still yet another embodiment of an aerosolization device according to the invention.

FIG. 18 illustrates a device 156 comprising a housing 158 having a mouthpiece 160 and a lid 162. A hinge 164 is employed to pivotally couple lid 162 to housing 158. Lid 162 is movable between an open position and a closed position. When in the open position, a receptacle 166 may be loaded into housing 158. Lid 162 is then closed, with receptacle 166 being visible through a window 168. Lid 162 includes a press button 170 which is pushed to pierce receptacle 166 prior to use.

Figure 19A:
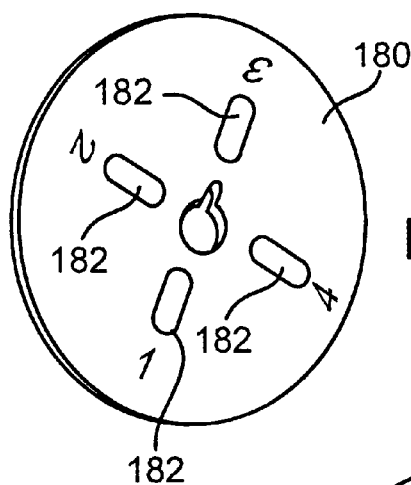
FIG. 19A illustrates a disk having multiple receptacles that may be inserted into the aerosolization device of FIG. 19.
Figure 19:
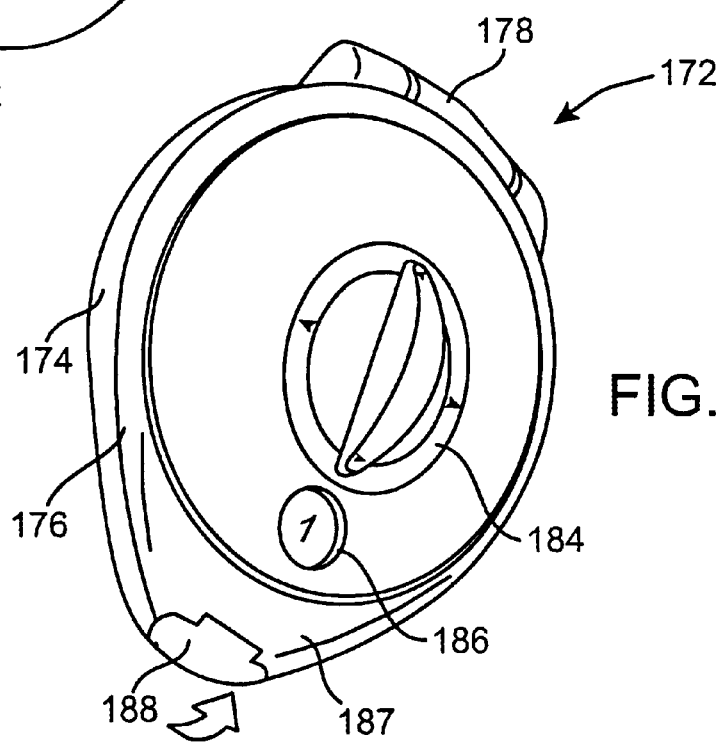
FIG. 19 illustrates one particular embodiment of an aerosolization device according the invention.
Figure 19B:
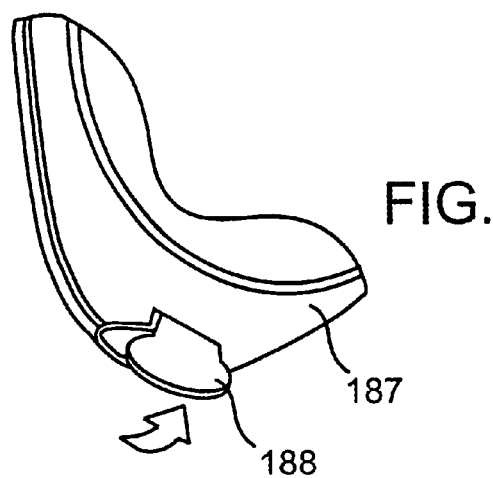
FIG. 19B illustrates a front end of the aerosolization device of FIG. 19.

FIG. 19 illustrates an aerosolization device 172 comprising a housing 174 and a door 176 that is coupled to housing 174 by a hinge 178. Insertable into device 172 is a disk 180 having multiple receptacles 182 as illustrated in FIG. 19A. Conveniently, each of the receptacles may be numbered as illustrated in FIG. 19A. Door 176 includes a dial 184 that is rotatable to rotate disk 180 within device 172. Door 176 also includes a window 186 to view the receptacle that has been pierced by rotating dial 184. When ready to receive a treatment, the user places their mouth over a nose 187 of device 172 and begins to inhale. The patient's inhalation opens a lid 188 to permit the aerosolized formulation to enter into the patient's lungs. To receive another treatment, the user simply dials dial 184 to the next receptacle which is pierced, making device 172 ready for operation.

Figure 20A:
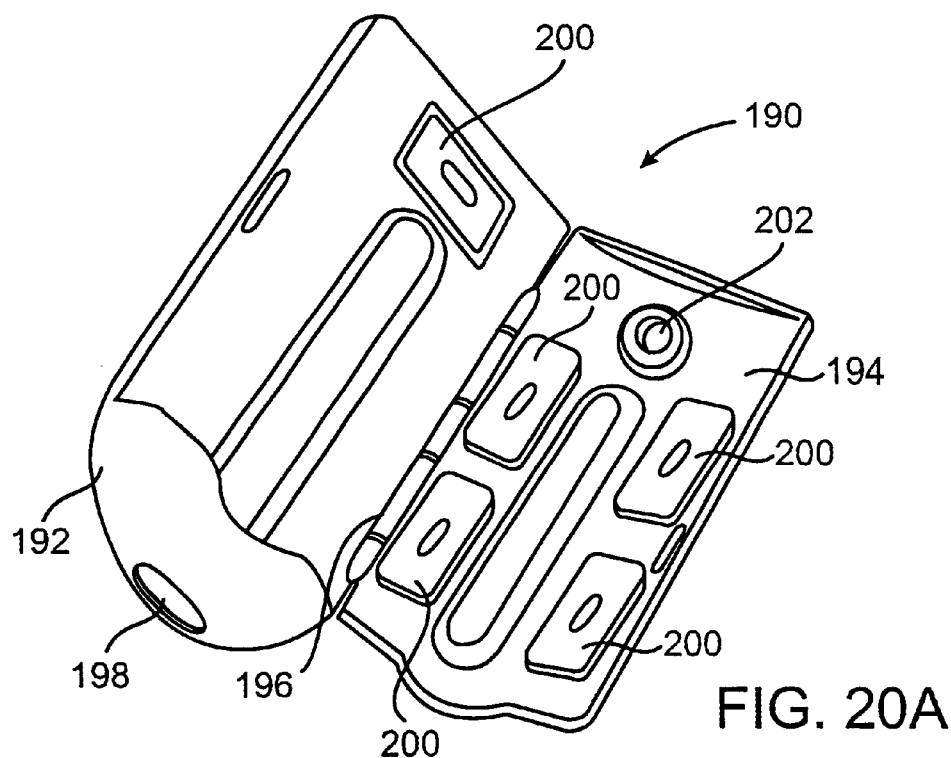
FIG. 20A illustrates the aerosolization device of FIG. 20 showing a lid moved to an open position.
Figure 20:
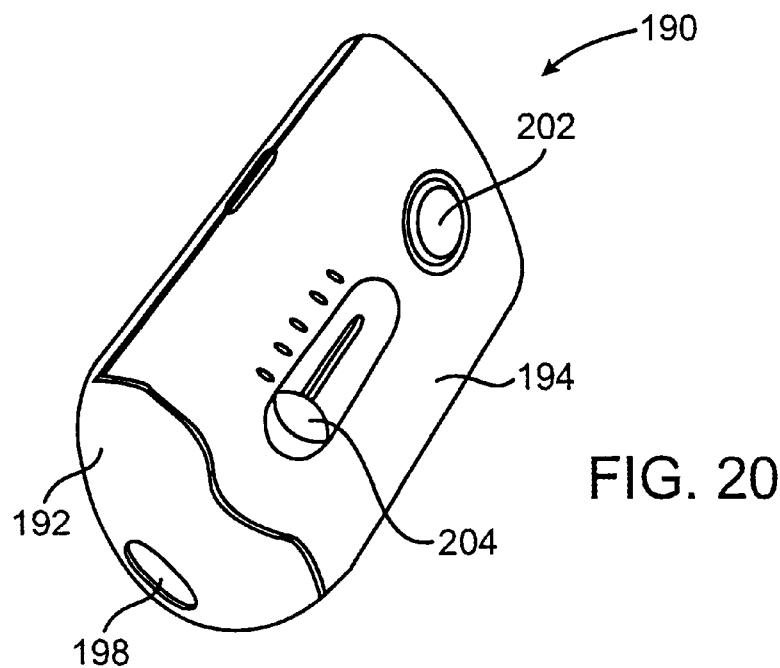
FIG. 20 illustrates another embodiment of an aerosolization device according the invention.

Referring now to FIGS. 20 and 20A, an alternative aerosolization device 190 will be described. Device 190 comprises a housing 192 and a lid 194 that is coupled to housing 192 by a hinge 196. Device 190 further includes a mouthpiece 198 through which the patient inhales. As shown in FIG. 20A, device 190 is in an open position where a receptacle 200 is placed in a loaded position. Lid 194 may then be closed to the position illustrated in FIG. 20. Lid 194 includes a press button 202 that is pressed to pierce receptacle 200 so that the pharmaceutical formulation may be extracted. Lid 194 also includes a timer 204 that is manually set by having the user pull timer 204 toward button 202 prior to operation. The user then begins to inhale from mouthpiece 198 to aerosolize the pharmaceutical formulation. Preferably, the user inhales until timer 204 expires. As shown in FIG. 20A, lid 194 may include multiple storage locations for storing additional receptacles 200.

FIG. 21 illustrates an aerosolization device 206 comprising a housing 208 having a slot 210 for receiving a receptacle 212. Device 206 further includes a cocking device 214 that is cocked to cause receptacle 212 to be pierced. Device 206 further includes a trap door 216 and an extendable mouthpiece 218 (shown in phantom line). When cocking device 214 is cocked to pierce receptacle 212, trap door 216 is also opened and mouthpiece 218 is extended.

Referring now to FIG. 22, another aerosolization device 220 will be described. Device 220 comprises a housing 222 and a clip 224 that may be coupled to housing 222. As best shown in FIG. 22A, clip 224 includes a storage region 226 and a waste region 228. Storage region 226 includes multiple receptacles 230 that may be loaded into housing 222 as described hereinafter. Once a receptacle has been used, it is ejected into waste region 228. Conveniently, a removable sea 232 may be disposed over storage region 226. Use of clip 224 is advantageous in that replacement clips, having a fresh supply of receptacles, may easily be coupled to housing 222, making device 220 a multi-use device.

As best shown in FIG. 22, housing device 220 further includes a rotatable dial 234 that is rotated to advance one of the receptacles 230 from storage region 226 and into housing 222. When placed within housing 222, receptacle 230 is pierced. Further, housing 222 includes a counter 236 to display how many receptacles remain unpierced. A tethered mouthpiece cover 238 is coupled to housing 222 and is removed prior to inhalation.

Hence, to use device 220, the user simply rotates dial 234 to advance and pierce the next receptacle. Cover 238 is removed and the patient inhales to aerosolize the pharmaceutical formulation and deposit the formulation within the patient's lungs. When ready for a next dosage, dial 234 is again dialed causing the used receptacle to be ejected into waste region 228 and advancing another receptacle. When all receptacles have been used, clip 224 is removed and placed with a replacement clip.

FIG. 23 illustrates an aerosolization device 240 comprising a housing 242 and a lid 244 pivotally coupled to housing 242. A removable mouthpiece cover 246 is also provided (see also FIG. 23A). Cover 246 is removed prior to inhalation by the patient. Device 240 is configured to hold a strip 248 of receptacles 250 (as shown in FIG. 24). Once strip 248 is within housing 242, a slide 252 may be moved to indicate the desired receptacle that is to be pierced. Slide 252 may then be depressed to pierce the selected receptacle. Optionally, slide 252 may be coupled to plumbing within device 240 so that the plumbing is moved to the appropriate receptacle along with slide 252. Device 240 may also include a whistle 254 that produces an audible signal when the user inhales in excess of a maximum inhalation flow rate. The user may simply inhale at a slower flow rate until whistle 254 ceases producing a whistling sound.

Figure 25:
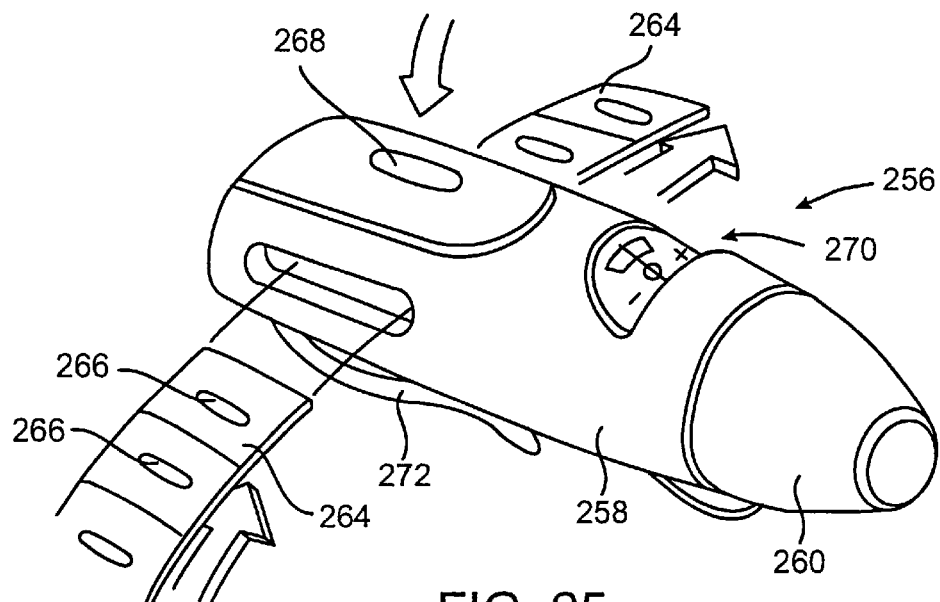
FIG. 25 illustrates still another alternative embodiment of an aerosolization device according to the invention.

FIG. 25 illustrates an aerosolization device 256 comprising a housing 258 and a mouthpiece cover 260 that is tethered to housing 258. Cover 260 is removed prior to use. Housing 258 further includes a slot 262 that extends through housing 258. In this way, a continuous strip 264 of receptacles 266 may be fed through slot 262. Alternatively, strip 264 may be separated into segments so that an individual receptacle may be fed into slot 262. Housing 258 includes a button 268 that may be depressed to pierce the loaded receptacle.

When the patient begins to inhale, their flow rate is monitored by a gas gauge 270. In this way, the user is provided with visual feedback to assist them in inhaling at the proper flow rate. Optionally, housing 258 may include a clip 272 to permit device 258 to be carried on the pocket like a pen.

Figure 26:
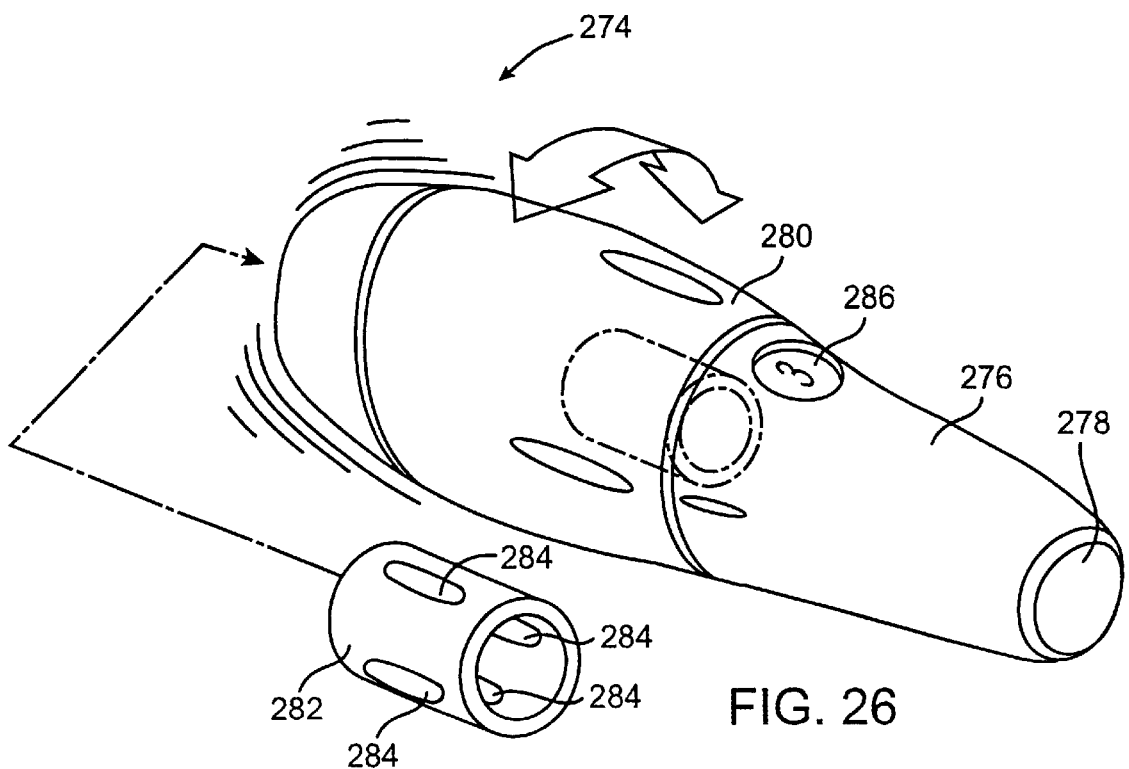
FIG. 26 illustrates one embodiment of an aerosolization device according to the invention.

FIG. 26 illustrates an aerosolization device 274 comprising a housing 276 having a mouthpiece 278 and a rotatable body 280 that is rotatable relative to housing 276. Device 274 is configured to receive a receptacle pack 282 at a back end of device 274. Receptacle pack 282 includes multiple receptacles 284 that may be pierced when ready for use. Although receptacle pack 282 is shown as being cylindrical in geometry, it will be appreciated that other geometries may be employed, including square shaped tubes.

Once receptacle pack 282 is inserted into device 274, rotatable body 280 is rotated to advance one of the receptacles to an engaging position where the receptacle is pierced. Conveniently, housing 276 includes a counter 286 to display the remaining number of receptacles. If the patient inhales at an excessive flow rate, housing 276 is configured to vibrate to provide the user with feedback so that they may adjust their inhalation flow rate.

A wide variety of threshold valves may be used to prevent the flow of gases to the patient's lungs until the patient has produced a sufficient vacuum needed to extract the powder from the receptacle. Such valves may be configured to prevent any flow of gases until the vacuum produced by the patient meets or exceeds the threshold actuating pressure of the valve. After the valve opens, minimal flow resistance is provided by the valve. Once the flow stops, the valve may be configured to reset to its former starting position.

Figure 27:
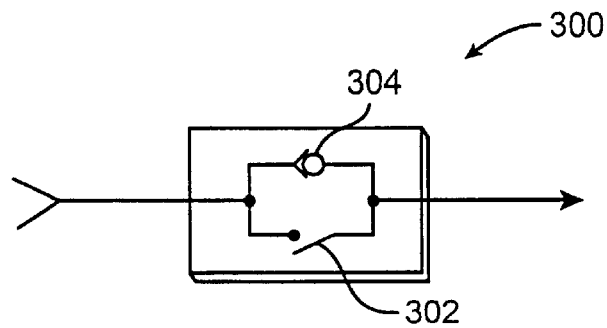
FIG. 27 is a schematic diagram of a threshold valve according to the invention.

Shown in FIG. 27 is a schematic diagram of a valve system 300 having a threshold valve 302 that may be configured to crack at a pressure in the range from about 20 cm $H_2O$ to about 60 cm $H_2O$, and more preferably at least about 50 cm $H_2O$, to allow gas flow through the aerosolization device in the direction indicated by the arrows. In this way, a relatively high flow rate may be achieved for a short duration at the beginning of inhalation to allow the powder to be dispersed from the receptacle.

Optionally, system 300 may include a check valve 304 to prevent the user from blowing through the device. Such a check valve may be incorporated anywhere in the aerosolization device, and for convenience may be integrated with the threshold valve. System 300 may be configured to have little resistance to the flow of gases once valve 302 is opened. In some cases, system 300 may be configured to have a reset feature to reset valve 302, if needed. In some cases, system 300 may be configured to have an adjustment mechanism to permit the adjustment of the threshold actuating pressure, lowering of any reset vacuum level, and/or raising of back flow resistance pressure.

One type of threshold valve that may be used is a silicone rubber valve that is tailored to provide flow onset at the desired threshold pressure and to provide reverse flow inhibition. Such a valve is also self resetting, requiring no mechanical resistance. Examples of such valves are described in, for example, U.S. Pat. Nos. 4,991,745, 5,033,655, 5,213,236, 5,339,995, 5,377,877, 5,409,144, and 5,439,143, the complete disclosures of which are herein incorporated by reference.

Figure 28:
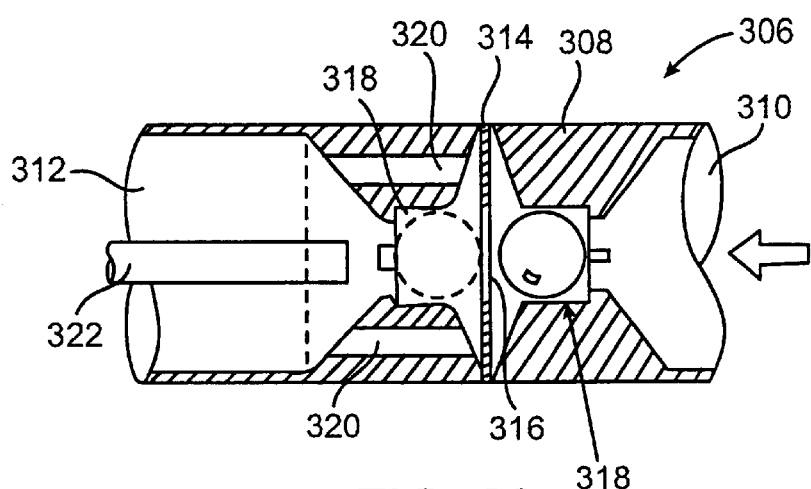
FIG. 28 is a ball and membrane threshold valve according to the invention.

Examples of various types of threshold valves that may be incorporated into an aerosolization device are illustrated in FIGS. 28–40. Shown in FIG. 28 is a pull through threshold valve 306 that is constructed of a housing 308 having an inlet 310 and an outlet 312. A membrane 314, such as an elastomeric membrane, is disposed across the interior of housing 308 and has a central opening 316. A ball 318 is sealed within housing 308 and is configured to be pulled through opening 316 when a sufficient vacuum is created by the user as shown in phantom line. Once ball 318 passes through membrane 314, gas flow is permitted through housing 308 by passing through passages 320. Conveniently, a reset rod 322 may be used to push ball 318 back to the other side of membrane 314 in order to reset the valve for another use.

Figure 29:
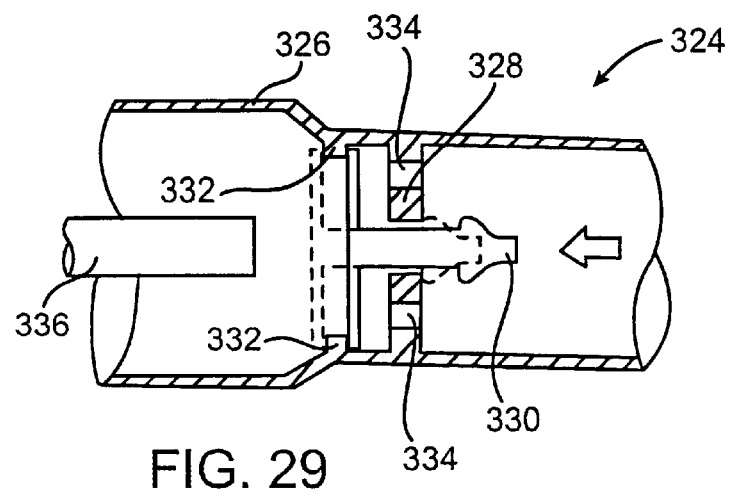
FIG. 29 is an umbrella type threshold valve according to the invention.

FIG. 29 illustrates an umbrella pull through valve 324. Valve 324 comprises a housing 326 having a support member 328 for supporting an umbrella member 330. Housing 326 also includes tabs 332 which prevent axial movement of umbrella member 330 until the user creates a sufficient vacuum. At such a time, umbrella member 330 flexes to pass tabs 332 as shown in phantom line. Gases are then permitted to flow through openings 334 in support 328. A reset rod 336 may be used to push umbrella member 330 back past tabs 332 prior to another use.

Figure 30:
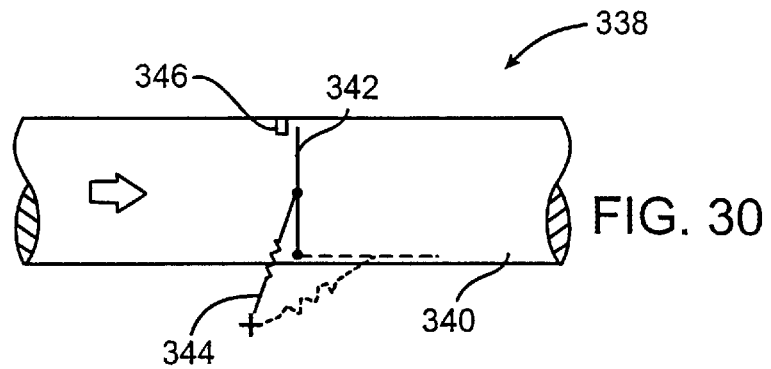
FIG. 30 schematically illustrates one embodiment of a threshold valve according to the invention.

FIG. 30 illustrates a threshold valve 338 comprising a tubular housing 340 across which a valve member 342 is pivotally disposed. A biasing member 344 biases valve member 342 against a tab 346. In this way, gases are permitted to flow through housing 340 once a sufficient vacuum is created to overcome the biasing force and thereby permit valve member 342 to open as shown in phantom line.

Figure 31A:
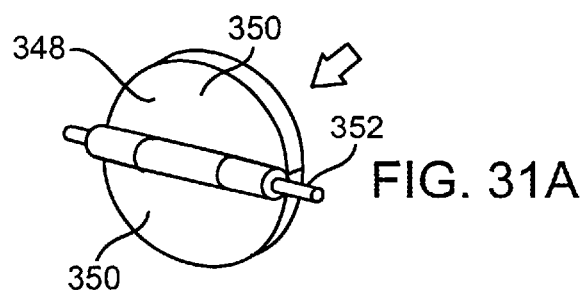
FIGS. 31A and 31B illustrate a flapper type threshold valve according to the invention.
Figure 31B:
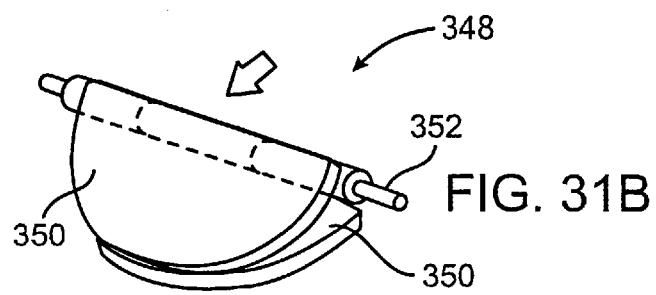

FIG. 31A illustrates a flapper valve 348 that may be used in a tubular housing. Valve 348 comprises two valve members 350 that are pivotally coupled to a shaft 352. A spring (not shown) biases members 350 in the position shown in FIG. 31A. When a sufficient vacuum force is provided, the spring force is overcome and members 350 move to the open position shown in FIG. 31B to permit to flow of gases.

Figure 32:
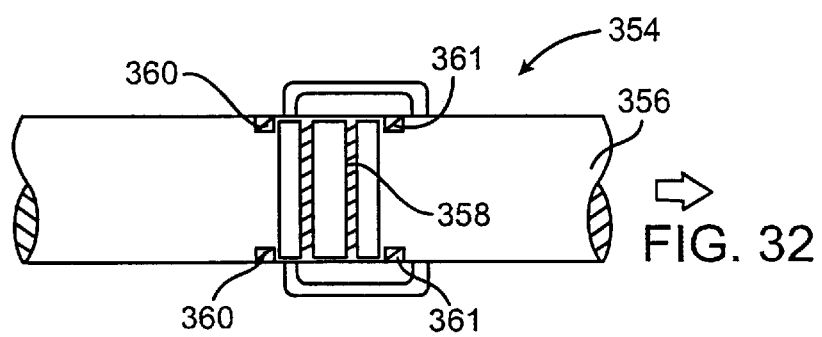
FIG. 32 illustrates a spindle type threshold valve according to the invention.

FIG. 32 illustrates a spindle type valve 354 that comprises a tubular housing 356 having a spindle 358 that is held between tabs 360 and 361. Pass through channel 362 are arranged such that gases are permitted to flow through channels 362 and around spindle 358 when the vacuum created by the user moves the spindle to tabs 361. The frictional force between spindle 358 and housing 356 may be varied depending on the desired threshold force required to open the valve.

Figure 33:
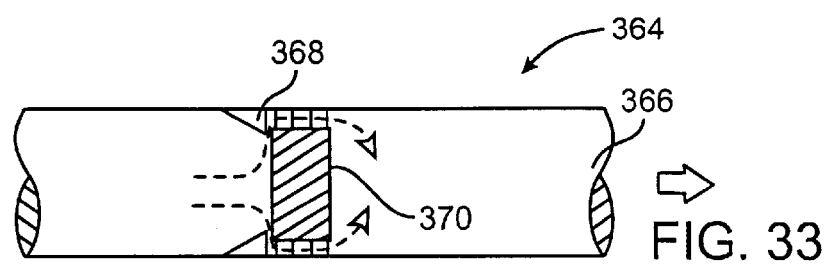
FIG. 33 illustrates another spindle type threshold valve according to the invention.

FIG. 33 illustrates another spindle type valve 364 comprising a tubular housing 366 having a stop 368. A spindle 370 is disposed within housing 366 so as to be adjacent stop 366, thereby preventing the flow of gases through housing 366. When a sufficient vacuum has been produced by the patient, spindle 370 slides within housing 366 and away from stop 366. In this way, gases are permitted to flow through housing 366.

Figure 34A:
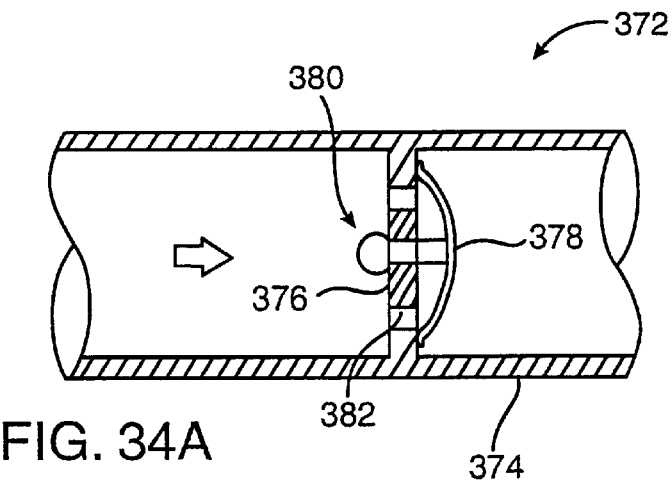
FIGS. 34A and 34B illustrate an umbrella type threshold valve according to the invention.
Figure 34B:
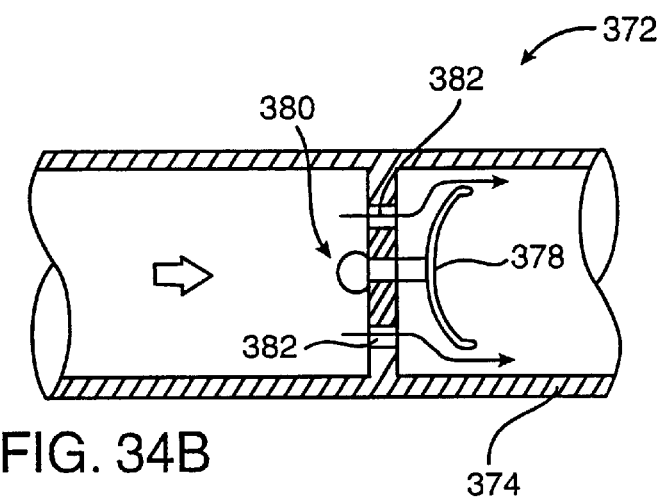

FIG. 34A illustrates a threshold valve 372 that comprises a tubular housing 374 having a support 376 that holds an evertible umbrella member 378 having a ball 380. Ball 380 serves to secure member 378 to support 376 when a vacuum is applied by the user. As shown in FIG. 34B, member 378 is configured to evert when a sufficient vacuum is produced by the user. When in the everted position, gases flow through openings 382 in support 376 as shown. Member 378 may be reset to the position shown in FIG. 34A prior to another use.

Figure 35:
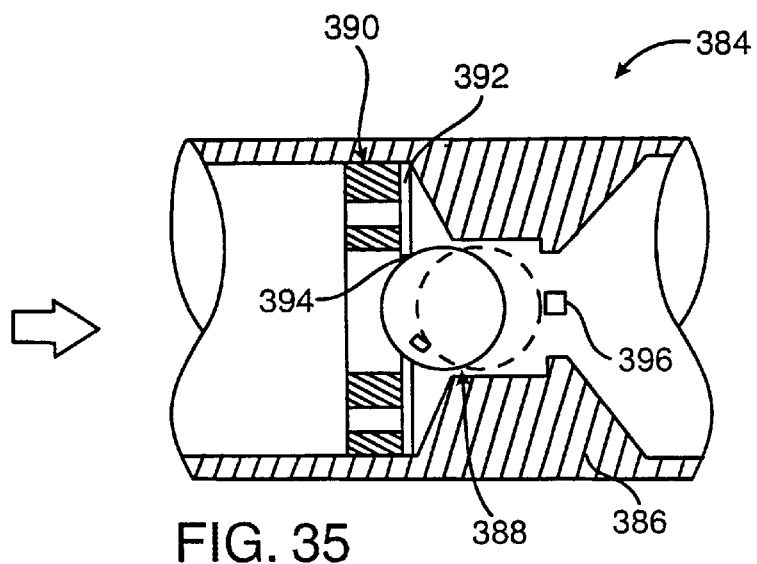
FIG. 35 illustrates a ball and magnet type threshold valve according to the invention.

The threshold valve may be a valve designed to alternate between open and closed positions based upon a predetermined magnetic field strength. For example, FIG. 35 illustrates a threshold valve 384 comprising a housing 386 that holds a steel ball 388. Also disposed within housing 386 is a magnet 390 and an elastomeric gasket 392 having a central opening 394 that is smaller in diameter than ball 388. In this way, magnet 390 holds ball 388 across opening 394 to prevent the flow of gases through housing 386. When the user provides a sufficient vacuum, ball 388 is moved against a stop 396 as shown in phantom line. Gases are then free to flow through opening 394 and around ball 388. The magnetic field is designed to be strong enough such that the ball is reset to obstruct airflow when the user stops the inhalation.

Figure 36A:
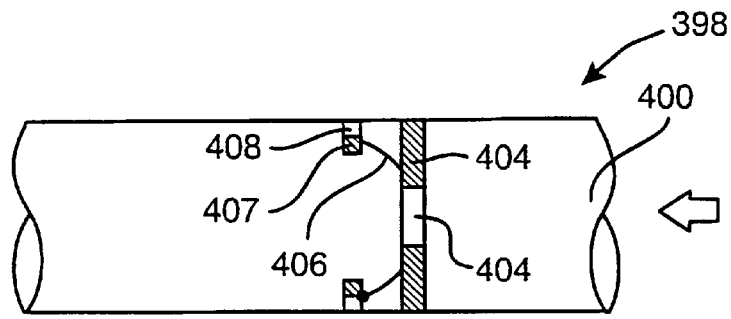
FIGS. 36A and 36B illustrate a bistable dome type threshold valve according to the invention.
Figure 36B:
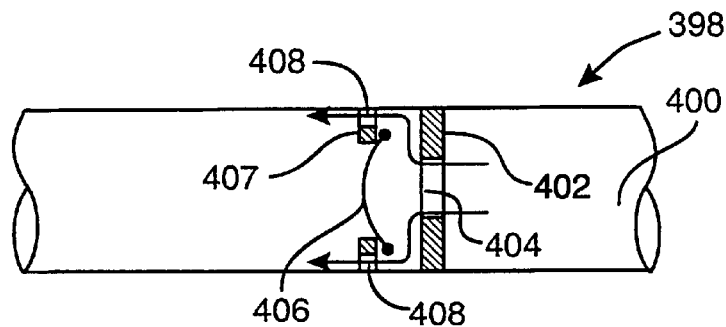

FIG. 36A illustrates a threshold valve 398 comprising a tubular housing 400 having a restriction 402 with a central orifice 404. A bistable dome 406 is coupled to a support 407 and is disposed across the interior of housing 400 to cover orifice 404 when in the position shown in FIG. 36A. When a user provides a sufficient vacuum, dome 406 performs a bistable function to move to the position shown in FIG. 36B. In this way, gases may flow through orifice 404 and then through openings 408 in support 407 as shown by the arrows.

Figure 37A:
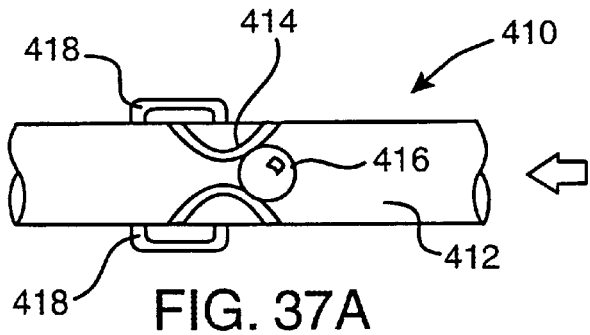
FIGS. 37A and 37B illustrate a mechanical pressure switch type threshold valve according to the invention.
Figure 37B:
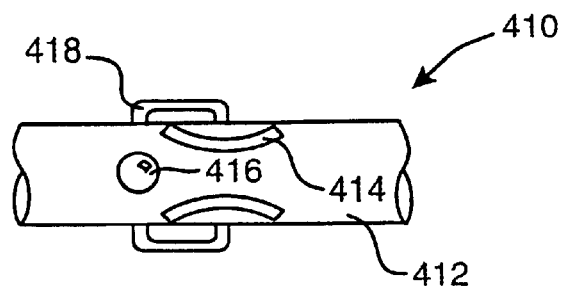

FIG. 37A illustrates a threshold valve 410 that comprises a tubular housing 412 having a flexible bladder 414 that is sealed to housing 412. When the pressure is below a threshold pressure, bladder 414 maintains the shape shown in FIG. 37A. In this way, a ball 416 is prevented from passing through bladder 414, thereby preventing the flow of gases through housing 412. Channels 418 are in communication with the interior of bladder 414 so that when the patient produces a vacuum that is greater in magnitude than the threshold pressure, bladder 414 moves to the position shown in FIG. 37B to permit gases to flow through housing 412.

Figure 38:
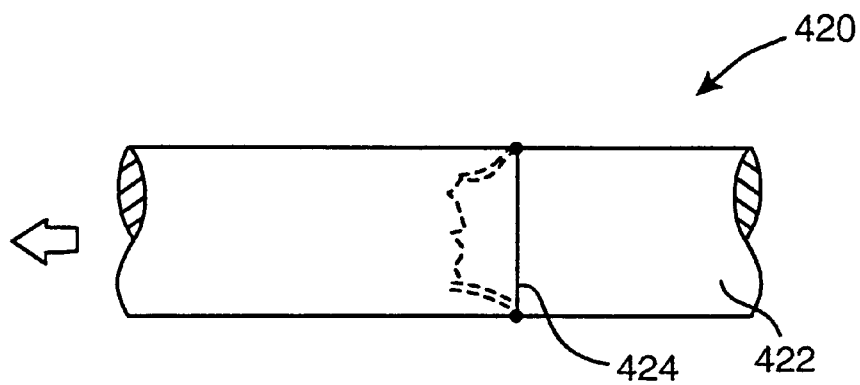
FIG. 38 illustrates a frangible membrane type of threshold valve according to the invention.

FIG. 38 illustrates a threshold valve 420 comprising a tubular housing 422 having a frangible diaphragm 424. Diaphragm 424 is configured to rupture when a threshold vacuum has been applied by the user as shown in phantom line.

Figure 39:
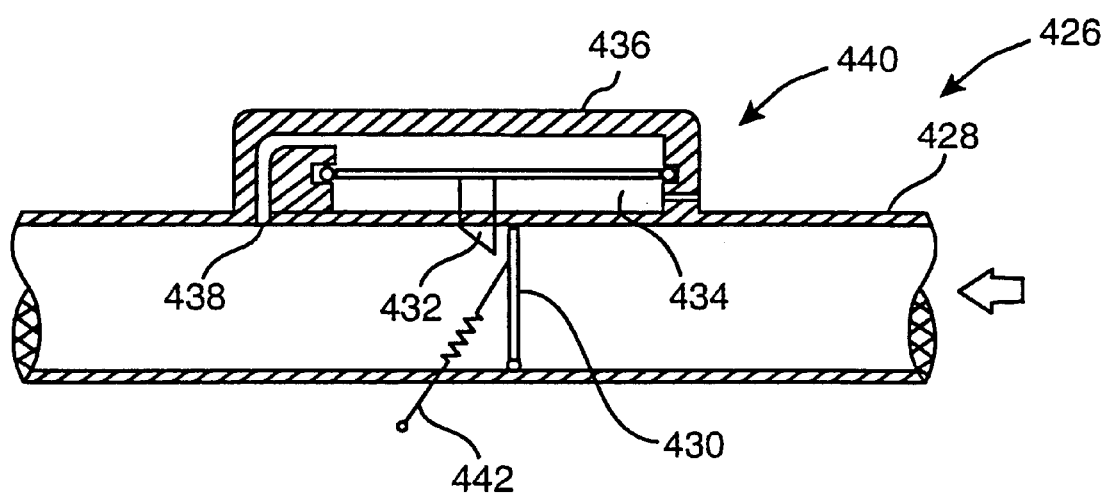
FIG. 39 illustrates another mechanical pressure switch type threshold valve according to the invention.

FIG. 39 illustrates a threshold valve 426 comprising a tubular housing 428 and a valve member 430 pivotally coupled to housing 428. Valve member 430 prevents the flow of gases through housing 428 when in a closed position as shown in FIG. 39. A stop 432 prevents valve member 430 from opening until a threshold vacuum is produced by the user. Stop 432 is coupled to a membrane 434 that is held within a chamber 436. Chamber 436 is in communication with the interior of housing 428 by a passage 438. In this way, when a sufficient vacuum has been produced, stop 432 is lifted up to permit valve member 430 to open. Conveniently, a vent 440 may be provided to permit air to flow into chamber 436 when membrane 434 moves upward. Also, a spring 442 may be provided to move valve member 430 to the open position when stop 432 is raised.

Figure 40:
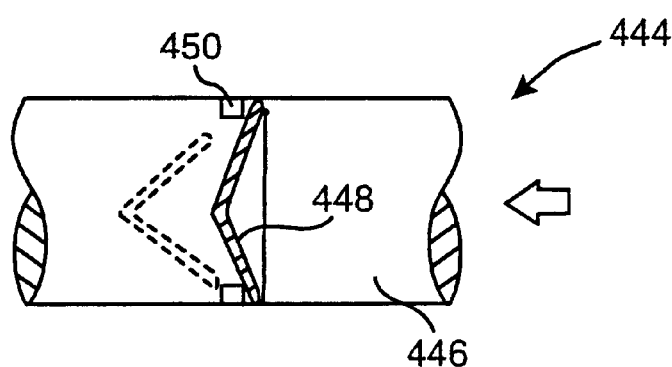
FIG. 40 illustrates a pull through type threshold valve according to the invention.

FIG. 40 illustrates a pull through type threshold valve 444 that comprises a housing 446 and a valve member 448 that is disposed within housing 446. A stop 450 holds valve member 448 in place until a threshold pressure is produced by the patient. At such a time, valve member 448 collapses as shown in phantom line to permit valve member 448 to pass beyond stop 450.

A variety of flow regulators may be used to limit the flow of gases through the aerosolization device and into the user's lungs after the powder has been extracted from the receptacle and aerosolized. Such flow regulators are provided to limit the flow rate through the device for a specified time to insure that the flow rate is slow enough for the aerosol to travel through the airways and past the anatomical dead volume.

Figure 41:
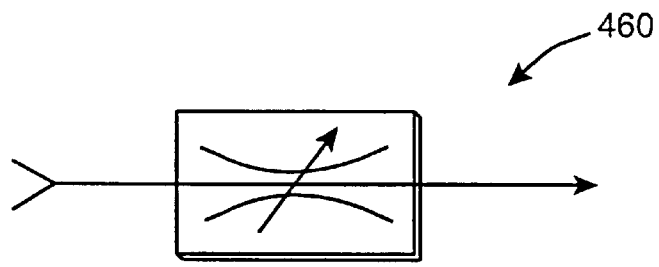
FIG. 41 is a schematic diagram of a flow regulator according to the invention.

FIG. 41 schematically illustrates one embodiment of a flow regulator 460. Regulator 460 may be configured to limit the flow of gases to be less than about 15 L/min, and more preferably less than about 10 L/min. Regulator 460 may be configured such that the resistance to the flow is small at low vacuum and increases with the vacuum generated by the user. Conveniently, regulator 460 may be placed in a flow path that is parallel to the receptacle containing the powder. In such a case, the flow regulator may provide a system resistance to flow R that varies from about 0.1 (cm H$_2$O)$^{1/2}$/standard liters per minute (SLM) up to the resistance of the receptacle flow path. Alternatively, the flow controller may be placed in series with the receptacle. In such a case, the system resistance R may vary from the resistance of the receptacle flow path up to a resistance greater than 1.0 (cm H$_2$O)$^{1/2}$/SLM.

Figure 42A:
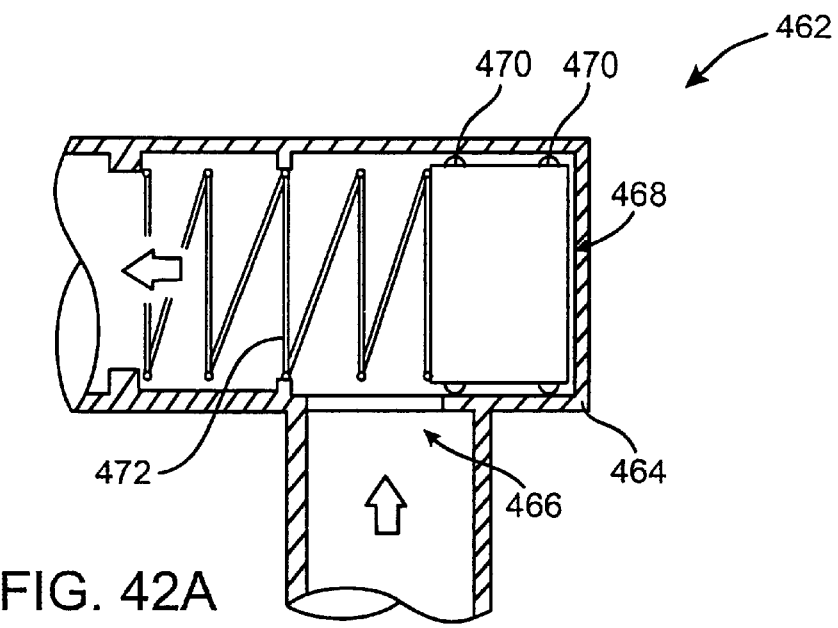
FIGS. 42A and 42B illustrate a shuttle type flow regulator according to the invention.
Figure 42B:
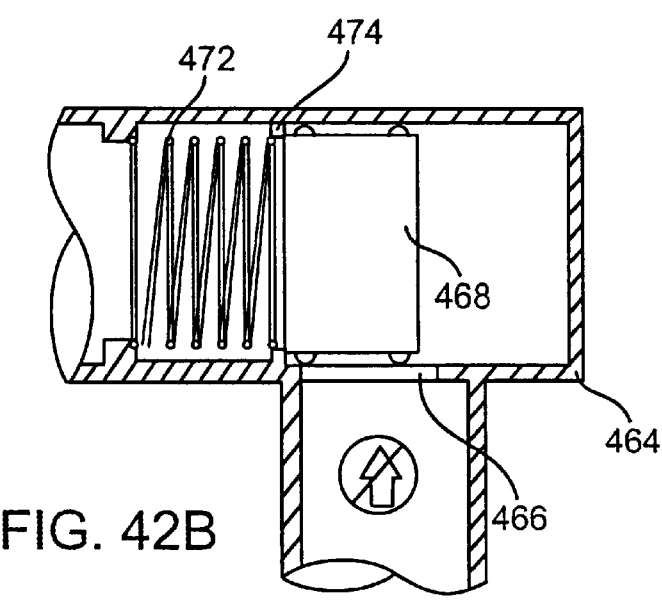

Shown in FIGS. 42–59 are various types of flow regulators that may be used in aerosolization devices to regulate gas flow after the receptacle has been opened. For example, FIG. 42A illustrates a flow regulator 462 comprising an L shaped housing 464 having a flow channel 466. A shuttle 468 having skirt seals 470 is slidable within housing 464. A return spring 472 biases shuttle 468 in the position shown in FIG. 42A. As the flow rate through housing 464 increases, shuttle 468 moves within housing 464 to compress spring 472 and close off flow channel 466. In this way, the flow rate is limited to a certain rate. If the flow rate is too excessive, channel 466 closes as shuttle 468 engages stops 474 as shown in FIG. 42B. When the flow stops, spring 472 moves shuttle 468 to the starting position.

Figure 43:
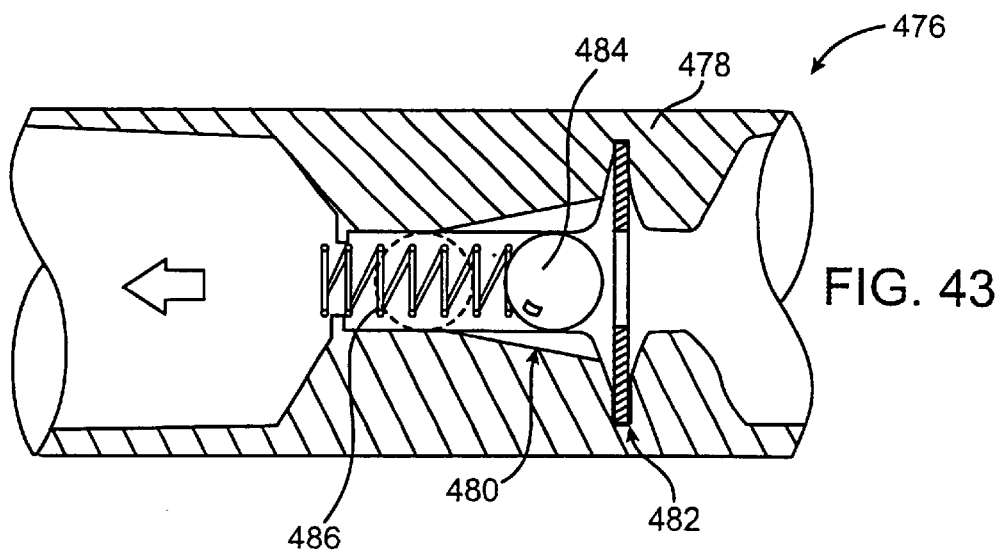
FIG. 43 illustrates a ball type flow regulator according to the invention.

FIG. 43 illustrates a flow regulator 476 that also includes a threshold valve that is similar in construction to that previously described in connection with FIG. 28. Regulator 476 comprises a housing 478 having a tapered flow channel 480 and a membrane 482 that serves as a threshold valve in a manner similar to that previously described. In FIG. 43, a ball 484 has passed through membrane 482 and is forced against a spring 486 by the vacuum produced by the user. As the vacuum increases, spring 486 compresses as ball 484 moves further into channel 480 as shown in phantom line. As a result, the flow path is restricted, thereby limiting the flow of gases. The spring constant of spring 486 may be adjusted to provide the desired flow control features.

Figure 44A:
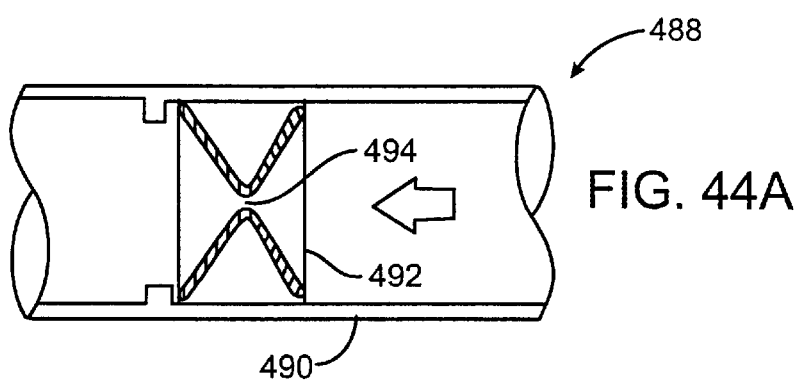
FIGS. 44A and 44B illustrate a bellows type flow regulator according to the invention.
Figure 44B:
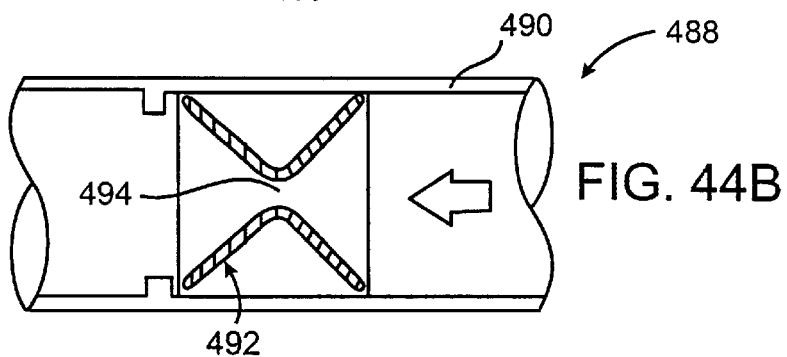

FIGS. 44A and 44B illustrate a flow regulator 488 comprising a tubular housing 490 into which a bellows 492 is disposed. Bellows 492 may be constructed of an elastomer that is configured to compress when the flow through housing 490 increases as shown in FIG. 44A. As bellows 492 compresses, a flow path 494 through the bellows decreases to limit the flow rate.

Figure 45:
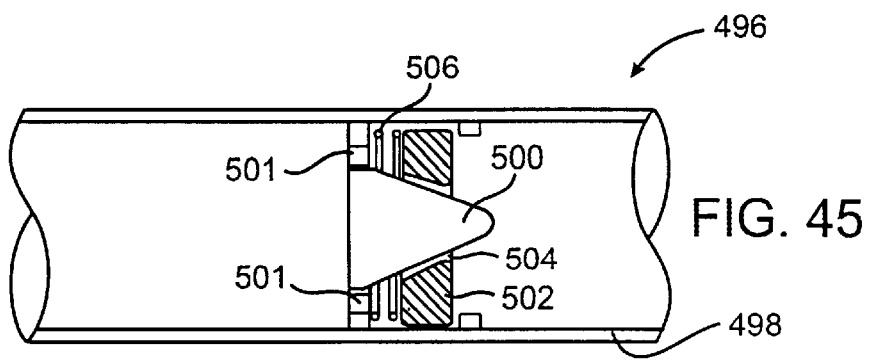
FIG. 45 illustrates a cone type flow regulator according to the invention.

FIG. 45 illustrates a flow regulator 496 comprising a tubular housing 498 into which a cone member 500 having orifices 501 is slidably disposed. A restriction member 502 having a flow channel 504 is also held within housing 498. A spring 506 is disposed between cone member 500 and restriction member 502. As the flow rate through orifices and flow channel 504 increases, spring 506 compresses and cone member 500 moves further into flow channel 504, thereby limiting the flow of gases through housing 498.

Figure 46:
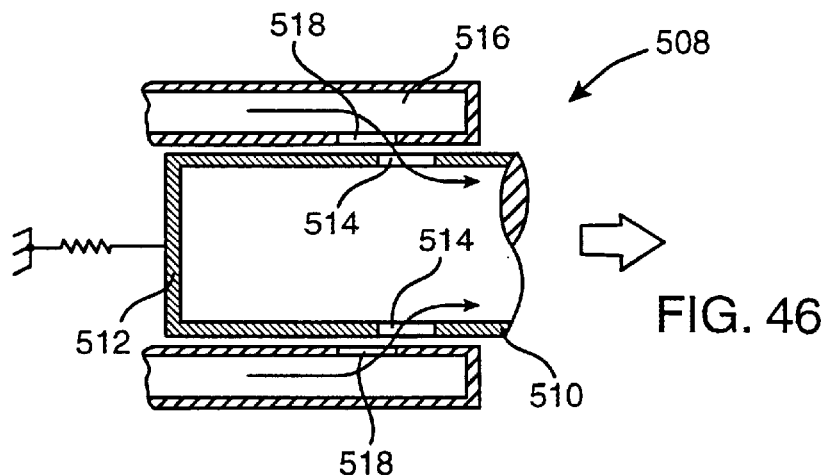
FIG. 46 illustrates another embodiment of a flow regulator according to the invention.

FIG. 46 illustrates a flow regulator 508 that comprises a tubular housing 510 having a closed end 512 and flow channels 514 that permit gases to flow into housing 510 from another housing 516 having flow channels 518. A spring 520 biases housing 510 to the left as shown in FIG. 46. As the flow rate increases, spring 520 extends and moves housing 510 to the right of FIG. 46. In so doing, flow channels 514 are restricted by housing 516 to limit the gas flow.

Figure 47:
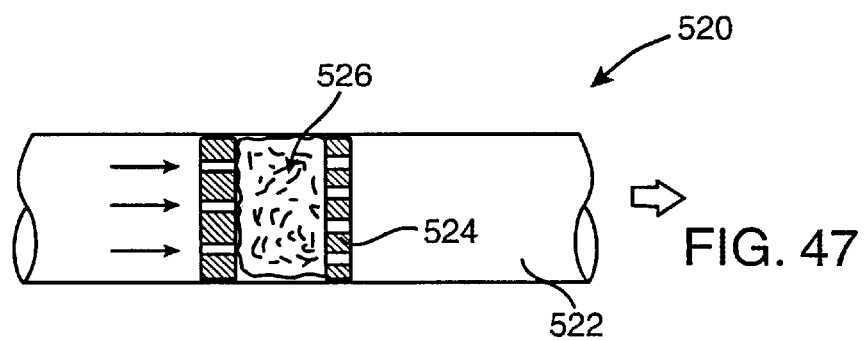
FIG. 47 illustrates a foam type flow regulator according to the invention.

FIG. 47 illustrates a flow regulator 520 that comprises a tubular housing 522 having a compartment 524 that is filled with an open cell foam 526. The open cell foam material restricts and regulates the flow of gases through housing 522, by using the applied vacuum to compress the foam and constrict the porous flow channels.

Figure 48:
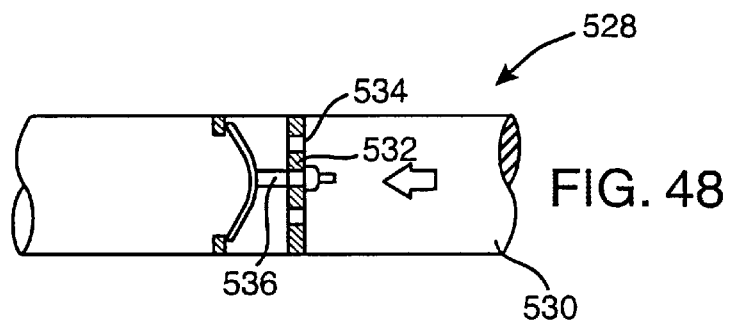
FIG. 48 illustrates an umbrella type flow regulator according to the invention.

FIG. 48 illustrates a flow regulator 528 that comprises a tubular housing 530 having a support 532 with a plurality of orifices 534. An umbrella member 536 is held by support 532 and limits gas flow through housing 530. Conveniently, umbrella member 536 may be evertible in a manner similar to that described in connection with FIGS. 43A and 43B to also function as a threshold valve.

Figure 49:
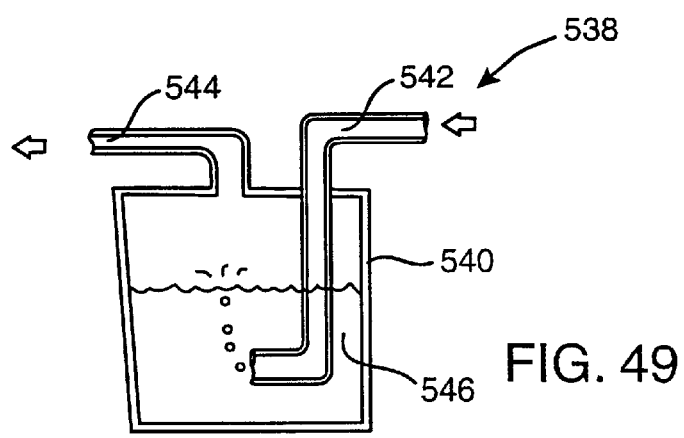
FIG. 49 illustrates a liquid reservoir flow regulator according to the invention.

FIG. 49 illustrates a flow regular 538 that comprises a housing 540 having an inlet tube 542 and an outlet tube 544. Disposed within housing 540 is a liquid 546. As gases flow through housing 540, the gases bubble through liquid 546 which regulates the flow of the gases through housing 540.

Figure 50:
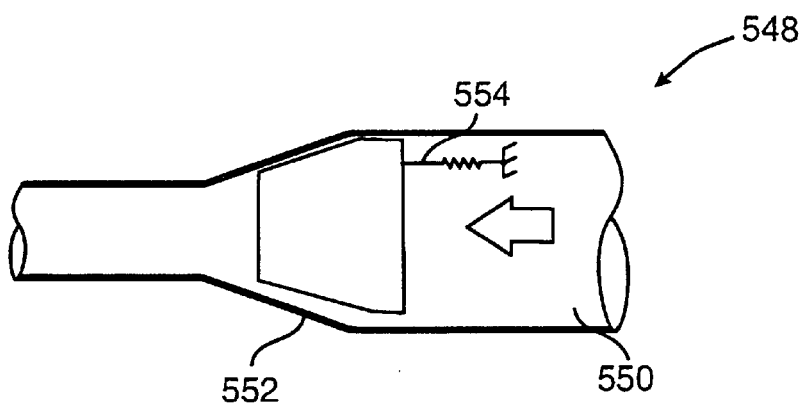
FIG. 50 illustrates another embodiment of a flow regulator according to the invention.

FIG. 50 illustrates a flow regulator 548 that comprises a tubular housing 550 having a necked region 552. A shuttle 554 is held within housing 550 and is forced into necked region 552 as the vacuum force increases. The force required to move the shuttle 554 is controlled by a spring 556. In this way, as the vacuum force increases, the flow path is restricted to limit the flow rate through housing 550.

Figure 51:
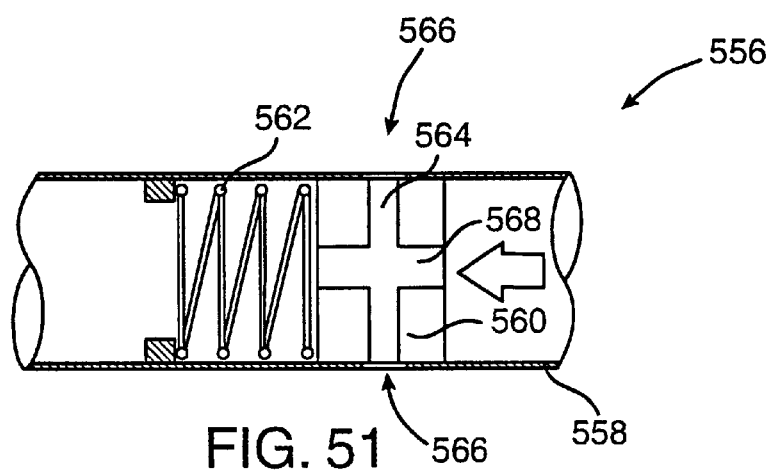
FIG. 51 illustrates a spindle type flow regulator according to the invention.

FIG. 51 illustrates a flow regulator 556 that comprises a tubular housing 558 having a spindle 560 that is slidable within housing 558. A spring 562 biases spindle 560 to the right as shown in FIG. 51 so that a flow path 564 of spindle 560 is aligned with flow paths 566 in housing 558. Hence, in the position shown in FIG. 51, gases may flow through housing 558 by passing through flow paths 564 and a flow path 568 in spindle 560. However, as the vacuum force increases, spindle 560 moves to the left to restrict flow paths 566, thereby limiting the flow of gases through housing 558.

Figure 52:
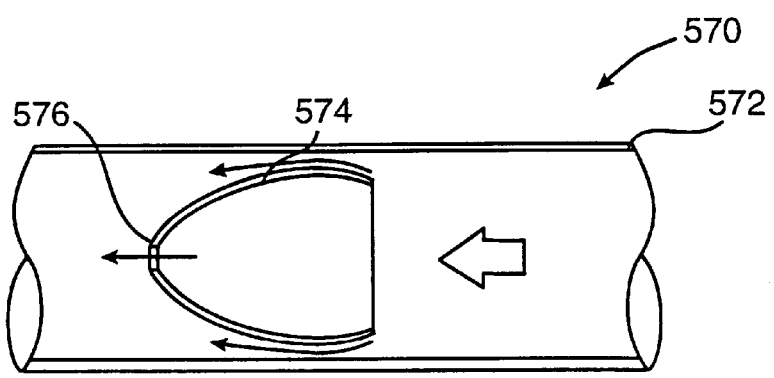
FIG. 52 illustrates an expandable cone type flow regulator according to the invention.

FIG. 52 illustrates a flow regulator 570 comprising a tubular housing 572 having an expandable cone 574. Cone 574 includes an orifice 576 and is configured so that gas flow may pass through orifice 576 as well as around cone 574 when the flow rate is low as shown in FIG. 52. When the flow rate is increased, cone 574 expands to provide a seal against housing 572 so that gas flow is only permitted through orifice 576.

Figure 53A:
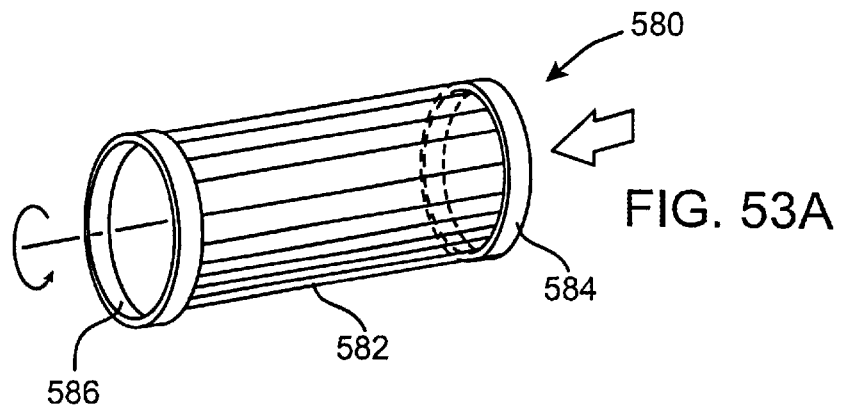
FIGS. 53A and 53B illustrate an iris type flow regulator according to the invention.
Figure 53B:
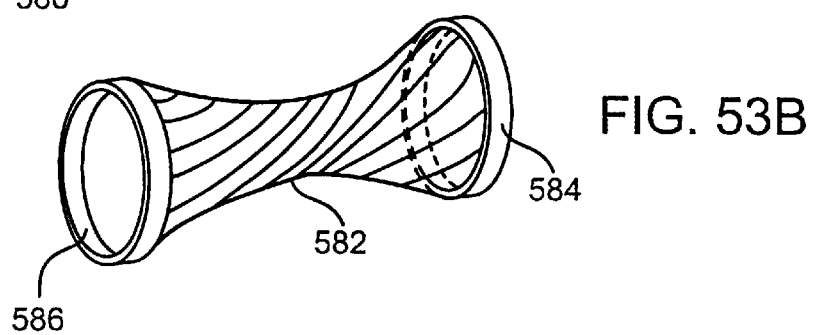

FIGS. 53A and 53B illustrate a flow regulator 580 that comprises in iris valve 582. One end 584 may be fixed and another end 586 may be rotated to move iris valve 582 to the position shown in FIG. 53B. In this way, the flow rate through valve 582 may be regulated.

Figure 54:
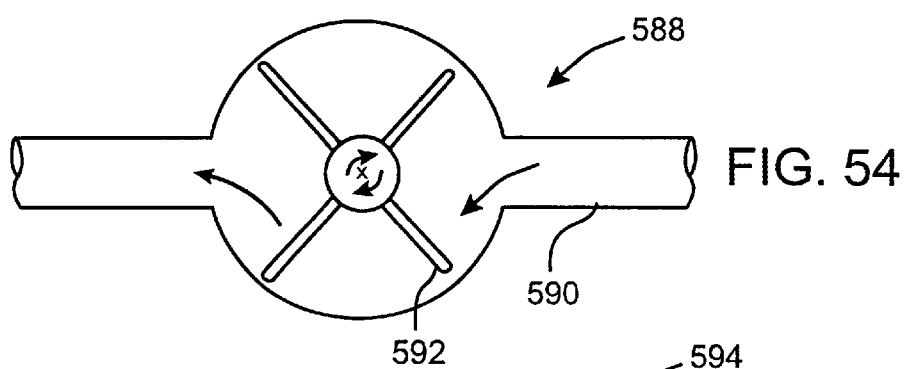
FIG. 54 illustrates a paddle wheel type flow regulator according to the invention.

FIG. 54 illustrates a flow regulator 588 that comprises a housing 590 having a paddle wheel 592 that is rotatable in only one direction as shown by the arrows. Paddle wheel 592 is pivotally connected to housing 590 by a frictional connection that may be adjusted to regulate the amount of gas flow through housing 590. By being rotatable in only one direction, paddle wheel 592 also serves as a check valve.

Figure 55A:
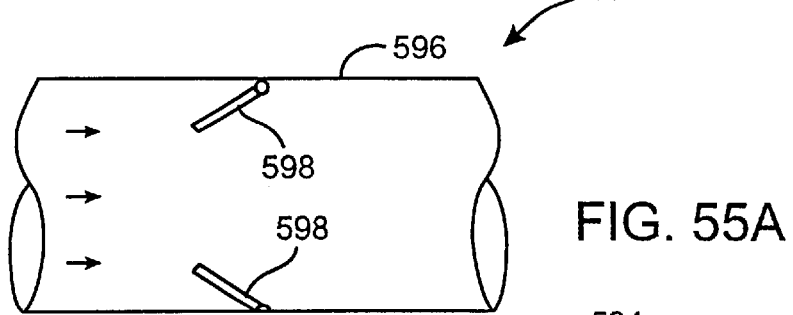
FIGS. 55A and 55B illustrate a flap type flow regulator according to the invention.
Figure 55B:
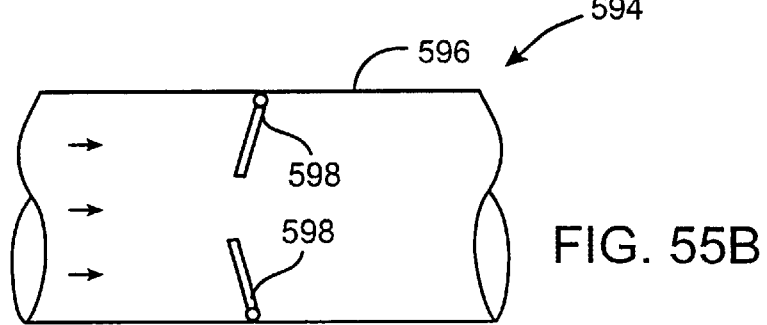

FIGS. 55A and 55B illustrate a flow regulator 594 comprising a tubular housing 596 having pivotal flaps 598. Flaps 598 are configured to close when experiencing a high gas flow as illustrated in FIG. 55B to reduce the flow rate through housing 596.

Another type of flow regulator comprises a valve that is constructed of a flexible material, such as a soft elastomer, e.g., a silicone rubber, that limits the flow to a certain rate while also preventing flow in the opposite direction. Such a valve is also self-resetting, requiring no mechanical assistance. Such valves have an orifice that permits the flow of air through the valve in response to an applied vacuum, and one or more collapsible walls surrounding the orifice such that an increased vacuum pressure level results in reduction of orifice area and correspond higher resistance to flow. One feature of such valves is that they may be relatively inexpensive to construct. One particular example of such a valve is described in U.S. Pat. No. 5,655,520, the complete disclosure of which is herein incorporated by reference.

Figure 56A:
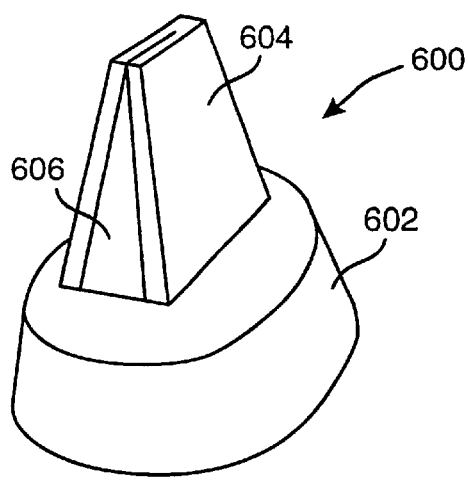
FIGS. 56A and 56B illustrate an elastomeric duck bill type flow regulator according to the invention.
Figure 56B:
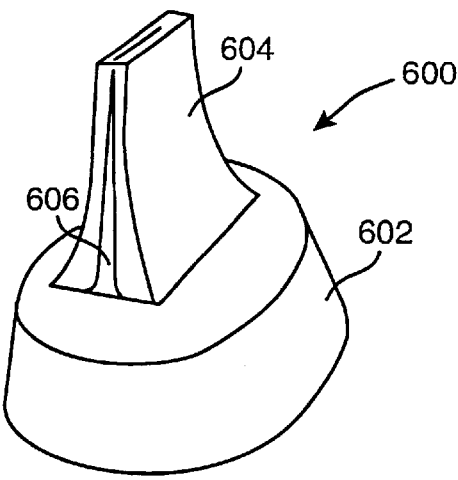

FIGS. 56A and 56B illustrate one embodiment of such a flow regulator 600. Flow regulator comprises an elastomeric body 602 having a duckbill valve 604 that includes an orifice 606. In FIG. 56A, the flow rate is low and orifice 606 is fully opened. When the flow rate increases, valve 604 begins to close as shown in FIG. 56B to limit the flow.

Figure 57:
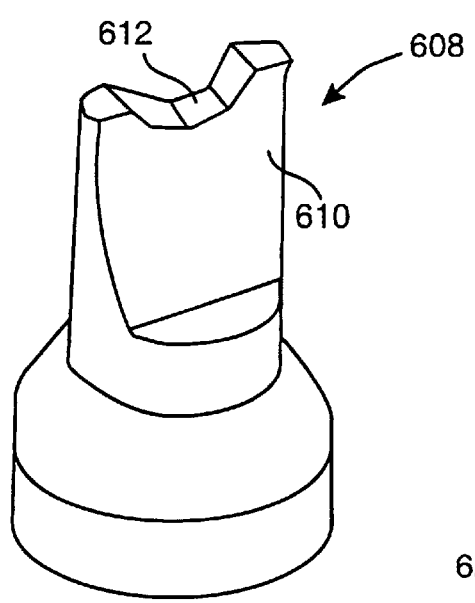
FIGS. 57–59 illustrate alternative elastomeric duck bill type flow regulators according to the invention.
Figure 58:
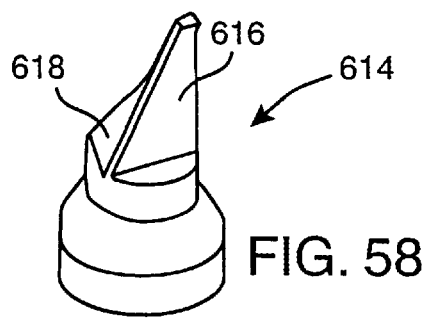
Figure 59:
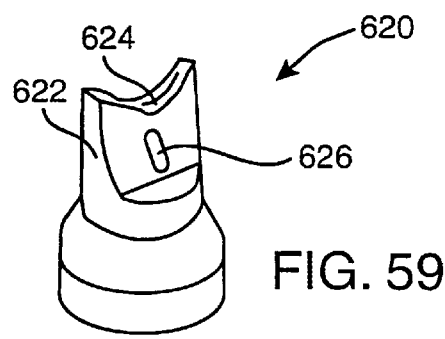

Other examples of such flow regulators are shown in FIGS. 57–59. In FIG. 57, a flow regulator 608 has a duckbill valve 610 with a top orifice 612. FIG. 58 illustrates a flow regulator 614 having a duckbill valve 616 with an orifice 618 extending from the top and down the side. FIG. 59 illustrates a flow regulator 620 having a duckbill valve 622 with a separate top orifice 624 and a side orifice 626.

After the flow rate through the aerosolization device has been regulated for a certain time period, the device may be configured to permit an increased flow rate. In this way, the user may fill his or her lungs with a sufficient volume of air needed to carry the aerosol to the deep lung. For example, following regulation of the flow rate, the device may be configured to permit the user to comfortably fill his or her lungs as the user continues to inhale through the device. Typically, the user may be permitted to fill their lungs at a comfortable rate once an initial volume of about 500 mL has been inhaled at the regulated flow rate. This assumes that after about 500 mL of inhaled air, the drug has traveled past the anatomical dead space.

To provide such a feature, various timers or flow integrators may optionally be incorporated into the aerosolization devices of the invention. Such flow integrators have one or more moving members that move based on the volume of flow through the device. In this way, when the initial (regulated) volume has been inhaled, the member has moved sufficient to open another gas channel to permit increased gas flow. For example, the flow integrator may be an airfoil flap made of a film such as a polymer film having a thickness between 0.005 and 0.020 inches and preferably having a viscoelastic or other time-dependent behavior. Airflow over the airfoil flap induces aerodynamic lift. The air foil flap can be configured to allow access to a parallel flow path after a predetermined volume of air flows over the flap.

Figure 60:
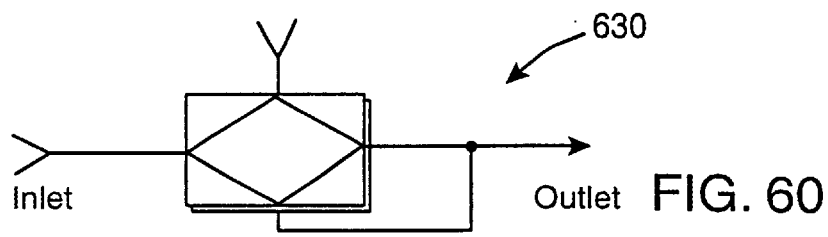
FIG. 60 schematically illustrates a flow through type flow integrator according to the invention.

FIG. 60 schematically illustrates a flow through type flow integrator 630 that is configured to move based on the flow velocity, assuming a low pressure drop. Integrator 630 moves based on the pressure differential between the ambient and the inlet, which can vary significantly even though the flow rate remains constant when using a flow regulator as described above. One advantage of integrator 630 is that it provides an accurate volume measurement.

Figure 61:
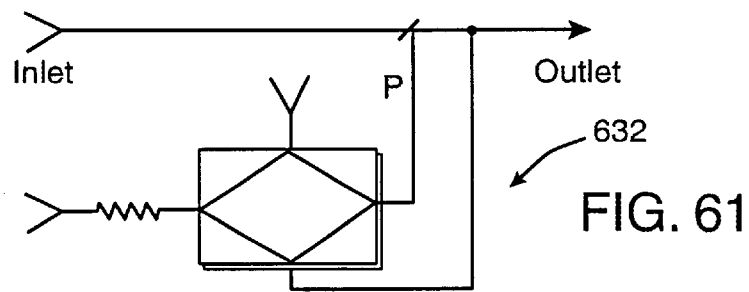
FIG. 61 schematically illustrates a flow-by type flow integrator according to the invention.

FIG. 61 schematically illustrates a flow-by type integrator 632 that is parallel to the main flow path. Optionally, integrator 632 may trigger a switch at the end of travel to open a parallel flow path with low flow resistance.

Figure 62A:
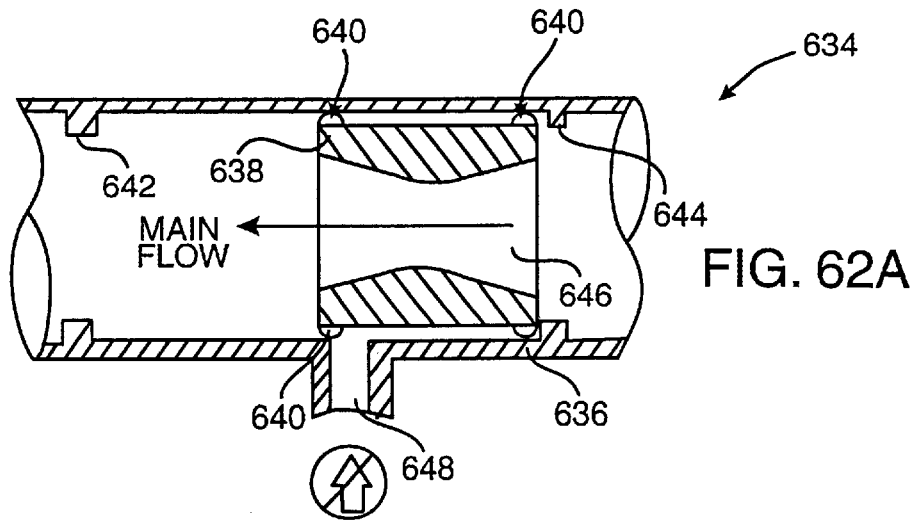
FIGS. 62A and 62B illustrate a flow through shuttle type flow integrator according to the invention.
Figure 62B:
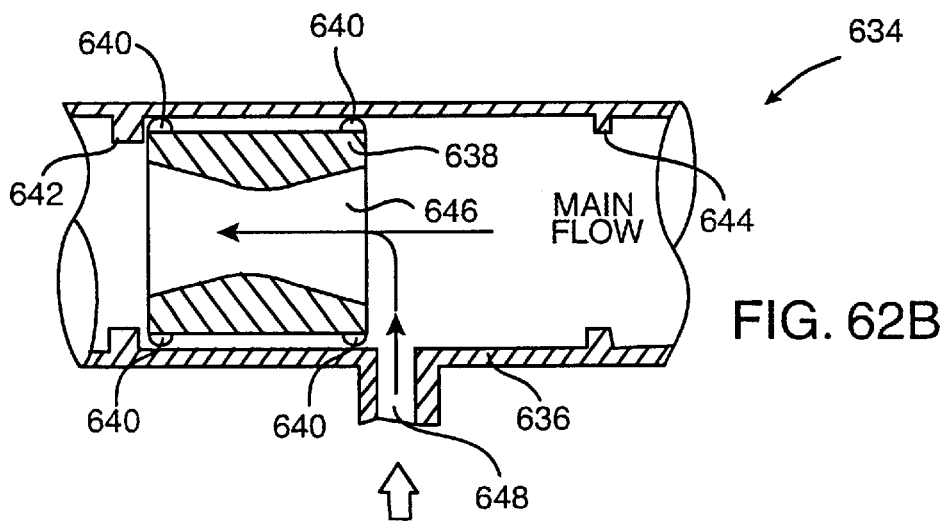

FIGS. 62A and 62B illustrate a flow through shuttle type flow integrator 634 that comprises a tubular housing 636 and a shuttle 638 that is slidable within housing 636. Conveniently, skirt seals 640 provide a seal between housing 636 and shuttle 638 while still permitting shuttle 638 to slide. Stops 642 and 644 are also provided to limit travel of shuttle 638. In FIG. 62A, shuttle 638 is in the closed position where the main flow through the aerosolization device passes through an opening 646 in shuttle 638, and a parallel flow through a channel 648 is prevented by shuttle 638. Shuttle 638 moves through housing 636 in response to the velocity of the gas flowing through housing 636. The drag force, and therefore the speed at which shuttle 638 moves, is proportional to the flow velocity. As shown in FIG. 62B, shuttle 638 moves past channel 648 after a certain amount of time to permit increased flow through housing 636.

Figure 63:
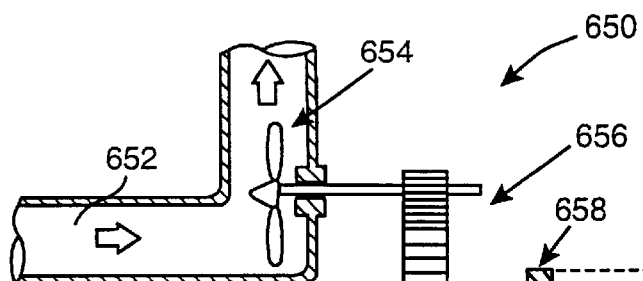
FIG. 63 illustrates an impeller type flow integrator according to the invention.
Figure 64:
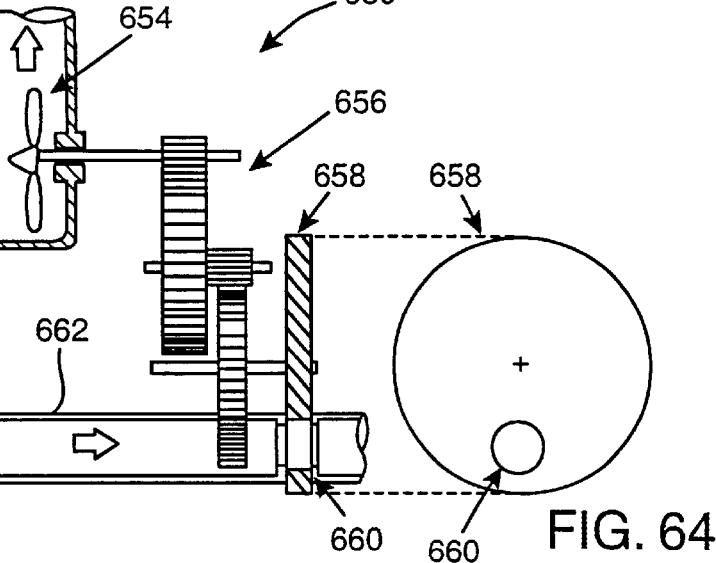
FIG. 64 is an end view of a cam of the flow integrator of FIG. 63.

FIG. 63 illustrates a flow integrator 650 that comprises a tubular housing 652 through which the main gas flow through the aerosolization device passes. Disposed within housing 652 is an impeller 654 that is coupled to a gear reduction 656. In turn, gear reduction 656 is coupled to a cam 658 that has a hole 660 as also shown in FIG. 64. Cam 658 is rotatable through a tubular housing 662 that provides a parallel flow path through the aerosolization device. In operation, the user inhales to provide gas flow through housing 652 which turns impeller 654. In turn, cam 658 is rotated through gear reduction 656. When cam 658 reaches a specific angle, hole 660 is aligned with housing 662 to open a parallel flow path for the chase air.

Figure 65:
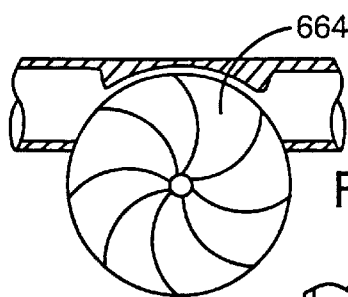
FIG. 65 illustrates a paddle wheel that may be used in the flow integrator of FIG. 63.

As an alternative to the impeller 654, a paddle wheel 664 may be used as illustrated in FIG. 65. In such an embodiment, paddle wheel 664 may be coupled to gear reduction 656 in a manner similar to that previously described.

Figure 66A:
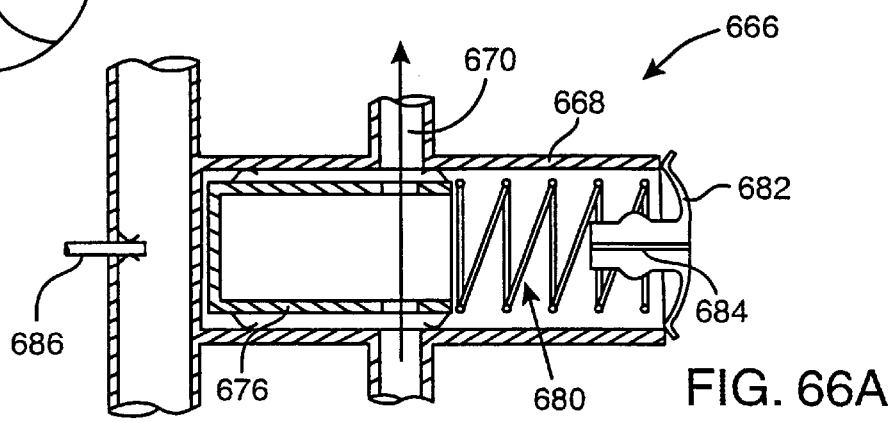
FIGS. 66A and 66B illustrate a shuttle type flow integrator according to the invention.
Figure 66B:
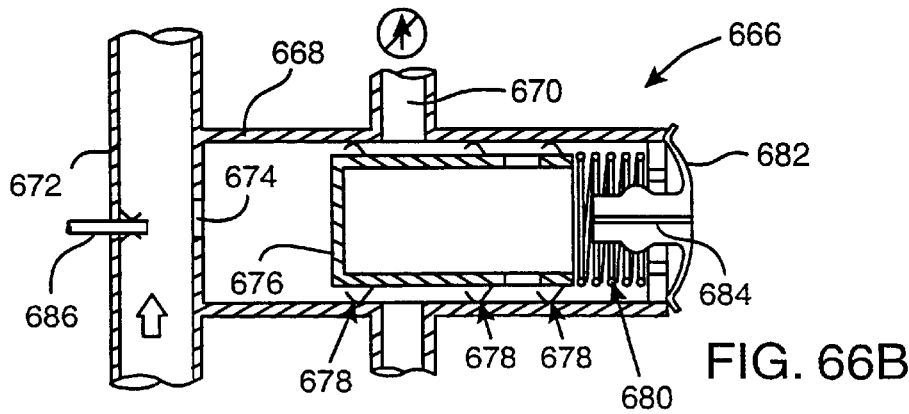

FIGS. 66A and 66B illustrate a flow integrator 666 that comprises a tubular housing 668 having a parallel flow path 670. Coupled to housing 668 is a main flow path 672. An opening 674 places housing 668 and flow path 672 in fluid communication. Disposed within housing 668 is a shuttle 676 having skirt seals 678 to provide a seal between shuttle 676 and housing 668. A spring 680 is disposed between housing 668 and shuttle 676, and an umbrella valve 682 with a bleed hole 684 extends through housing 668.

As shown in FIG. 66B, shuttle 676 prevents parallel gas flow through flow path 670 when the user first begins to inhale. Shuttle 676 moves under force of spring 680, damped by bleed hole 684 (or alternatively by controlled leakage around shuttle 676). Shuttle 676 moves faster when the pressure differential between the inlet side (having bleed hole 684) and the outlet side (having opening 674) is increased due to the vacuum created by the user. When shuttle 676 reaches the end of its travel, parallel flow path 670 is opened for the chase air. A reset rod 686 may then be used to reset shuttle 676 to the position shown in FIG. 66B.

Figure 67:
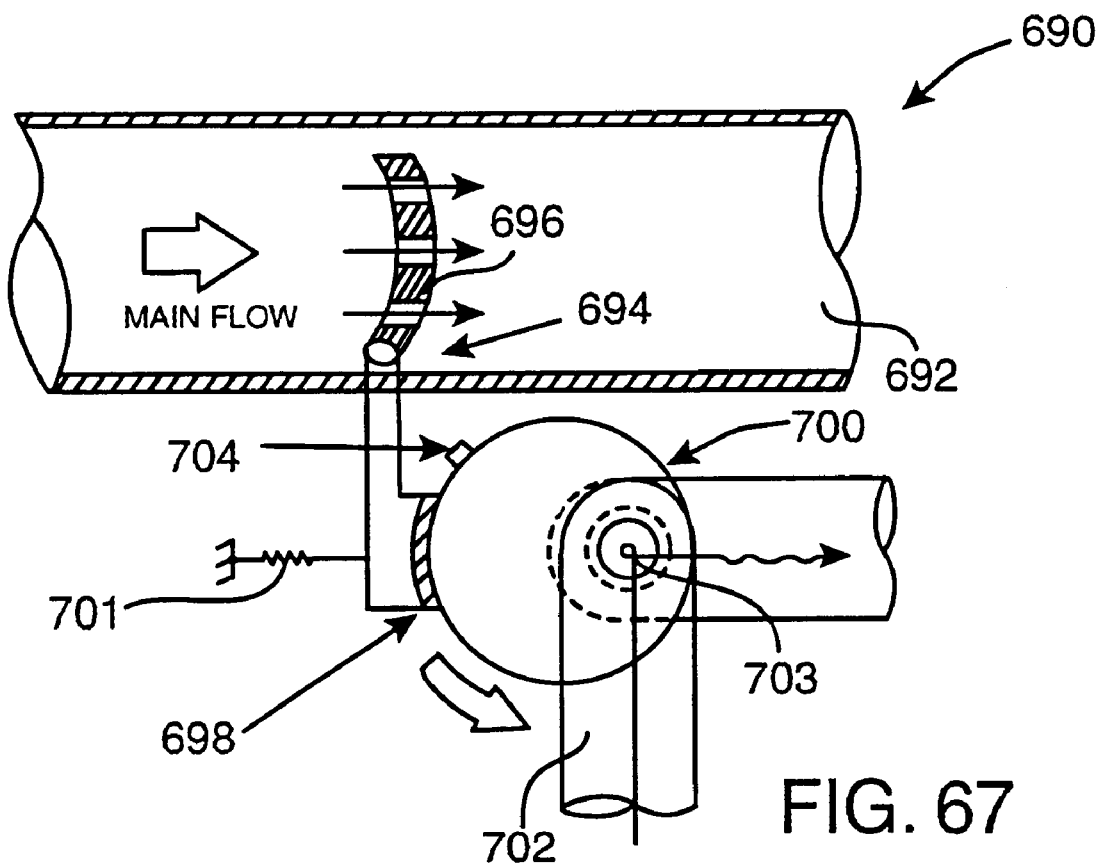
FIG. 67 illustrates a brake timer flow integrator according to the invention.
Figure 68:
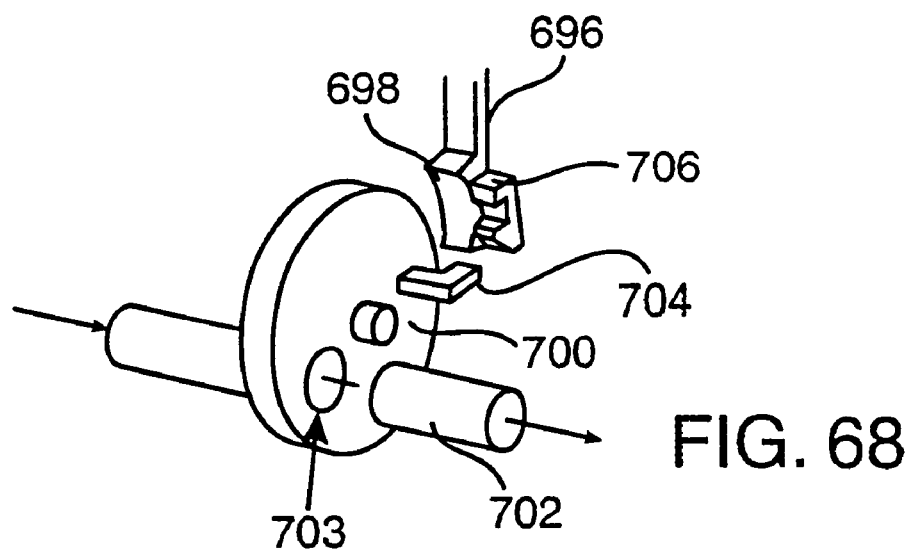
FIG. 68 illustrates a brake and a wheel of the flow integrator of FIG. 67.

FIG. 67 illustrates a flow integrator 690 comprising a tubular housing 692 that serves as a main flow path. A brake system 694 having a pivotal brake arm 696 extends into housing 692. Coupled to brake arm 696 is a brake pad 698 as also shown in FIG. 68. Integrator 690 further comprises a wheel 700 that moves through a tubular housing 702 that serves as a parallel flow path for the chase air. Wheel 700 has a hole 703 that aligns with housing 702 when wheel 700 is at a specified angle. Brake uarm 696 is spring loaded against wheel 700 with a spring 701. Also coupled to wheel 700 is a trigger 704 that fits within a groove 706 of brake arm 696.

To operate integrator 690, the user winds a spring (not shown) which rotates wheel 700 at a constant rate when released. When the user creates a main flow through housing 692, brake arm 696 pivots to release trigger 704 and brake pad 698. Wheel 700 then rotates at a constant rate until hole 703 becomes aligned with housing 702, thereby opening a parallel flow path for the chase air.

Figure 69:
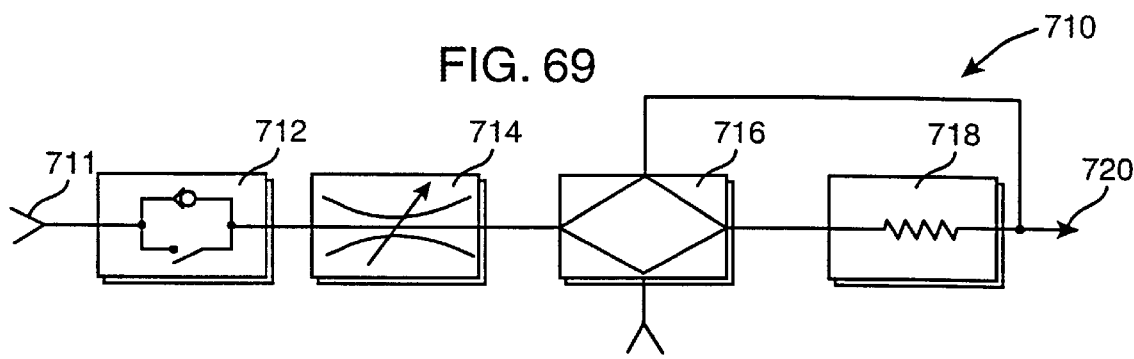
FIG. 69 schematically illustrates an aerosolization system having various components arranged in series according to the invention.

The threshold valves, flow regulators and, optionally, flow integrators of the invention may be arranged in a variety of configurations within an aerosolization device. For example, FIG. 69 illustrates an aerosolization system 710 where the various components are arranged in series. System 710 comprises, in series, an inlet 711, a threshold valve 712, a flow regulator 714, a flow integrator 716 of the flow through type, a receptacle 718 for holding a powdered medicament, and an outlet 720. The total resistance of receptacle 718 may be configured to be less than or equal to the resistance of the rest of the system until flow integrator 716 opens. Conveniently, the order of threshold valve 712, flow regulator 714 and flow integrator 716 (if a flow through type integrator) may be interchanged. Alternatively, flow integrator 716 may be a flow-by type integrator that may be parallel to receptacle 718. Receptacle 718 may be last in the series to prevent the drug from depositing on the other components. Conveniently, threshold valve 712, flow regulator 714 and flow integrator 716 may be integrated into one mechanism.

FIG. 70 illustrates an aerosolization system 722 that comprises an inlet 724, a threshold valve 726, a flow regulator 728, a receptacle 730, a flow integrator 732 of the flow-by type, and an outlet 734. Integrator 732 is arranged parallel to threshold valve 726 and regulator 728. With system 722, the maximum system resistance may be less than or equal to the resistance of receptacle 730. In this way, some users may achieve flow rates above 10 L/min. Integrator 732 operates from the pressure differential between ambient and outlet 734. Conveniently, threshold valve 726 and flow regulator 728 may be integrated.

FIG. 71 illustrates an aerosolization system 736 that comprises an inlet 738, a threshold valve 740, a flow integrator 742 of the flow through type, a flow regulator 744, a receptacle 746 and an outlet 748. With system 736, the order of threshold valve 740 and flow integrator 742 may be changed. Further, the maximum system resistance may be less than or equal to the resistance of receptacle 746. Use of the flow through type of integrator provides a more accurate volume measurement since it operates as a result of the flow rate through it. System 736 also allows for integration of threshold valve 740 and flow regulator 744, or flow integrator 742 and flow regulator 744. In one aspect, system 736 may be configured so that flow integrator 742 does not restrict the flow spike which occurs after threshold valve 740 opens so that the high flow rate passes entirely through receptacle 746 to disperse the powder.

FIGS. 72–78 illustrate one particular embodiment of an aerosolization device 750 that incorporates a threshold valve, a flow regulator and a flow integrator. Device 750 comprises a housing 752, a door 754 that is pivotally coupled to housing 752 by a shaft 756 and a pivotable mouthpiece 758. As best shown in FIG. 73, door 754 may be opened to permit a receptacle 760 (shown already opened) to be inserted into device 750. Device 750 further includes a an extraction tube 762 that is in commination with mouthpiece 758 to permit the drug that is extracted from receptacle 760 to pass into mouthpiece 758. A deagglomerator 764 is provided in mouthpiece 758 to deagglomerate any agglomerated powder the is extracted from receptacle 760. Conveniently, deagglomerator 764 also serves as a shaft about which mouthpiece 758 pivots. Coupled to extraction tube 762 is a cutter 766 that pierces receptacle 760 when door 754 is closed so that the drug may be extracted.

Incorporated into door 754 is a threshold valve 768 that comprises a membrane 770 having an opening 772. A valve member 774 having a ball 776 that is movable through opening 772 once a threshold vacuum that is produced by the user is met or exceeded. In operation, a user inhales from mouthpiece 758 which creates a vacuum in tube 762 and in a passage 778 that is in communication with a right hand side of membrane 770. Once the threshold vacuum pressure is met or exceeded, ball 776 is pulled through opening 772 to permit outside air to enter into a region 780 of door 754 through a vent (not shown). In this way, air flows through receptacle 760 to extract the powdered drug where it is delivered to mouthpiece 758. Conveniently, device 750 further includes a cam 782 that moves ball 780 back through opening 772 when door 754 is opened and closed to reset the valve.

Device 750 further includes a flow regulator 784 to limit the air flow through tube 762 to a certain rate. Regulator 784 comprises a tapered opening 786 into which ball 780 is drawn as the vacuum created by the user increases. A spring 785 controls the amount of vacuum require to close opening with ball 776. Hence, if the flow rate becomes too great, a parallel flow path 788 that leads back into tube 762 is closed off by ball 780. In this way, the only air passing through tube 762 must pass through receptacle 760 as previously described. This flow path has sufficient resistance such that the flow is limited to the desired rate. If the user does not create a vacuum sufficient to close flow path 788, the air flow is permitted through two parallel flow paths.

Device 750 further includes a flow integrator 790 to permit an increased flow rate once a certain amount of time has passed so that the user may comfortably fill their lungs after the flow has been regulated for a specified time. Flow integrator 790 comprises a clutch diaphragm 792 upon which a spool 794 rests. Spool 794 is biased to rotate by a torsional spring 796. In this way, when diaphragm 792 is disengaged from spool 794, spool 794 rotates until an opening (not shown) in spool 794 becomes aligned with an opening 798 (see FIG. 76) in tube 762. At this point, ambient air is able to flow through a parallel flow path and into tube 762 to permit the user to comfortably fill their lungs with air.

Diaphragm 792 is configured to lower to release spool 794 due to the vacuum created in flow path 788 as the user inhales from mouthpiece 758 as previously described. The rate of spool rotation (and hence the time required to open the parallel flow path) is determined by a damping reservoir 800 which contains a damping grease. A fixed member 802 fits within reservoir 800 to regulate the rate of spool rotation as member 802 frictionally engages the damping grease. Although not shown, device 750 may include a reset lever to reset spool 794 after use.

Figure 80:
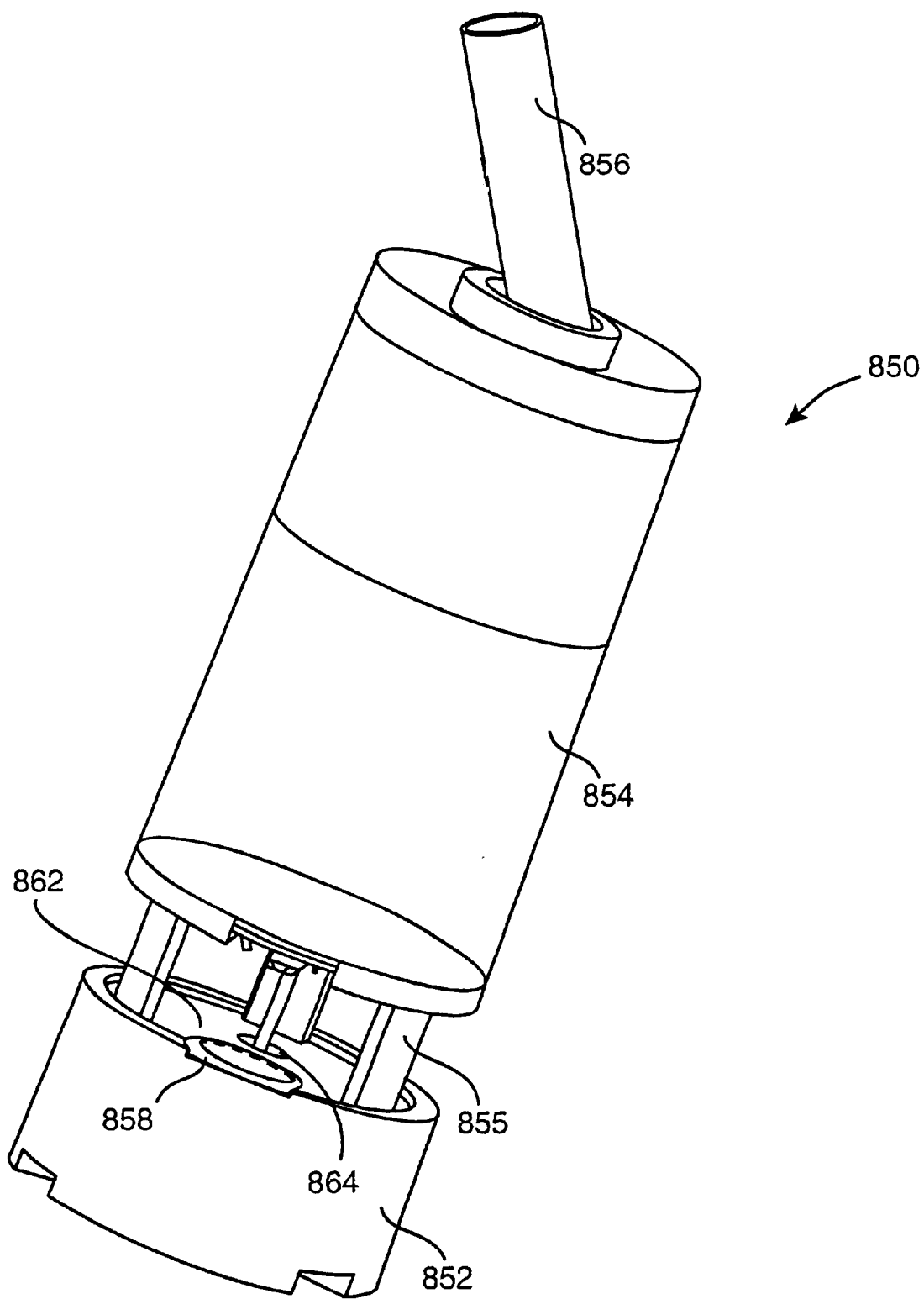
Figure 81:
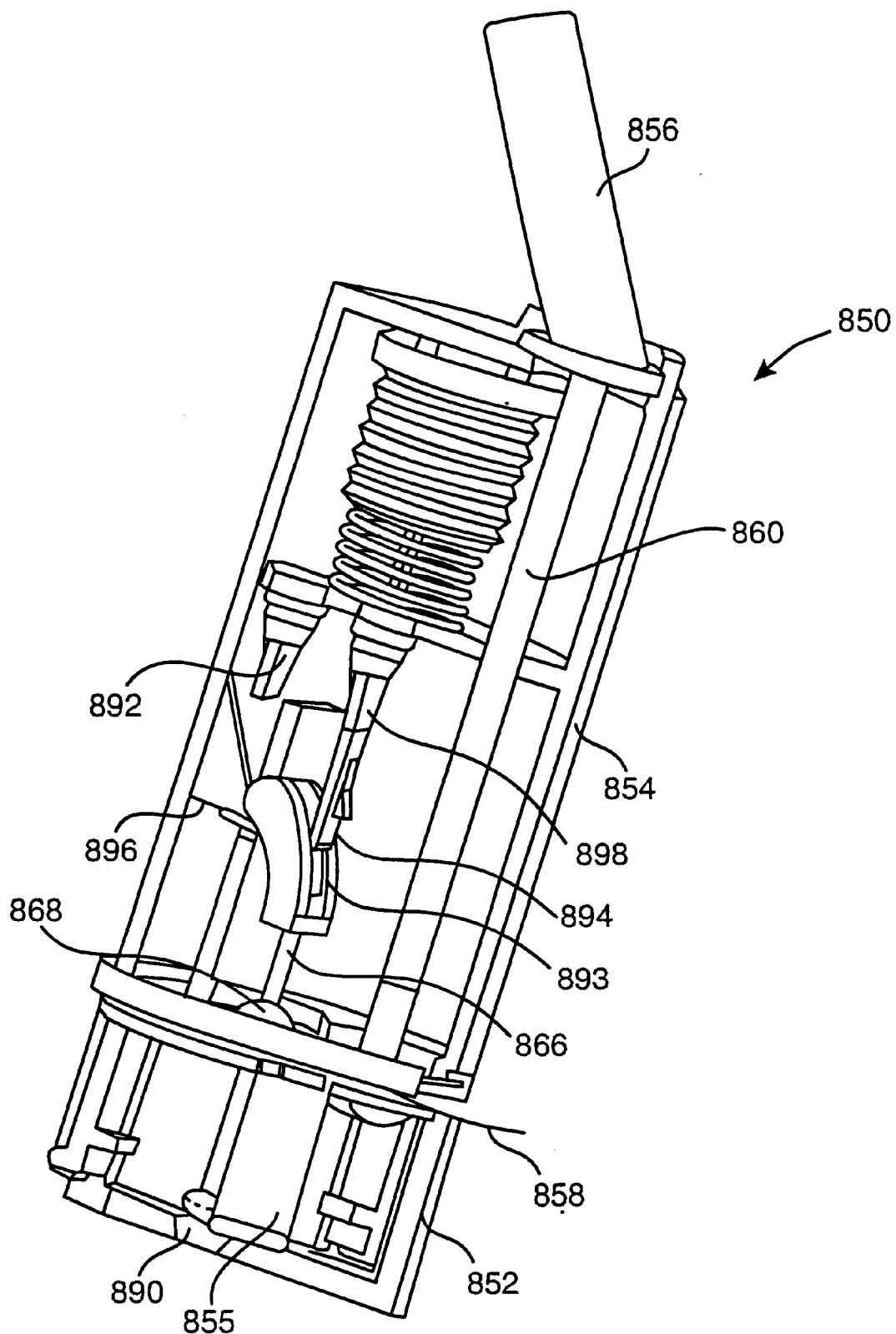

FIGS. 79–83 illustrate another embodiment of an aerosolization device 850 that comprises a lower housing 852, an upper housing 854 and a rotatable mouthpiece 856. As best shown in FIG. 80, lower housing 852 may be separated from upper housing 854 to permit a drug containing receptacle 858 to be inserted into device 850. A lower housing catch 855 is provided to limit the travel of housing 852 relative to upper housing 854. Coupled to mouthpiece 856 is a tube 860 having a cutting mechanism 862 to open receptacle 858 when receptacle 858 is inserted and lower housing 852 is placed adjacent upper housing 854.

Disposed across lower housing 852 is a membrane 862 having an opening 864. Extending through opening 864 is a latch 866 having a ball 868. Positioned below latch 866 is a hole 890 in lower housing 852. Such a configuration provides a threshold valve for device 850. In this way, when a user inhales from mouthpiece 856, a vacuum is created in tube 860 and in the space above membrane 862. When the user creates a sufficient vacuum, ball 868 is pulled through opening 864 in membrane 862 to permit outside air to flow through hole 890, through opening 864, through receptacle 858 and up through tube 860 where the aerosolized drug exits through mouthpiece 856.

Once the drug has been aerosolized, the flow of air through device 850 is regulated to be less than a certain rate in part through use of an elastomeric duckbill valve 892. More specifically, air is permitted to flow through two flow paths, i.e. through valve 892 and through receptacle 858 provided the flow rate is below the specified amount. As the air flow rate increases, valve 892 begins to close to prevent air from flowing through this flow path. The only available air path is then through receptacle 858 which provides sufficient resistance to limit the flow to a certain rate.

Figure 82:
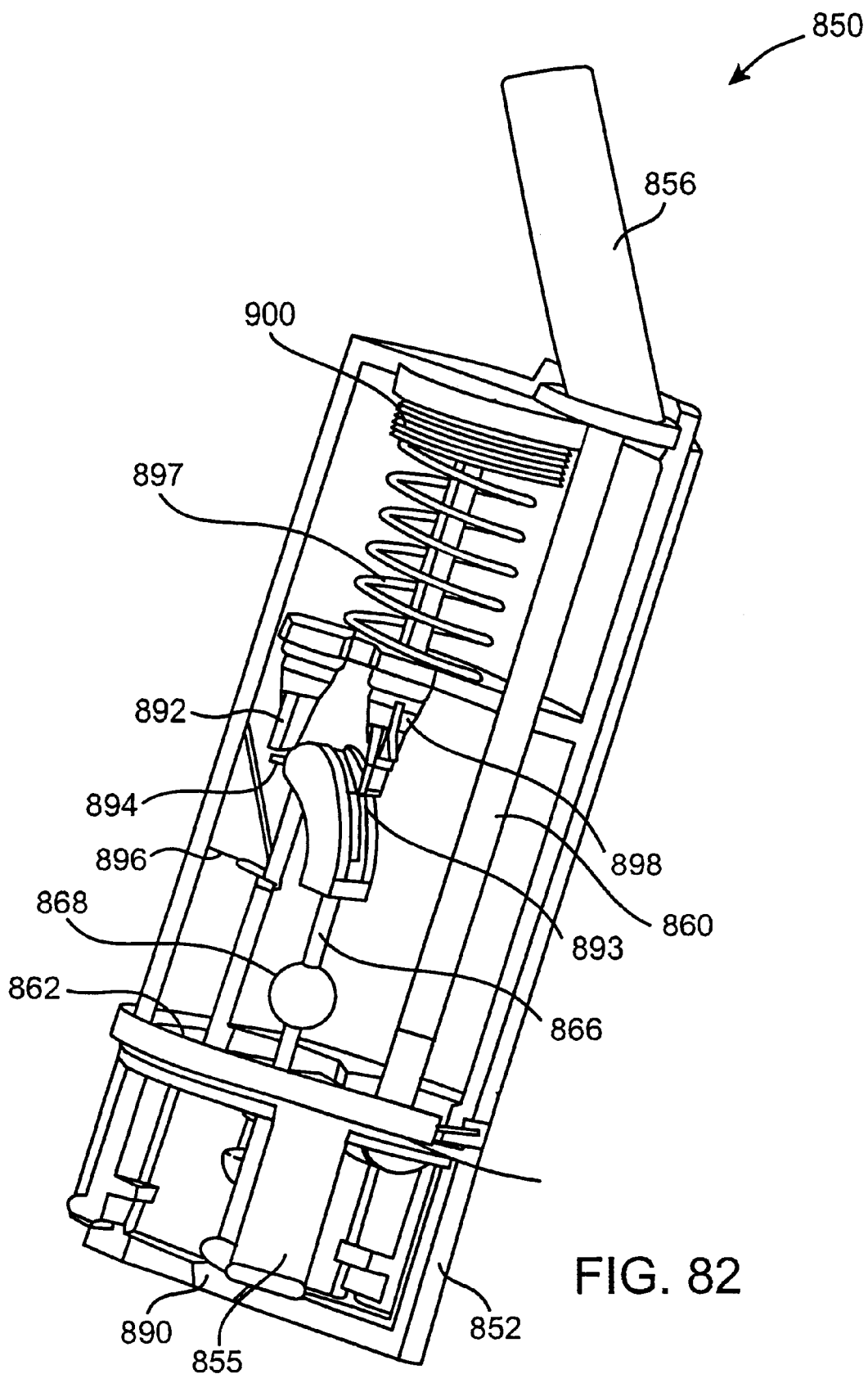
Figure 83:
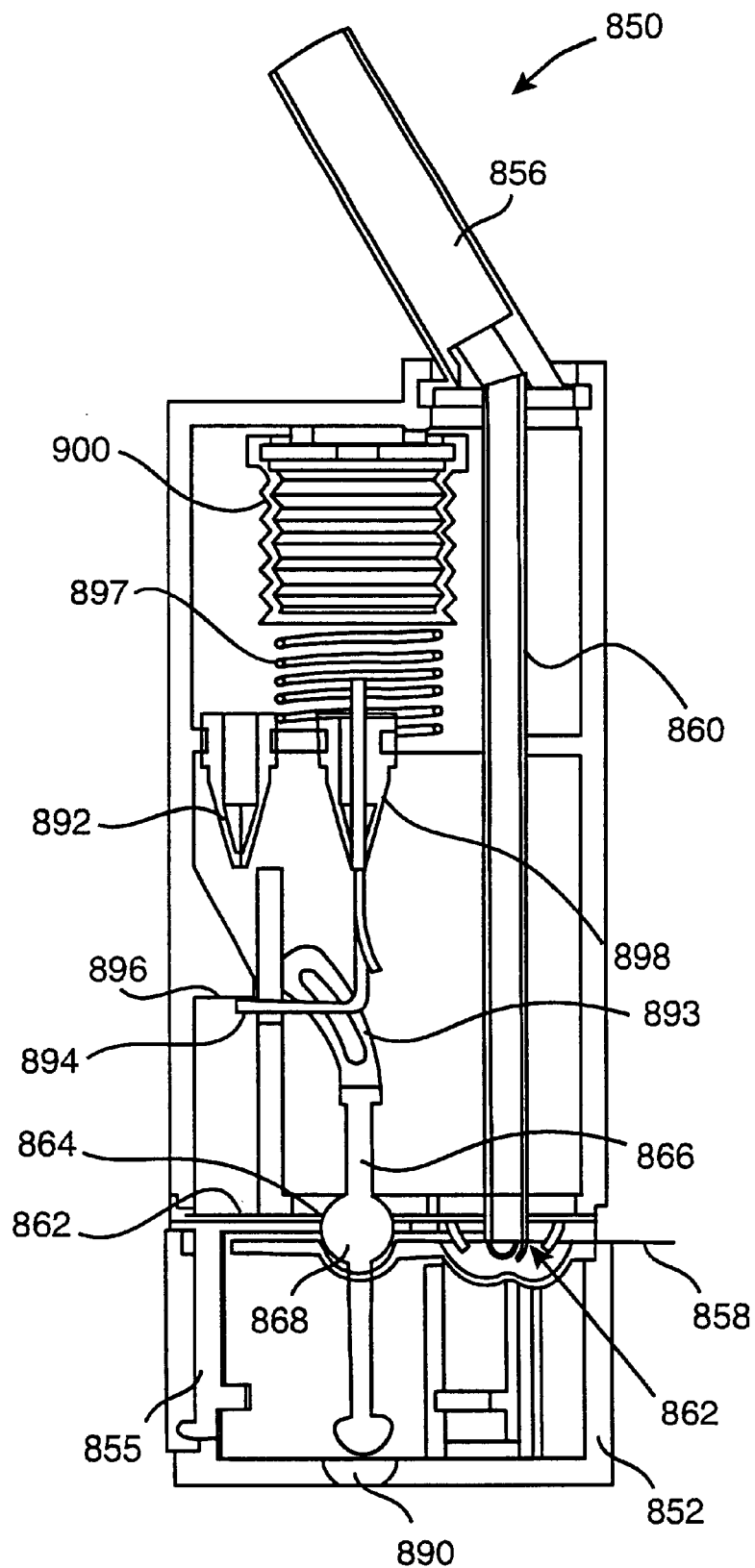
Figure 84:
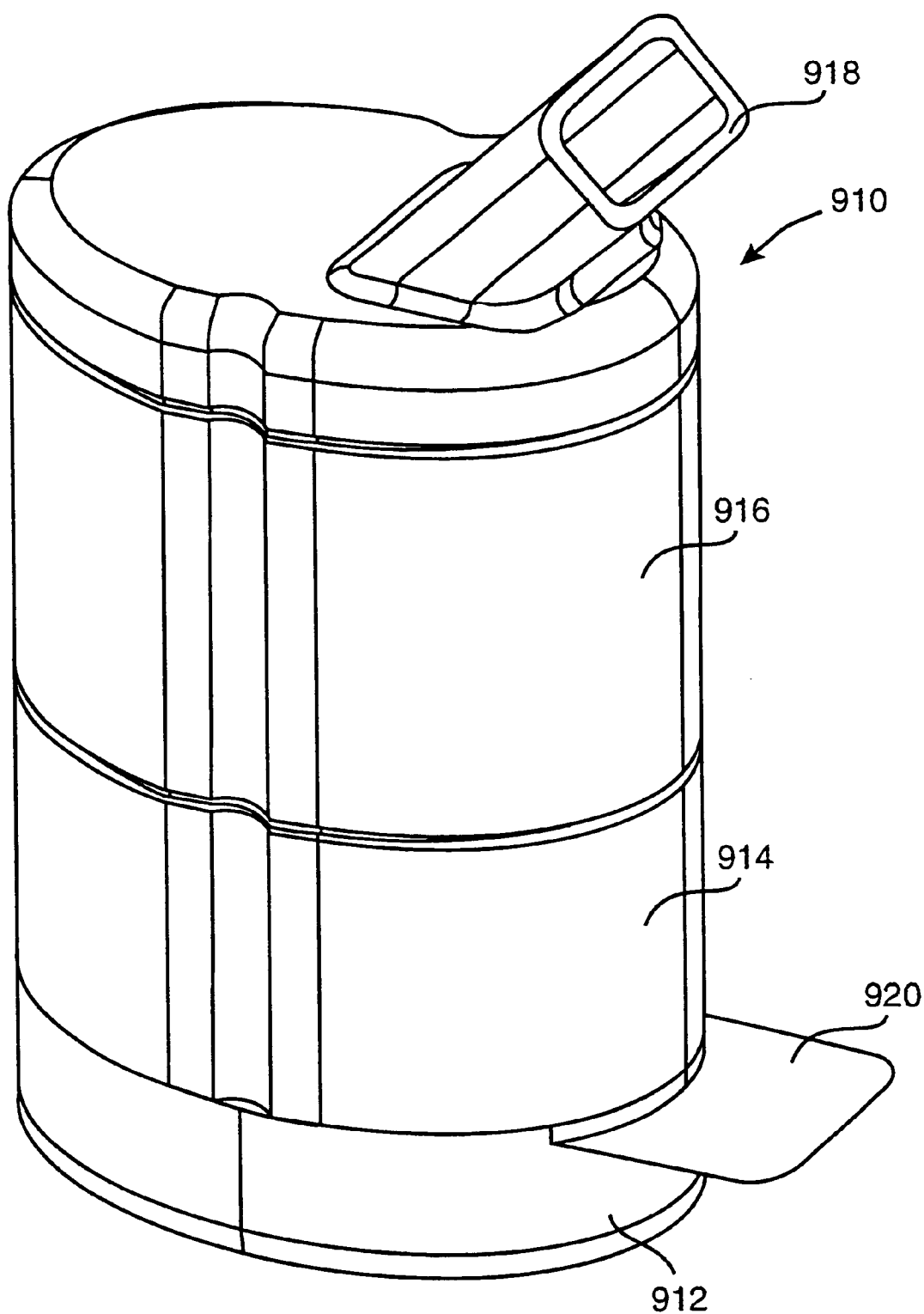

Coupled to a cam 893 of latch 866 is a bypass spreader 894 that is engaged with a stop 896. Spreader 894 is coupled to a spring 897 and is also slidable within a bypass duckbill valve 898. As the user continues to inhale through mouthpiece 856, cam 893 of latch 866 moves spreader 894 away from stop 896. This causes spring 897 to expand as shown in FIG. 82 to compress a bellows 900 and to spread valve 898 which is normally closed. In this way, after a certain period of time, valve 898 is opened to provide another flow path so that more ambient air may flow through device 850 through hole 890. In this manner, the user is permitted to comfortably fill their lungs after the initial drug delivery. The rate of compression of bellows 900 is controlled by filling bellows 900 with a known volume of air and by providing a small orifice in bellows 900. In this way, the rate of compression is controlled by the time required to force the air out through the orifice once spreader 894 is released from stop 896.

Figure 85:
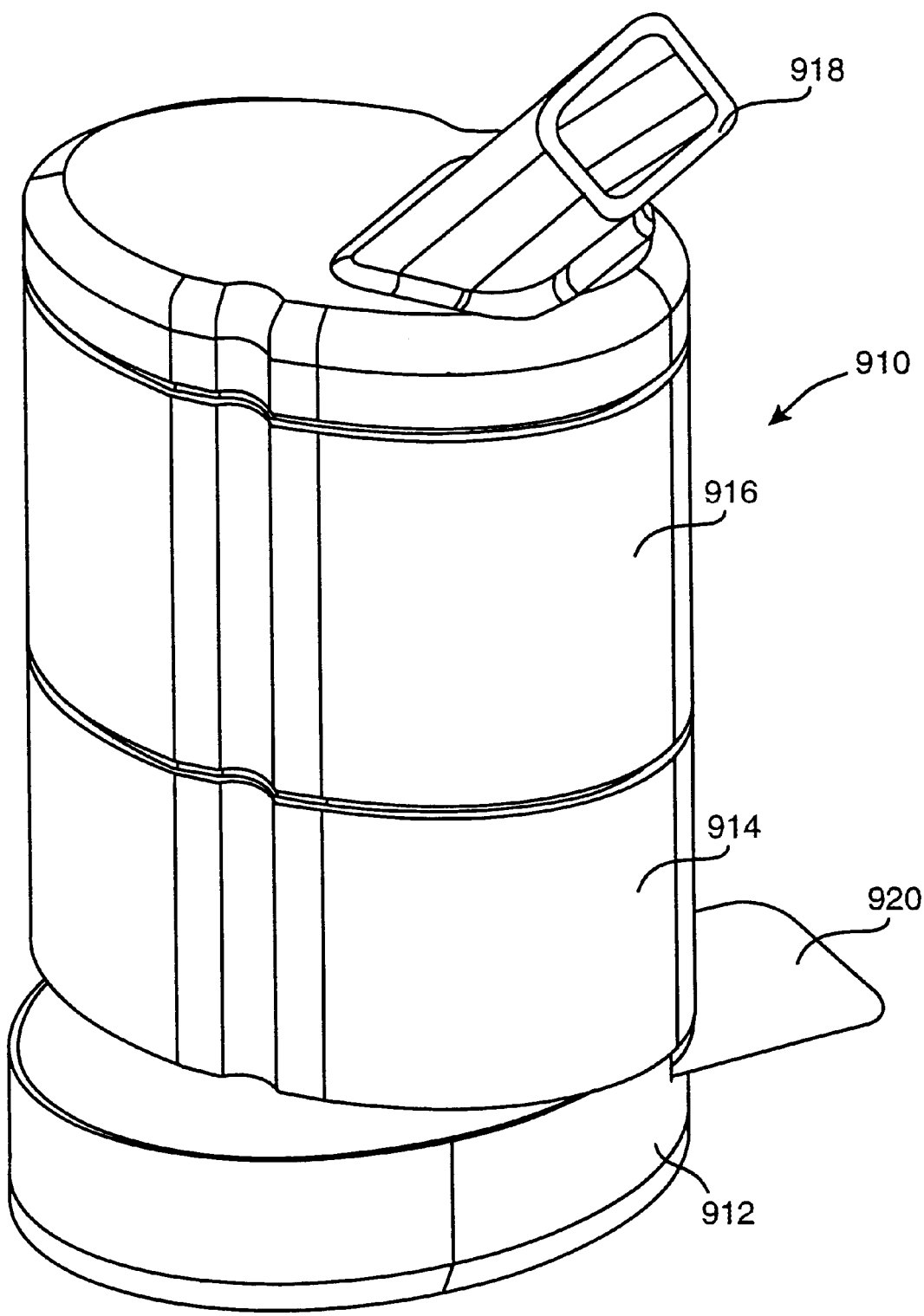
Figure 86:
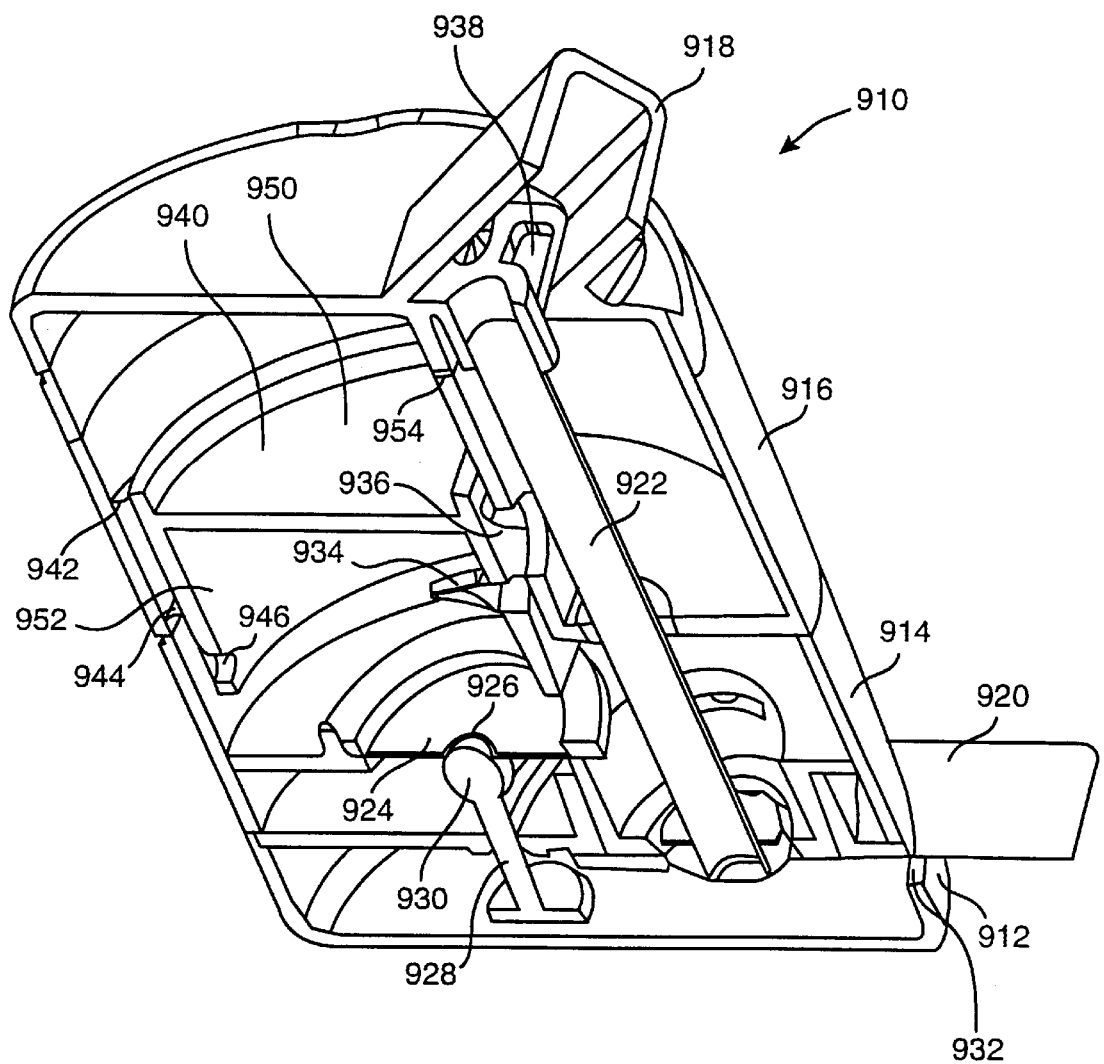
Figure 87:
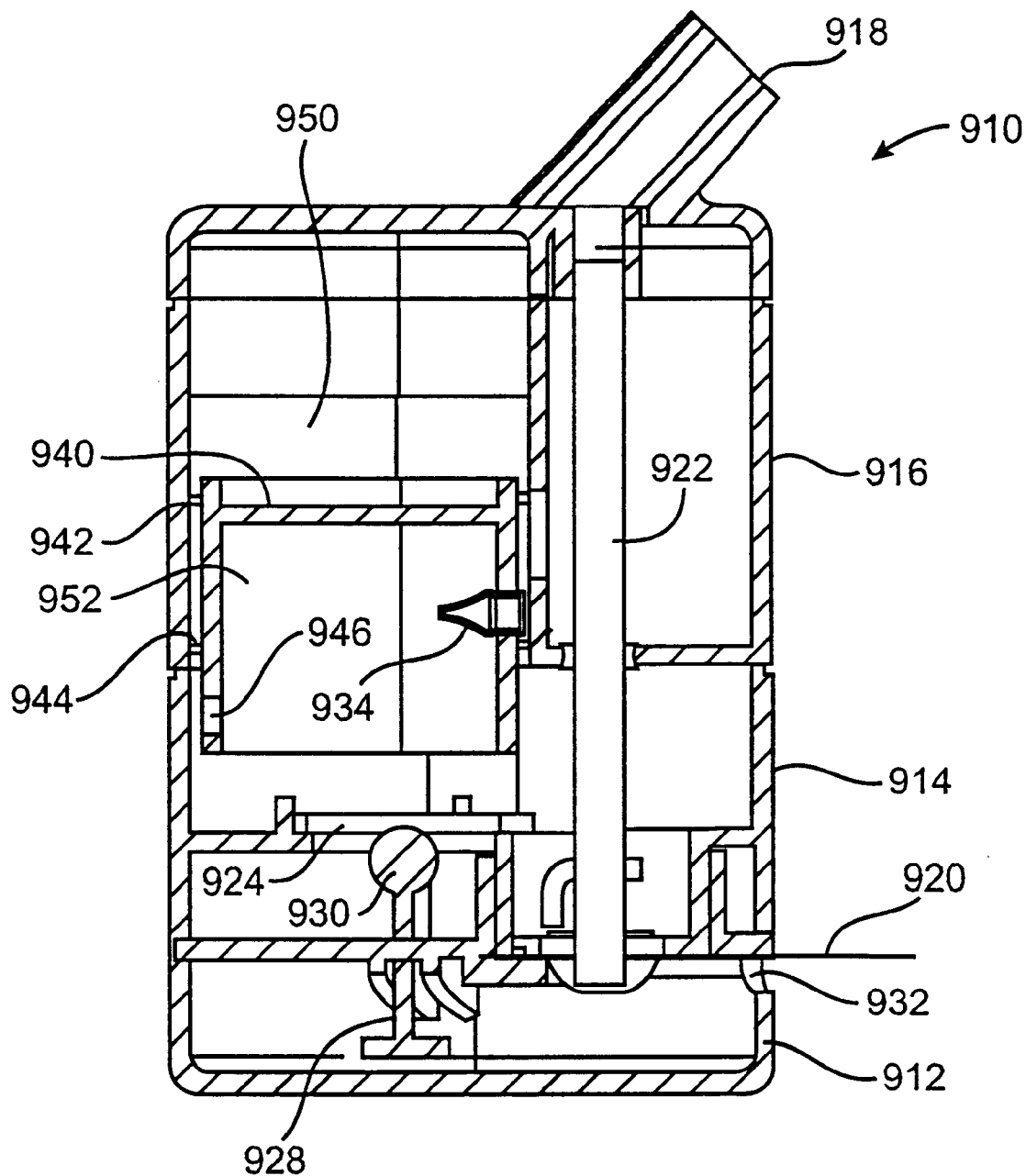

FIGS. 84–87 illustrate another embodiment of an aerosolization device 910 that comprises a lower housing 912, a middle housing 914, an upper housing 916 and a mouthpiece 918. Lower housing 912 is movable relative to middle housing 914 to permit a drug containing receptacle 920 to be inserted as illustrated in FIG. 85. Coupled to mouthpiece 918 is a tube 922 that is configured to pierce receptacle 920 to provide access to the drug.

Middle housing 914 includes a membrane 924 having an opening 926. A valve member 928 having a ball 930 is positioned within lower housing 912 and functions as a threshold valve to ensure that a sufficient vacuum is created by the user when initially inhaling the drug. In operation, the user inhales from mouthpiece 918 to create a vacuum within tube 922 and in the space above membrane 924. When a sufficient vacuum has been produced, ball 930 is pulled through opening 926 to permit ambient air to flow into lower housing 912 through a hole 932, through opening 926, through receptacle 920, through tube 922 and out mouthpiece 918. In so doing, the drug is extracted from receptacle 920 and is supplied to the user.

Device 910 is further configured to regulate the flow rate of air through device 910 after ball 930 is pulled through membrane 924. This is accomplished in part by the use of an elastomeric duckbill valve 934 in upper housing 916. As the user continues to inhale, ambient air entering through hole 932 also passes through opening 926 and then through valve 934. The air then travels through an opening 936, an opening 938 and out mouthpiece 918. However, if the flow rate becomes too great, valve 934 closes to prevent air flow through this flow path. As a result, air may only flow through receptacle 920 and tube 922 which, because of their limited size, regulates the flow rate to within a specified rate to permit the aerosolized drug to reach the user's lungs.

After a specified amount of time, device 910 is configured to permit an increased flow of air through device 910 so that the user may comfortably fill their lungs with air. This is accomplished by use of a piston 940 that is coupled to upper housing 916 by a pair of rolling seals 942 and 944. Piston 940 further includes a hole 946 that moves between seals 942 and 944 after a certain amount of time. When reaching this position, the ambient air flowing through opening 932 also through hole 946, through hole 936 and out mouthpiece 918. In this way, an additional flow path is provided to permit the user to comfortably fill their lungs after initial delivery of the drug.

Piston 940 moves due to a pressure differential between a region 950 above piston 940 and a region 952 below piston 940. This pressure differential is produced by a vacuum that is created in region 950 when the user begins to inhale due to a bleed hole 954 that is in communication with region 950. The size of bleed hole 954 is configured to control the resulting vacuum within region 950, and therefore the rate of upward movement of piston 940.

A variety of techniques may be used to ensure that the user properly positions their mouth over the mouthpiece during use of the aerosolization devices of the invention. For example, a lip guard may be included on the mouthpiece to permit the user to place their lips adjacent the lip guard. As another example, the mouthpiece may include bite or other landmarks. Alternatively, one or more holes may be provided in the side of the mouthpiece. These holes must be covered by the lips in order to create a sufficient vacuum to operate the device. As a further example, the mouthpiece may have a circular-to-elliptical profile. The elliptical portion must be covered by the patient's mouth in order for a sufficient vacuum to be created. Optionally, a tongue depressor may also be used to depress the user's tongue when inhaling from the mouthpiece.

Figure 88:
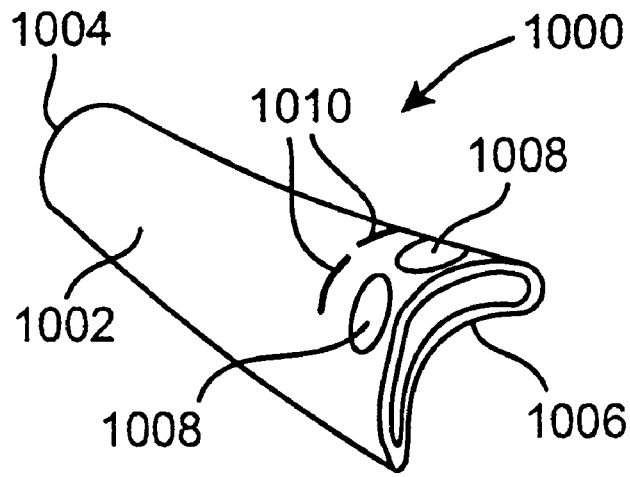

Referring now to FIG. 88, one embodiment of a mouthpiece 1000 will be described. Mouthpiece 1000 comprises a tubular member 1002 having a distal end 1004 that is configured to be coupled to an aerosolization device and an open proximal end 1006. Distal end 1004 has a circular cross sectional profile, while proximal end 1006 has a curved or elliptical cross sectional profile. In this way, the user must place their mouth over mouthpiece 1000 until their lips reach the circular portion in order to create the vacuum needed to operate the aerosolization device. Another mouth position device on mouthpiece 1000 is a pair of holes 1008 that must be covered by the user's lips in order to produce the required vacuum. As another alternative, mouthpiece 1000 may include bite landmarks 1010 for the user's front teeth. Similar bite marks may be provided for the user's bottom teeth.

Figure 89:
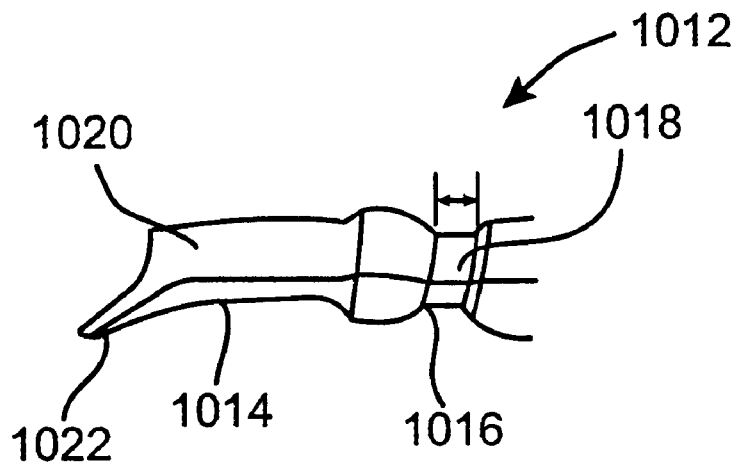

FIG. 89 illustrates another embodiment of a mouthpiece 1012 comprising a tubular member 1014 having a distal end 1016 that is slidable over a tubular extension 1018 that in turn is coupled to an aerosolization device. In this way, the user may adjust the distance between a proximal end 1020 of tubular member 1014 relative to the aerosolization device. According to one embodiment, the device is primed for actuation when tubular extension 1018 is in the patient's mouth and the patient applies a force against extension 1018 pushing extension 1018 forward in a direction towards the device, thus priming the device for actuation. Also, tubular member 1014 includes a tongue depressor 1022 that depresses the user's tongue during inhalation to facilitate passage of the aerosolized powder past the user's tongue and into the lungs.

The devices and methods of the present invention may be used with both liquid or powdered pharmaceutical formulations. The amount of active agent in the formulation will be that amount necessary to deliver a therapeutically effective amount of the active agent to achieve the desired result. In practice, this will vary widely depending upon the particular agent, the severity of the condition, and the desired therapeutic effect. According to a preferred embodiment for administering powdered formulations, pulmonary delivery is generally practical for active agents that must be delivered in doses of from 0.001 mg/day to 100 mg/day, preferably 0.01 mg/day to 50 mg/day.

Powdered formulations suitable for use in the present invention include dry powders and particles suspended or dissolved within a propellant. The powdered formulations have a particle size selected to permit penetration into the alveoli of the lungs, that is, preferably less than 10 $\mu$m mass median diameter (MMD), preferably less than 7.5 $\mu$m, and most preferably less than 5 $\mu$m, and usually being in the range of 0.1 $\mu$m to 5 $\mu$m in diameter. The emitted dose (ED) of these powders is >30%, usually >40%, preferably >50% and often >60% and the aerosol particle size distribution is about 1.0–5.0 $\mu$m mass median aerodynamic diameter (MMAD), usually 1.5–4.5 $\mu$m MMAD and preferably 1.5–4.0 $\mu$m MMAD. These dry powders have a moisture content below about 10% by weight, usually below about 5% by weight, and preferably below about 3% by weight. Such powders are described in WO 95/24183, WO 96/32149, and WO 99/16419 which are incorporated by reference herein.

The receptacles of the invention may conveniently be configured to have a penetrable access lid that is penetrated by one or more pointed structures when the aerosolization device is operated. Examples of such receptacles are described in U.S. Pat. Nos. 5,740,794 and 5,785,049, the complete disclosures of which are herein incorporated by reference.

The invention may utilize various deagglomeration mechanisms to deagglomerate the pharmaceutical formulation once it is extracted from the receptacle. For example, the flow path for the gases may experience one or more changes in direction to cause the pharmaceutical formulation to engage the walls of the flow path to deagglomerate the formulation. The flow path may also include various contractions or restrictions that may cause the pharmaceutical formulation to engage the walls of the flow path to deagglomerate the formulation. As another example, the flow path may include one or more obtrusions or obstacles that serve to engage the pharmaceutical formulation as it passes through the flow path. According to a preferred embodiment, the diameter of the deagglomeration mechanism is greater than that of the flow path.

The invention has now been described in detail for purposes of clarity of understanding. However, it will be appreciated that certain changes and modifications may be practiced within the scope of the appended claims.

What is claimed is:

1. A method for aerosolizing a pharmaceutical formulation, the method comprising:

placing a valve within an airway leading to the lungs to prevent respiratory gases from flowing to the lungs when user attempts to inhale, and then abruptly permitting respiratory gases to flow to the lungs by opening the valve when a threshold actuating vacuum caused by the attempted inhalation is exceeded, wherein the threshold actuating vacuum is in a range from about 20 cm $H_2O$ to about 60 cm $H_2O$; and using the flow of respiratory gases to extract a pharmaceutical formulation from a receptacle and to place the pharmaceutical formulation within the flow of respiratory gases to form an aerosol.

2. A method as in claim 1 wherein the permitted flow of respiratory gases to the lungs is limited to a rate that is less than a certain rate.

3. A method as in claim 2 wherein the certain rate is about 15 L/min.

4. A method as in claim 2 wherein the certain rate is about 8 L/min.

5. A method as in claim 2 wherein the certain rate is sufficient to permit an inhaled volume that is in the range from about 125 mL to about 1.25 L.

6. A method as in claim 2 wherein the flow limiting step comprises providing feedback when an excessive flow rate is produced to permit a user to adjust their inhalation rate.

7. A method as in claim 2 wherein the flow limiting step comprises regulating the size of the airway leading to the lungs.

8. A method as in claim 7 further comprising regulating the size of the airway with a spring biased ball that is disposed within a tapered opening such that the ball is drawn into the opening as the flow rate increases.

9. A method as in claim 7 further comprising regulating the size of the airway to permit a flow rate greater than the certain rate after a period of time has elapsed.

10. A method as in claim 7 wherein the size of the airway is regulated by an elastomeric membrane having an opening, the size of the opening varying with the flow rate.

11. A method as in claim 10 wherein the elastomeric membrane is an elastomeric duckbill valve.

12. A method as in claim 2 further comprising providing another airway to permit a flow rate greater than the certain rate after a period of time has lapsed.

13. A method as in claim 2 wherein the permitted flow of respiratory gases to the lungs is limited to a rate that is less than the certain rate for a certain period of time.

14. A method as in claim 13 wherein the certain period of time is from about 0.5 seconds to about 5 seconds.

15. A method as in claim 1 wherein the valve comprises an occlusion member having an opening, and a pull through member that is pulled through the opening when the threshold actuating vacuum is produced.

16. A method as in claim 15 wherein the occlusion member comprises an elastomeric membrane, and wherein the pull through member comprises a ball.

17. A method as in claim 1 wherein the pharmaceutical formulation comprises a powdered medicament, and further comprising using the flow of respiratory gases to deagglomerate the extracted powder.

18. A method as in claim 1 wherein the receptacle comprises a receptacle body having a chamber which holds the pharmaceutical formulation, and further comprising placing the receptacle in a position in communication with the airway.

19. A method as in claim 1 wherein the threshold actuating vacuum is in a range from about 40 cm $H_2O$ to about 60 cm $H_2O$.

20. A method as in claim 1 wherein the valve comprises a bistable member and wherein the bistable member moves from a first stable position to a second stable position when the threshold actuating vacuum is exceeded.

21. A method as in claim 1 wherein the pharmaceutical formulation is extracted downstream of the valve.

22. A method for administering a pharmaceutical formulation, the method comprising:
providing an inhalation device comprising a housing having a first opening to ambient air, a second opening to ambient air, a valve between said openings, and a mouthpiece at one of said openings;
preventing respiratory gases from flowing to the lungs when a user attempts to inhale through said mouthpiece;
permitting a first predetermined volume of respiratory gases to flow to the lungs, said first volume being sufficient to transport substantially all of a unit dose of a pharmaceutical formulation contained within the inhalation device out of the device and into the respiratory tract of a patient; and
permitting a second volume of respiratory gases to flow to the lungs.

23. A method as in claim 22 wherein the flow of respiratory gases is permitted by opening said valve when a threshold actuating vacuum by the attempted inhalation is exceeded.

24. A method as in claim 23 wherein said threshold actuating vacuum is from about 20 cm $H_2O$ to about 60 cm $H_2O$.

25. A method as in claim 23 wherein said threshold actuating vacuum is greater than about 40 cm $H_2O$.

26. A method as in claim 22 wherein said first predetermined volume of respiratory gases is in the range from 125 mL to 1.25 L.

27. A method as in claim 22 further comprising regulating the flow of respiratory gases at a first flow rate until said first predetermined volume of respiratory gases flows through said device.

28. A method as in claim 27 wherein the first flow rate is less than 15 L/min.

29. A method as in claim 27 further comprising regulating the flow of said second volume of respiratory gases at a second flow rate.

30. A method as in claim 22 wherein the valve comprises a bistable member and wherein the bistable member moves from a first stable position to a second stable position when a threshold actuating vacuum is exceeded.

31. A method as in claim 22 wherein the pharmaceutical formulation is downstream of the valve.

32. An aerosolization device comprising:
a housing defining an airway;
a coupling mechanism adapted to couple a receptacle containing a pharmaceutical formulation to the airway; and
a valve to prevent respiratory gases from flowing through the airway until a threshold actuating vacuum is exceeded at which time the valve opens to permit respiratory gases to flow through the airway and to extract the pharmaceutical formulation from the receptacle to form an aerosol wherein the threshold actuating vacuum of the valve is in a range from about 20 cm $H_2O$ to about 60 cm $H_2O$.

33. A device as in claim 32 further comprising a regulation system to regulate the flow of respiratory gases through the airway.

34. A device as in claim 33 wherein the regulation system is configured to limit the flow to a rate that is less than about 15 L/min.

35. A device as in claim 34 further comprising a flow integrator that is configured to open another airway in the housing after a certain period of time or a certain inhaled volume.

36. A device as in claim 34 wherein the regulation system limits the flow to a rate that is less than about 15 L/min for a certain period of time or for a certain inhaled volume.

37. A device as in claim 33 wherein the regulation system comprises a feedback mechanism to provide information related to the rate of flow of the respiratory gases.

38. A device as in claim 37 wherein the feedback mechanism comprises a whistle in communication with the airway.

39. A device as in claim 33 wherein the regulation system comprises a flow restrictor disposed in the airway, the flow restrictor defining an orifice sized to limit the flow of respiratory gases through the airway.

40. A device as in claim 39 wherein the flow restrictor comprises an elastomeric membrane to modulate the size of the airway.

41. A device as in claim 40 wherein the elastomeric membrane is an elastomeric duckbill valve that closes as the flow rate of the respiratory gases increases.

42. A device as in claim 39 wherein the flow restrictor comprises a spring biased ball that is drawn into a tapered opening as the flow rate of the respiratory gases increases.

43. A device as in claim 39 wherein the flow restrictor is adjustable to vary the rate of flow of respiratory gases through the airway.

44. A device as in claim 43 wherein the regulation system further comprises a control system to adjust the flow restrictor.

45. A device as in claim 44 wherein the control system is configured to limit the flow to a certain rate for a certain period of time or for a certain inhaled volume and then to adjust the flow restrictor to permit an increased flow of respiratory gases through the airway.

46. A device as in claim 32 wherein the valve comprises an occlusion member having an opening, and a pull through member that is pulled through the opening when the threshold actuating vacuum is produced.

47. A device as in claim 46 wherein the occlusion member comprises an elastomeric membrane, and wherein the pull though member comprises a ball.

48. A device as in claim 32 further comprising a deagglomeration mechanism disposed in the airway downstream of the receptacle to deagglomerate the extracted pharmaceutical formulation.

49. A device as in claim 32 wherein the valve is adapted to be disposed within the receptacle.

50. A device as in claim 32 wherein the device is adapted to removably receive the receptacle.

51. A device as in claim 32 wherein the threshold actuating vacuum is in a range from about 40 cm $H_2O$ to about 60 cm $H_2O$.

52. A device as in claim 32 wherein the valve comprises a bistable member and wherein the bistable member moves from a first stable position to a second stable position when the threshold actuating vacuum is exceeded.

53. A device as in claim 32 wherein the valve is positioned so that the pharmaceutical formulation is extracted downstream of the valve.

54. A method for aerosolizing a pharmaceutical formulation, the method comprising:

placing a valve within an airway leading to the lungs to prevent respiratory gases from flowing to the lungs when a user attempts to inhale, and then abruptly permitting respiratory gases to flow to the lungs by opening the valve when a threshold actuating vacuum caused by the attempted inhalation is exceeded, wherein the threshold actuating vacuum is in a range from about 20 cm $H_2O$ to about 60 cm $H_2O$; and using the flow of respiratory gases to extract a pharmaceutical formulation from a receptacle and to place the pharmaceutical formulation within the flow of respiratory gases to form an aerosol.

wherein the receptacle comprises a penetrable portion above a chamber which holds the pharmaceutical formulation, and further comprising penetrating the penetrable portion to expose the pharmaceutical formulation.

55. An aerosolization device comprising:

a housing defining an airway;

a coupling mechanism adapted to couple a receptacle containing a pharmaceutical formulation to the airway; and a valve to prevent respiratory gases from flowing through the airway until a threshold actuating vacuum is exceeded at which time the valve opens to permit respiratory gases to flow through the airway and to extract the pharmaceutical formulation from the receptacle to form an aerosol, wherein the threshold actuating vacuum of the valve is in a range from about 20 cm $H_2O$ to about 60 cm $H_2O$, wherein the device comprises a member adapted to penetrate a penetrable portion of the receptacle to expose the pharmaceutical formulation.

* * * * *